US009296828B2

(12) United States Patent
Valenta et al.

(10) Patent No.: US 9,296,828 B2
(45) Date of Patent: Mar. 29, 2016

(54) VACCINE CARRIER

(75) Inventors: Rudolf Valenta, Theresienfeld (AT);
Margarete Focke-Tejkl, Vienna (AT);
Birgit Linhart, Weißenkirchen (AT);
Susanne Vrtala, Vienna (AT); Peter Valent, Vienna (AT); Renate Reininger, Vienna (AT); Susanne Spitzauer, Vienna (AT); Ines Swoboda, Vienna (AT); Marianne Van Hage, Bromma (SE); Hans Grönlund, Lidingo (SE); Johanna Tinhofer, Vienna (AT); Kerstin Westritschnig, Vienna (AT); Theresia Popow-Kraupp, Vienna (AT)

(73) Assignee: BIOMAY AG, Vienna (AT)

( * ) Notice: Subject to any disclaimer, the term of this patent is extended or adjusted under 35 U.S.C. 154(b) by 304 days.

(21) Appl. No.: 12/304,267

(22) PCT Filed: Jun. 11, 2007

(86) PCT No.: PCT/AT2007/000281
§ 371 (c)(1),
(2), (4) Date: Dec. 10, 2008

(87) PCT Pub. No.: WO2007/140505
PCT Pub. Date: Dec. 13, 2007

(65) Prior Publication Data
US 2009/0324501 A1    Dec. 31, 2009

(30) Foreign Application Priority Data
Jun. 9, 2006 (AT) .................................. A 994/2006

(51) Int. Cl.
| A61K 38/00 | (2006.01) |
| A61K 39/00 | (2006.01) |
| A61K 39/35 | (2006.01) |
| A61K 39/36 | (2006.01) |
| A61K 39/385 | (2006.01) |
| C07H 21/02 | (2006.01) |
| C07H 21/04 | (2006.01) |
| C12N 15/00 | (2006.01) |
| C07K 19/00 | (2006.01) |
| C07K 14/415 | (2006.01) |

(52) U.S. Cl.
CPC .................. *C07K 19/00* (2013.01); *A61K 39/35* (2013.01); *A61K 39/36* (2013.01); *C07K 14/415* (2013.01); *A61K 2039/5256* (2013.01); *A61K 2039/5258* (2013.01); *C12N 2770/32734* (2013.01)

(58) Field of Classification Search
None
See application file for complete search history.

(56) References Cited

U.S. PATENT DOCUMENTS

| 2005/0123568 A1 | 6/2005 | Suck et al. |
| 2006/0088549 A1 | 4/2006 | Arnold |
| 2006/0121468 A1* | 6/2006 | Allnutt et al. ..................... 435/6 |
| 2006/0275312 A1 | 12/2006 | Chua et al. |
| 2007/0178122 A1 | 8/2007 | Geraci |
| 2007/0212374 A1 | 9/2007 | Schlegel et al. |
| 2008/0267985 A1 | 10/2008 | Fiebig et al. |
| 2008/0286311 A1 | 11/2008 | Westritschnig et al. |

FOREIGN PATENT DOCUMENTS

| EP | 0 358 485 | 3/1990 |
| WO | 02/12503 | 2/2002 |
| WO | 02/40676 | 5/2002 |
| WO | 03072601 A1 | 9/2003 |
| WO | 2004/003143 A2 | 1/2004 |
| WO | 2004/004761 A2 | 1/2004 |
| WO | 2006008018 A1 | 1/2006 |

OTHER PUBLICATIONS

Niederberger et al., IgE antibodies to recombinant pollen allergens (Phl p 1, Phl p 2, Phl p 5, and Bet v 2) account for a high percentage of grass pollen-specific IgE, 1998, Journal of Allergy and Clinical Immunology, vol. 101, pp. 258-264.*

Blaiss et al., Efficacy and safety of timothy grass allergy immunotherapy tablets in North American children and adolescents, 2011, Journal of Allergy and Clinical Immunology, vol. 127, pp. 64-71.*

Cordey et al. 'Rhinovirus Genome Evolution during Experimental Human Infection.' PLOS One 5(5): e10588.doi:10.1371/journal.pone.0010588, May 11, 2010.*

Blumenthal et al. 'Definition of an allergen.' Allergens and Allergen Immunotherapy. Ed. R. Lockey, S. Bukantzand j. Bousquet. New York: Marcel Decker, 2004. pp. 37-50.*

Ngo et, al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*

Skolnick et al. 'From genes to protein structure and function: novel applications of computational approaches in the genomic era.' Trends in Biotech. 18:34-39, 2000.*

Bauer, et al., "Generation of hypoallergenic DNA vaccines by forced ubiquitination: Preventive and therapeutic effects in a mouse model of allergy," Journal of Allergy and Clinical Immunology (2006), 118:269-276.

Bohle, et al., "A Novel Approach to Specific Allergy Treatment: The Recombinant Fusion Protein of a Bacterial Cell Surface (S-Layer) Protein and the Major Birch Pollen Allergen Bet v 1 (rSbsC-Bet v 1) Combines Reduced Allergenicity with Immunomodulating Capacity," J Immunol (2004), 172:6642-6648.

(Continued)

*Primary Examiner* — Nora Rooney
(74) *Attorney, Agent, or Firm* — Oblon, McClelland, Maier & Neustadt, L.L.P.

(57) ABSTRACT

The present invention relates to a hypoallergenic protein consisting of at least one hypoallergenic molecule derived from an allergen, which is fused or conjugated to at least one second non-allergenic protein or fragment thereof.

21 Claims, 21 Drawing Sheets

(56) References Cited

OTHER PUBLICATIONS

Breitwieser, et al., "A Novel Approach to Specific Allergy Treatment: The Recombinant Fusion Protein of a Bacterial Cell Surface (S-Layer) Protein and the Major Birch Pollen Allergen Bet v 1 (rSbsC-Bet v 1) Combines Reduced Allergenicity with Immunomodulating Capacity," Protein Engineering (2002), 15:243-249.

Elfman, et al., "IgE Binding Capacity of Synthetic and Recombinant Peptides of the Major Storage Mite (Lepidoglyphus destructor) Allergen," International Archives of Allergy and Immunology (1998), 117:167-173.

Gonzalez, et al., "Analysis of IgE and IgG B-cell immunodominant regions of Ole e 1, the main allergen from olive pollen," Molecular Immunology (2006), 43:570-578.

European Examination Report for EP 07 718 492.7 dated Jun. 29, 2010.

Focke, M. et al., "Nonanaphylactic synthetic peptides derived from B cell epitopes for the major grass pollen allergen. Phl p 1, for allergy vaccination," FASEB Journal (2001), 15:2042-2044.

Focke, M. et al., "Developments in allergen-specific immunotherapy: from allergen extracts to allergy vaccines bypassing allergen-specific immunoglobulin E and T cell reactivity<" Clinical and Experimental Allergy (2010), 40:385-397.

* cited by examiner

MCS p89VP1:                                                          Fig. 1B
             SD           Afl II
5'..TAAGAAGGAGATATA<u>CTTAAG</u>ATG AAC CCA GTT GAA AAT TAT ATA GAT
                             start  N   P   V   E   N   Y   I   D
AGT GTA TTA AAT GAA GTT CTT GTG GTG CCA AAT ATC CAA CCT AGC ACA
 S   V   L   N   E   V   L   V   V   P   N   I   Q   P   S   T
TCT GTG TCA AGT CGT GCA GCG CCT GCA TTG GAT GCT GCG GAA ACC
 S   V   S   S   H   A   A   P   A   L   D   A   A   E   T
GGA CAC ACC AGC TCT GTT CAA CCT GAA  GGT ATG ATT GAA ACT AGA
 G   H   T   S   S   V   Q   P   E   D   M   I   E   T   R
TAT GTT ATA ACT GAT CAA ACA AGG GAT GAA ACA AGT ATT GAG AGT TTC
 Y   V   I   T   D   Q   T   R   D   E   T   S   I   E   S   F
TTA GGT AGG TCA GGG TGT ATC GCT ATG ATA GAA TTT AAT ACA AGT AGT
 L   G   R   S   G   C   I   A   M   I   E   F   N   T   S   S
GAT AAA ACT GAA CAT GAT AAA ATT GGT AAA GGA TTC AAA ACA TGG AAG
 D   K   T   E   H   D   K   I   G   K   G   F   K   T   W   K
GTT AGT CTT CAA GAA ATG GCA CAA ATC AGA AGA AAA TAT GAA TTA TTC
 I   S   L   Q   E   M   A   Q   I   R   R   K   Y   E   L   F
ACA TAT ACA AGA TTT GAT TCA GAG ATA ACA ATA GTC ACT GCA GCC GCA
 T   Y   T   R   F   D   S   E   I   T   I   V   T   A   A   A
GCT CAA GGA AAT GAT AGT GGA CAT ATA GTA TTG CAA TTT ATG TAT GTA
 A   Q   G   D   D   S   G   H   I V L Q F M Y V CCC CCA GGA GCA CCT GTC CCC GAA AAA CGT GAT GAT TAC ACA TGG
P P G A P V P E K R D D Y T W CAA TCA GGA ACA AAT GCA TCT GTG TTC TGG CAA GAA GGA CAA CCA
Q S G T N A S V F W Q E G Q P

Fig. 1C

```
TAC CCC AGA TTC ACA ATC CCT TTT ATG AGC ATT GCA TCA GCC TAT TAC
 Y   P   R   F   T   I   P   F   M   S   I   A   S   A   Y   Y
ATG TTT TAT GAT GGT TAT GAT GGT GAT AGT GCA GCA TCA AAA TAC GGT
 M   F   Y   D   G   Y   D   G   D   S   A   A   S   K   Y   G
TCT GTA GTC ACT AAT GAT ATG GGA ACC ATA TGT GTT AGA ATA GTG ACA
 S   V   V   T   N   D   M   G   T   I   C   V   R   I   V   T
TCC AAC CAA AAA CAT GAT TTA AAT ATT GTG TGC CGC ATT TAC CAC AAG
 S   N   Q   K   H   D   L   N   I   V   C   R   I   Y   H   K
GCC AAA CAT ATA AAA GCA TGG  GT CCT CGC CCA CCA AGG GCT GTT GCC
 A   K   H   I   K   A   W   C   P   R   P   P   R   A   V   A
TAT CAA CAC ACA CAC TCA ACC AAT TAC ATA CCA TCC AAT GGT GAG GCC
 Y   Q   H   T   H   S   T   N   Y   I   P   S   N   G   E   A
ACA ACT CAG ATT AAA ACC AGA CCT GAT GTT TTT ACC GGT ACA AAC GTC
 T   T   Q   I   K   T   R   P   D   V   F   T   G   T   N   V
CAC CAC CAC CAC CAC CAC TGA GAA TTC TGC AGA TAT CCA TCA CAC
 H   H   H   H   H   H  stop EcoRI         EcoRV
TGG CGG CCG CTC GAG CAG ATC CGG CTG CTA ACA AAG CCC GAA AGG
    NotI
AAG CTG AGT TGG CTG CTG CCA CCG CTG AGC AAT AAC TAG .. 3'
```

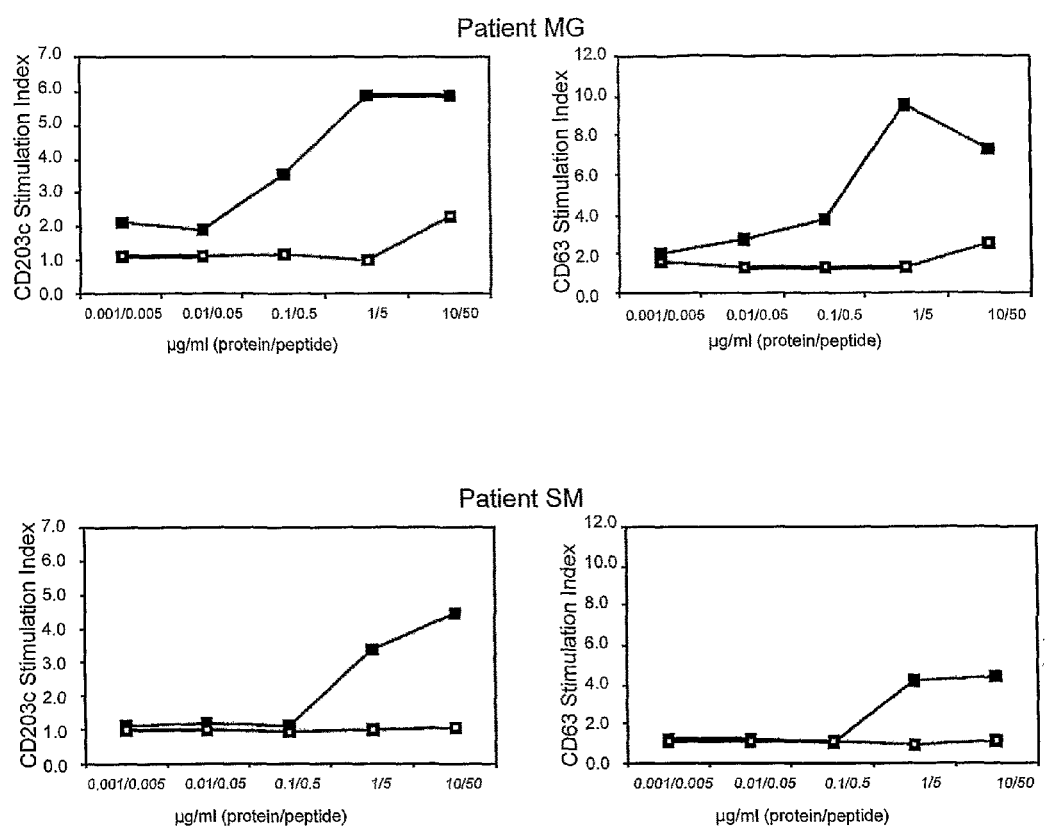
Cont. Fig. 17

IgE-reactivity

T-cell reactivity

VACCINE CARRIER

The present invention relates to novel hypoallergenic molecules and uses thereof.

Type I allergy is an IgE-mediated hypersensitivity disease affecting almost 25% of the population. It is based on the recognition of harmless airborne, insect, venom, food allergen and contact allergen antigens derived from per se harmless antigen sources such as pollen, insects, mold and animal proteins by specific immunoglobulin E. The crosslinking of effector cell-bound IgE antibodies leads to a release of inflammatory mediators (e.g., histamine, leukotrienes) and thus to the immediate symptoms of allergy (e.g., rhinoconjunctivitis, asthma, dermatitis, anaphylaxis). T-cell activation via IgE-dependent as well as IgE-independent mechanisms contributes to chronic allergic inflammation.

The probably only causative forms of allergy treatment is allergen-specific immunotherapy, which is based on the repeated administration of increasing amounts of allergen extracts for most sources. Numerous clinical studies have documented the clinical efficacy of injection immunotherapy and there is evidence for several immunological mechanisms underlying this treatment. Due to the difficulty to prepare high quality allergen extracts for certain allergen sources and the fact that the administration of allergens to patients can cause severe side effects, allergen-specific immunotherapy can only be recommended for certain patients groups and disease manifestations. It is especially difficult to treat patients with co-sensitizations to several different allergen sources and patients suffering from severe disease manifestations such as allergic asthma. Allergic asthma is one of the most vigorous manifestations of allergy, because it severely affects the quality of daily life, causes a high rate of hospitality admissions and can manifest itself in serious, life-threatening forms requiring intensive care of the patient.

Allergen extracts prepared from natural allergen-sources are crude in nature, and it is impossible to influence the quality and amounts of individual allergens in such preparations by technical means. They also contain numerous undefined non-allergenic components, and several recent studies indicate the poor quality of such extracts and document their great heterogeneity.

In the last decade great progress has been made in the field of molecular allergen characterization using recombinant DNA technology. A large number of the most important disease-eliciting allergens has been characterized down to the molecular level, and recombinant allergens mimicking the epitope complexity of natural allergen extracts have been produced. Moreover, several research groups have used the knowledge regarding allergen structures to develop defined new allergy vaccines. Genetic engineering, synthetic peptide chemistry and conjugation of allergens with immunostimulatory DNA sequences have been used to reduce the allergenic activity of the new vaccines and thus the rate of therapy-induced side effects. First promising clinical studies were conducted with such allergen derivatives. Interestingly, it turned out that although IgE-reactivity of genetically engineered recombinant allergens and allergen-derived synthetic T-cell epitope-containing peptides could be strongly reduced or even abolished, these derivatives still could induce systemic side effects appearing several hours after injection. For example, it was reported that T-cell epitope peptides of the major cat allergen, Fel d 1, induced asthma and bronchial hyper reactivity several hours after intracutaneous injection, and there is strong evidence that this effect is T-cell mediated and MHC-restricted.

These results indicate that the removal of IgE-reactivity diminishes IgE-mediated side effects since no immediate reactions were recorded in the course of these immunotherapy studies. However, the allergen-specific T-cell epitopes which have been preserved in the recombinant allergen derivatives as well as in the peptide mixtures are responsible for the late side effects (e.g. very problematic or atopic dermatitis, chronic T cell-mediated allergic skin manifestation). The side effects caused in the case of recombinant allergen-derivatives were relatively mild and in the case of the T-cell peptide vaccines may be overcome by adequate dosing. Both of the two new approaches therefore seem very promising for immunotherapy of allergic rhinoconjunctivitis but may have limitations when it comes to the treatment of severe forms of allergic asthma, where the induction of late side effects in the lung may be very problematic.

In order to administer and consequently to provoke an efficient immune response against peptides, polypeptides and proteins, adjuvants and/or carriers are regularly used. Complete Freund's adjuvant, for instance, is one of the most potent adjuvants available. However, because of its side effects, its use is not approved for humans. Therefore, there exists a need for vaccine compositions able to induce strong immune responses against peptides and polypeptides derived from allergens and of course of other antigens avoiding the use of complete Freund's adjuvant. Further, while BSA has been used successfully as a carrier in animal models it may not be appropriate for use in human vaccine compositions because of the risk of adverse reactions such as the risk of transmitting prion disease (variant Creutzfeldt-Jakob disease). A further challenge to the development of an effective vaccine against allergens is the need for an immune response able to rapidly decrease allergens in an individual or animal. Therefore, high concentrations of allergen-specific antibodies in the blood, which are mainly of the IgG subtype, are needed. In mucosal surfaces IgA antibodies are the primary subtype.

Cholera toxin, a known carrier protein in the art, is also used regularly as an adjuvant, eliminating the need for complete Freund's adjuvant in a vaccine composition. However, cholera toxin increases total and specific IgE antibody levels and leads to IgE-associated inflammatory reactions.

Due to the side effects provoked by most carrier proteins used for vaccination, there exists a need for carrier systems which are able to stimulate immune responses against allergens or other antigens, without using toxic adjuvants, without using poorly tolerated carrier proteins and, in certain situations, without stimulation of potentially pathologic immune responses. Novel carrier systems meeting these specifications can be used towards the formation of novel conjugates and compositions suitable for the treatment or prevention of diseases like allergic diseases.

In Bohle B. et al. (J. Immunol. 172 (11) (2004): 6642-6648) a recombinant fusion protein comprising an S-layer protein moiety and Bet v 1 moiety is described. This molecule comprises the native hyperallergenic Bet v 1 protein.

WO 2004/004761 relates to virus like particles which are fused to an immunogen and which may be used for immunisation.

In WO 2004/003143 the use of fusion proteins comprising a virus like particle and a hyperallergenic molecule as immunogen for vaccination is disclosed.

It is an object of the present invention to provide medicaments and carriers which overcome the aforementioned drawbacks and allow an allergen vaccination with reduced side effects.

Therefore, the present invention relates to a hypoallergenic protein consisting of at least one hypoallergenic molecule derived from an allergen, which is fused or conjugated to at least one second non-allergenic protein or fragment thereof.

In order to provoke an enhanced immune response against a molecule, in particular of a hypoallergenic molecule according to the present invention, said molecule is fused (by genetic engineering) or conjugated (by chemical reactions) to a carrier. A conventional and regularly employed carrier is, for instance, KLH (Keyhole limpet hemocyanin). KLH, which is isolated from the giant sea mollusc *Megathura crenulata*, is one of the most popular carrier proteins used to create an immunogen for injection. KLH induces a strong antibody response because of its large mass and because it is a non-mammalian protein.

The second protein (the "carrier" or "carrier protein") to be fused or conjugated to a hypoallergenic molecule of the invention is not derived from an allergen ("non-allergenic"). However, the carrier protein used in the present invention may exhibit T cell reactivity and/or provoke an immune response against itself and the hypoallergenic molecule fused or conjugated to it when administered to an animal or human body. Consequently, if the carrier protein is derived from a pathogen (e.g. virus, bacteria etc.), (protecting) antibodies directed to said carrier and pathogens are produced.

As used herein, "hypoallergenic protein" means a fusion protein/polypeptide of a carrier of a non-allergenic source with a hypoallergenic molecule. Furthermore, a "hypoallergenic protein" is also intended to be a conjugation product (e.g. chemical coupling, adsorption) of a carrier with a hypoallergenic molecule.

"Hypoallergenic" as used herein, refers to molecules with reduced allergenic potential. Such molecules have a decreased capacity to provoke allergic reactions in an individual compared to the wild-type protein from which these molecules are derived.

The at least one hypoallergenic molecule derived from an allergen and fused/conjugated to a second protein is preferably C- and/or N-terminally truncated. "C- and/or N-terminal truncation", as used herein, means that amino acid residues either from the N-terminus or from the C-terminus or both from the N- and C-terminus of the wild-type allergen are removed by deletion of at least 1, 2, 3, 4, 5, 7, 10, 15, 20, 30 amino acid residues.

The hypoallergenic molecules, i.e. peptides/polypeptides, comprise preferably 10 to 50 amino acids, more preferably 15 to 40 amino acids, in particular 20-30 amino acids and exhibit reduced IgE reactivity. These molecules are designed to exclude T-cell epitopes which may cause T-cell-mediated side effects. T-cell epitopes and molecules exhibiting reduced T-cell response may be determined and identified by methods known by the person skilled in the art (e.g., Bercovici N. et al. Clin Diagn Lab Immunol. (2000) 7:859-864).

It was found that it is possible to design peptide vaccines derived from allergens like the major grass pollen allergens, e.g., Phl p 1, and for the major birch pollen allergen, Bet v 1, using surface exposed peptides. The data obtained show that such peptide vaccines can be produced for any allergen whose primary structure is known according to IgE epitope mapping, three-dimensional structure data or computer-aided prediction of surface-exposed domains. However, the selection of suitable peptides which may be used for vaccination remains crucial, because not all peptides identified with these methods can be employed in vaccination. The peptides suitably used for vaccination purposes should exhibit reduced IgE-binding capacity and—in order to reduce or avoid late side effects—exhibit reduced T-cell reactivity.

The term "derived from an allergen", as used herein, means that the hypoallergenic molecules according to the present invention are obtained directly from an allergen by fragmentation or truncation. The amino acid sequence of the hypoallergenic molecules of the present invention are preferably at least 80% identical, more preferably at least 90% identical, most preferably at least 95% identical, in particular 100% identical, to the amino sequence stretch of the wild-type allergen, from which the hypoallergenic molecule is derived. However, the molecules which are not 100% identical to the wild-type allergen fragments should be able to bind with at least 60%, preferably at least 70%, more preferably at least 80%, most preferably at least 90%, strength to an antibody or to antibodies, preferably to IgG antibodies, which are directed to said wild-type allergen fragments.

The degree of identity of a first amino acid sequence to a second amino acid can be determined by a direct comparison between both amino acid sequences using certain algorithms. Such algorithms are, for instance, incorporated in various computer programs (e.g. "BLAST 2 SEQUENCES (blastp)" (Tatusova et al. (1999) FEMS Microbiol. Lett. 174:247-25; Corpet F, Nucl. Acids Res. (1988) 16:10881-10890).

The truncated molecules according to the present invention can be defined as being parts of the complete allergen that induce less activation of allergen-specific T cells than the complete wild-type allergen (preferably at least a 30%, more preferably at least a 50%, most preferably at least a 70%, reduction), exhibit a more than 50% reduced (preferably more than 70%) allergenic activity as evaluated by IgE binding assays and ability to induce IgE-mediated cell activation and when coupled to a carrier as described induce IgG antibodies which inhibit the binding of polyclonal IgE from allergic patients to the complete wild-type allergen.

The peptides should contain sequences from the allergens to avoid overlaps with the mimotopes. Mimotopes, however, which are small peptide mimics (less than 15 amino acids) of antigen pieces and are obtained from random peptide libraries do not represent original, allergen-derived molecules as defined herein. They can not be used according to the invention because they are too small to induce a robust blocking IgG response.

The hypoallergenic molecules according to the present invention may be obtained by recombinant methods or chemical synthesis. Alternatively, it is, of course, also possible to obtain the molecules by enzymatic or chemical cleavage of the wild-type allergen or a polypeptide/protein harbouring the molecule of interest.

The hypoallergenic molecule may comprise preferably at least two truncated allergen molecules derived from at least one allergen, wherein the order of the truncated allergen fragments differs from the order of the fragments in the wild-type allergen if the at least two molecules are derived from the same allergen.

The hypoallergenic molecule according to the present invention may comprise one or more (preferably at least 2, more preferably at least 3) hypoallergenic molecules as defined herein, thus, resulting in a fusion protein. The single hypoallergenic molecules of the fusion protein, which, of course, also lacks IgE-binding capacity and lacks T-cell epitopes, may be derived from allergens of the same and/or of different origin. If the molecules are derived from the same allergen, the order in the hypoallergenic fusion protein should not be identical to the order in the wild-type allergen (this prevents the reconstitution and formation of IgE-binding sites) (see, e.g., WO2004/065414, Linhart B and Valenta R (Int Arch Allergy Immunol. (2004) 134:324-31)).

According to a preferred embodiment of the present invention the at least one hypoallergenic molecule is fused to the N-terminus and/or C-terminus of said at least one second protein or fragment thereof.

The allergen or fragments thereof may be conjugated chemically, e.g., or by recombinant methods to each other. If the allergen or fragment thereof is conjugated chemically to a carrier, said allergen or fragment should be provided with a terminal cysteine residue (resulting in a free sulfhydryl group). To said terminal, (N- or C-terminal) cysteine residue any maleimide-activated carrier protein may be conjugated, thus creating an immunogen/carrier complex. If the allergen or fragment thereof does not have a sulfhydryl group at a terminus, EDC (1-ethyl-3-(3-dimethylaminopropyl) carbodiimide hydrochloride) chemistry in order to couple amines (lysine) or carboxylic acids (glutamic, aspartic acid or 5-phosphate) to the carrier protein may be employed.

If the hypoallergenic molecule fused to the N- or C-terminus of the carrier, recombinant methods are employed.

According to a preferred embodiment of the present invention the at least one second protein is a viral, in particular RNA or DNA viral, bacterial fungal or protozoal protein.

The at least one second protein ("carrier") may be of any of the above-mentioned origin. It is, however, in particular preferred to use proteins which provoke an immune response against the protein itself and the hypoallergenic molecule fused or conjugated thereto. Due to the induction of formation of (protective) antibodies directed also to the at least one second protein, the hypoallergenic protein according to the present invention may also be employed as vaccine for said second protein and its originating source (e.g. virus, bacteria, fungus). Of course it is also possible to use carrier proteins well known in the art (e.g. KLH) as the at least second protein.

The viral protein according to the present invention is preferably a capsid protein.

Viral capsid proteins are especially suited because they induce antiviral activity, provoke the formation of antibodies which block adhesion of viruses, e.g. rhinoviruses, to epithelial cells, exhibit an immuno-modulatory activity towards a Th1 response, increase the immunogenicity of the peptide (i.e., higher anti-peptide and hence higher levels of protective IgG antibodies), are suited and proved for prophylactic vaccination (virus vaccination) and are safe, when capsid proteins are used to whose humans are continuously exposed (e.g. rhinoviruses).

According to another preferred embodiment of the present invention the at least one viral capsid protein is derived from a human pathogenic virus, preferably a virus of the family of picornaviridae.

The virus of the family of picornaviridae is preferably of the genus of rhinoviruses, preferably of the species of human rhinoviruses, in particular human rhinovirus 89 and 14. The capsid protein may be VP1, VP2, VP3 and/or VP4.

The allergen to be fused to a viral capsid protein is preferably selected from the group consisting of major birch pollen allergens, in particular Bet v 1 and Bet v 4, major timothy grass pollen allergens, in particular Phl p 1, Phl p 2, Phl p 5, Phl p 6 and Phl p 7, major house dust mite allergens, in particular Der p 1 and Der p 2, major cat allergen Fel d 1, major bee allergens, major wasp allergens, profilins, especially Phl p 12, and storage mite allergens, especially Lep d 2.

Other suited allergens to be used according to the present invention can be derived from the following table.

| | | ALLERGENS | | | |
|---|---|---|---|---|---|
| Species Name | Allergen Name | Biochem. ID or Obsolete name | MW | cDNA (C) or protein (P) | Reference, Acc. No. |
| *Ambrosia artemisiifolia* short ragweed | Amb a 1 | antigen E | 8 | C | 8, 20 |
| | Amb a 2 | antigen K | 38 | C | 8, 21 |
| | Amb a 3 | Ra3 | 11 | C | 22 |
| | Amb a 5 | Ra5 | 5 | C | 11, 23 |
| | Amb a 6 | Ra6 | 10 | C | 24, 25 |
| | Amb a 7 | Ra7 | 12 | P | 26 |
| *Ambrosia trifida* giant ragweed | Amb t 5 | Ra5G | 4.4 | C | 9, 10, 27 |
| *Artemisia vulgaris* mugwort | Art v 1 | | 27-29 | C | 28 |
| | Art v 2 | | 35 | P | 28A |
| | Art v 3 | lipid transfer protein | 12 | P | 53 |
| | Art v 4 | profilin | 14 | C | 29 |
| *Helianthus annuus* sunflower | Hel a 1 | | 34 | | 29A |
| | Hel a 2 | profilin | 15.7 | C | Y15210 |
| *Mercurialis annua* Caryophyllales | Mer a 1 | profilin | 14-15 | C | Y13271 |
| *Chenopodium album* lamb's-quarters, pigweed, white goosefoot | Che a 1 | | 17 | C | AY049012, 29B |
| | Che a 2 | profilin | 14 | C | AY082337 |
| | Che a 3 | polcalcin | 10 | C | AY082338 |
| *Salsola kali* Russian-thistle Rosales | Sal k 1 | | 43 | P | 29C |
| *Humulus japonicus* Japanese hop | Hum j 4w | | | C | AY335187 |
| *Parietaria judaica* | Par j 1 | lipid transfer protein 1 | 15 | C | see list of isoallergens |
| | Par j 2 | lipid transfer protein 2 | | C | see list of isoallergens |
| | Par j 3 | profilin | | C | see list of isoallergens |
| *Parietaria officinalis* B. Grasses | Par o 1 | lipid transfer protein | 15 | | 29D |

-continued

ALLERGENS

| Species Name | Allergen Name | Biochem. ID or Obsolete name | MW | cDNA (C) or protein (P) | Reference, Acc. No. |
|---|---|---|---|---|---|
| Poales | | | | | |
| *Cynodon dactylon* | Cyn d 1 | | 32 | C | 30, S83343 |
| Bermuda grass | Cyn d 7 | | | C | 31, X91256 |
| | Cyn d 12 | profilin | 14 | C | 31a, Y08390 |
| | Cyn d 15 | | 9 | C | AF517686 |
| | Cyn d 22w | enolase | | | data pending |
| | Cyn d 23 | Cyn d 14 | 9 | C | AF517685 |
| | Cyn d 24 | Pathogenesis-related p. | 21 | P | pending |
| *Dactylis glomerata* | Dac g 1 | AgDg1 | 32 | P | 32 |
| orchard grass | Dac g 2 | | 11 | C | 33, S45354 |
| | Dac g 3 | | | C | 33A, U25343 |
| | Dac g 5 | | 31 | P | 34 |
| *Festuca pratensis* | Fes p 4w | | 60 | — | |
| meadow fescue | | | | | |
| *Holcus lanatus* | Hol l 1 | | | C | Z27084 |
| velvet grass | | | | | |
| *Lolium perenne* | Lol p 1 | group I | 27 | C | 35, 36 |
| rye grass | Lol p 2 | group II | 11 | P | 37, 37A, X73363 |
| | Lol p 3 | group III | 11 | P | 38 |
| | Lol p 5 | Lol p IX, Lol p Ib | 31/35 | C | 34, 39 |
| | Lol p 11 | hom: trypsin inhibitor | 16 | | 39A |
| *Phalaris aquatica* | Pha a 1 | | | C | 40, S80654 |
| canary grass | | | | | |
| *Phleum pratense* | Phl p 1 | | 27 | C | X78813 |
| timothy | Phl p 2 | | | C | X75925, 41 |
| | Phl p 4 | | | P | 41A |
| | Phl p 5 | Ag25 | 32 | C | 42 |
| | Phl p 6 | | | C | Z27082, 43 |
| | Phl p 11 | trypsin inhibitor hom. | 20 | C | AF521563, 43A |
| | Phl p 12 | profilin | | C | X77583, 44 |
| | Phl p 13 | polygalacturonase | 55-60 | C | AJ238848 |
| *Poa pratensis* | Poa p 1 | group I | 33 | P | 46 |
| Kentucky blue grass | Poa p 5 | | 31/34 | C | 34, 47 |
| *Sorghum halepense* | Sor h 1 | | | C | 48 |
| Johnson grass | | | | | |
| C. Trees | | | | | |
| Arecales | | | | | |
| *Phoenix dactylifera* | Pho d 2 | profilin | 14.3 | C | Asturias p.c. |
| date palm | | | | | |
| Fagales | | | | | |
| *Alnus glutinosa* | Aln g 1 | | 17 | C | S50892 |
| alder | | | | | |
| *Betula verrucosa* | Bet v 1 | | 17 | C | see list of isoallergens |
| birch | Bet v 2 | profilin | 15 | C | M65179 |
| | Bet v 3 | | | C | X79267 |
| | Bet v 4 | | 8 | C | X87153, S54819 |
| | Bet v 6 | h: isoflavone reductase | 33.5 | C | see list of isoallergens |
| | Bet v 7 | cyclophilin | 18 | P | P81531 |
| *Carpinus betulus* | Car b 1 | | 17 | C | see list of isoallergens |
| hornbeam | | | | | |
| *Castanea sativa* | Cas s 1 | | 22 | P | 52 |
| chestnut | Cas s 5 | chitinase | | | |
| | Cas s 8 | lipid transfer protein | 9.7 | P | 53 |
| *Corylus avellana* | Cor a 1 | | 17 | C | see list of isoallergens |
| hazel | Cor a 2 | profilin | 14 | C | |
| | Cor a 8 | lipid transfer protein | 9 | C | |
| | Cor a 9 | 11S globulin-like protein | 40/? | C | Beyer p.c. |
| | Cor a 10 | luminal binding prot. | 70 | C | AJ295617 |
| | Cor a 11 | 7S vicilin-like prot. | 48 | C | AF441864 |
| *Quercus alba* | Que a 1 | | 17 | P | 54 |
| White oak | | | | | |
| Lamiales | | | | | |
| Oleaceae | | | | | |
| *Fraxinus excelsior* | Fra e 1 | | 20 | P | 58A, AF526295 |
| ash | | | | | |
| *Ligustrum vulgare* | Lig v 1 | | 20 | P | 58A |
| privet | | | | | |
| *Olea europea* | Ole e 1 | | 16 | C | 59, 60 |

ALLERGENS

| Species Name | Allergen Name | Biochem. ID or Obsolete name | MW | cDNA (C) or protein (P) | Reference, Acc. No. |
|---|---|---|---|---|---|
| olive | Ole e 2 | profilin | 15-18 | C | 60A |
| | Ole e 3 | | 9.2 | | 60B |
| | Ole e 4 | | 32 | P | P80741 |
| | Ole e 5 | superoxide dismutase | 16 | P | P80740 |
| | Ole e 6 | | 10 | C | 60C, U86342 |
| | Ole e 7 | | ? | P | 60D, P81430 |
| | Ole e 8 | Ca2+-binding protein | 21 | C | 60E, AF078679 |
| | Ole e 9 | beta-1,3-glucanase | 46 | C | AF249675 |
| | Ole e 10 | glycosyl hydrolase hom. | 11 | C | 60F, AY082335 |
| *Syringa vulgaris* lilac Plantaginaceae | Syr v 1 | | 20 | P | 58A |
| *Plantago lanceolata* English plantain Pinales | Pla l 1 | | 18 | P | P842242 |
| *Cryptomeria japonica* sugi | Cry j 1 | | 41-45 | C | 55, 56 |
| | Cry j 2 | | | C | 57, D29772 |
| *Cupressus arisonica* cypress | Cup a 1 | | 43 | C | A1243570 |
| *Cupressus sempervirens* common cypress | Cup s 1 | | 43 | C | see list of isoallergens |
| | Cup s 3w | | 34 | C | ref pending |
| *Juniperus ashei* mountain cedar | Jun a 1 | | 43 | P | P81294 |
| | Jun a 2 | | | C | 57A, AJ404653 |
| | Jun a 3 | | 30 | P | 57B, P81295 |
| *Juniperus oxycedrus* prickly juniper | Jun o 4 | hom: calmodulin | 29 | C | 57C, AF031471 |
| *Juniperus sabinoides* mountain cedar | Jun s 1 | | 50 | P | 58 |
| *Juniperus virginiana* eastern red cedar Platanaceae | Jun v 1 | | 43 | P | P81825, 58B |
| *Platanus acerifolia* London plane tree | Pla a 1 | | 18 | P | P82817 |
| | Pla a 2 | | 43 | P | P82967 |
| | Pla a 3 | lipid transfer protein | 10 | P | Iris p.c. |
| D. Mites | | | | | |
| *Acarus siro* mite | Aca s 13 | arthropod fatty acid binding prot. | 14* | C | AJ006774 |
| *Blomia tropicalis* mite | Blo t 1 | cysteine protease | 39 | C | AF277840 |
| | Blo t 3 | trypsin | 24* | C | Cheong p.c. |
| | Blo t 4 | alpha amylase | 56 | C | Cheong p.c. |
| | Blo t 5 | | | C | U59102 |
| | Blo t 6 | chymotrypsin | 25 | C | Cheong p.c. |
| | Blo t 10 | tropomyosin | 33 | C | 61 |
| | Blo t 11 | paramyosin | 110 | C | AF525465, 61A |
| | Blo t 12 | Bt1a | | C | U27479 |
| | Blo t 13 | Bt6, fatty acid bind prot. | | C | U58106 |
| | Blo t 19 | anti-microbial pep. hom. | 7.2 | C | Cheong p.c. |
| *Dermatophagoides farinae* American house dust mite | Der f 1 | cysteine protease | 25 | C | 69 |
| | Der f 2 | | 14 | C | 70, 70A, see list of isoallergens |
| | Der f 3 | trypsin | 30 | C | 63 |
| | Der f 7 | | 24-31 | C | SW: Q26456, 71 |
| | Der f 10 | tropomyosin | | C | 72 |
| | Der f 11 | paramyosin | 98 | C | 72A |
| | Der f 14 | mag3, apolipophorin | | C | D17686 |
| | Der f 15 | 98k chitinase | 98 | C | AF178772 |
| | Der f 16 | gelsolin/villin | 53 | C | 71A |
| | Der f 17 | Ca binding EF protein | 53 | C | 71A |
| | Der f 18w | 60k chitinase | 60 | C | Weber p.c. |
| *Dermatophagoides microceras* house dust mite | Der m 1 | cysteine protease | 25 | P | 68 |
| *Dermatophagoides pteronyssinus* European house dust mite | Der p 1 | antigen P1, cysteine protease | 25 | C | 62, see list of isoallergens |
| | Der p 2 | | 14 | C | 62A-C, see list of isoallergens |
| | Der p 3 | trypsin | 28/30 | C | 63 |
| | Der p 4 | amylase | 60 | P | 64 |
| | Der p 5 | | 14 | C | 65 |

ALLERGENS

| Species Name | Allergen Name | Biochem. ID or Obsolete name | MW | cDNA (C) or protein (P) | Reference, Acc. No. |
|---|---|---|---|---|---|
| | Der p 6 | chymotrypsin | 25 | P | 66 |
| | Der p 7 | | 22/28 | C | 67 |
| | Der p 8 | glutathione transferase | | C | 67A |
| | Der p 9 | collagenolytic serine pro. | | P | 67B |
| | Der p 10 | tropomyosin | 36 | C | Y14906 |
| | Der p 14 | apolipophorin like prot. | | C | Epton p.c. |
| *Euroglyphus maynei* mite | Eur m 2 | | | C | see list of isoallergens |
| | Eur m 14 | apolipophorin | 177 | C | AF149827 |
| *Glycyphagus domesticus* storage mite | Gly d 2 | | | C | 72B, see isoallergen list |
| *Lepidoglyphus destructor* storage mite | Lep d 2 Lep d 1 | | 15 | C | 73, 74, 74A, see isoallergen list |
| | Lep d 5 | | | C | 75, AJ250278 |
| | Lep d 7 | | | C | 75, AJ271058 |
| | Lep d 10 | tropomyosin | | C | 75A, AJ250096 |
| | Lep d 13 | | | C | 75, AJ250279 |
| *Tyrophagus putrescentiae* storage mite | Tyr p 2 | | | C | 75B, Y12690 |
| E. Animals | | | | | |
| *Bos domesticus* domestic cattle (see also foods) | Bos d 2 | Ag3, lipocalin | 20 | C | 76, see isoallergen list |
| | Bos d 3 | Ca-binding S100 hom. | 11 | C | L39834 |
| | Bos d 4 | alpha-lactalbumin | 14.2 | C | M18780 |
| | Bos d 5 | beta-lactoglobulin | 18.3 | C | X14712 |
| | Bos d 6 | serum albumin | 67 | C | M73993 |
| | Bos d 7 | immunoglobulin | 160 | | 77 |
| | Bos d 8 | caseins | 20-30 | | 77 |
| *Canis familiaris* (*Canis domesticus*) dog | Can f 1 | | 25 | C | 78, 79 |
| | Can f 2 | | 27 | C | 78, 79 |
| | Can f 3 | albumin | | C | S72946 |
| | Can f 4 | | 18 | P | A59491 |
| *Equus caballus* domestic horse | Equ c 1 | lipocalin | 25 | C | U70823 |
| | Equ c 2 | lipocalin | 18.5 | P | 79A, 79B |
| | Equ c 3 | Ag3-albumin | 67 | C | 79C, X74045 |
| | Equ c 4 | | 17 | P | 79D |
| | Equ c 5 | AgX | 17 | P | Goubran Botros p.c. |
| *Felis domesticus* cat (saliva) | Fel d 1 | cat-1 | 38 | C | 15 |
| | Fel d 2 | albumin | | C | 79E, X84842 |
| | Fel d 3 | cystatin | 11 | C | 79F, AF238996 |
| | Fel d 4 | lipocalin | 22 | C | AY497902 |
| | Fel d 5w | immunoglobulin A | 400 | | Adedoyin p.c. |
| | Fel d 6w | immunoglobulin M | 800-1000 | | Adedoyin p.c. |
| | Fel d 7w | immunoglobulin G | 150 | | Adedoyin p.c. |
| *Cavia porcellus* guinea pig | Cav p 1 | lipocalin homologue | 20 | P | SW: P83507, 80 |
| | Cav p 2 | | 17 | P | SW: P83508 |
| *Mus musculus* mouse (urine) | Mus m 1 | MUP | 19 | C | 81, 81A |
| *Rattus norvegius* rat (urine) | Rat n 1 | | 17 | C | 82, 83 |
| F. Fungi (moulds) | | | | | |
| 1. Ascomycota | | | | | |
| 1.1 Dothideales | | | | | |
| *Alternaria alternata* | Alt a 1 | | 28 | C | U82633 |
| | Alt a 2 | | 25 | C | 83A, U62442 |
| | Alt a 3 | heat shock prot. | 70 | C | U87807, U87808 |
| | Alt a 4 | prot. disulfideisomerase | 57 | C | X84217 |
| | Alt a 6 | acid ribosomal prot. P2 | 11 | C | X78222, U87806 |
| | Alt a 7 | YCP4 protein | 22 | C | X78225 |
| | Alt a 10 | aldehyde dehydrogenase | 53 | C | X78227, P42041 |
| | Alt a 11 | enolase | 45 | C | U82437 |
| | Alt a 12 | acid ribosomal prot. P1 | 11 | C | X84216 |
| *Cladosporium herbarum* | Cla h 1 | | 13 | | 83B, 83C |
| | Cla h 2 | | 23 | | 83B, 83C |
| | Cla h 3 | aldehyde dehydrogenase | 53 | C | X78228 |
| | Cla h 4 | acid ribosomal prot. P2 | 11 | C | X78223 |
| | Cla h 5 | YCP4 protein | 22 | C | X78224 |
| | Cla h 6 | enolase | 46 | C | X78226 |
| | Cla h 12 | acid ribosomal prot. P1 | 11 | C | X85180 |

ALLERGENS

| Species Name | Allergen Name | Biochem. ID or Obsolete name | MW | cDNA (C) or protein (P) | Reference, Acc. No. |
|---|---|---|---|---|---|
| 1.2 Eurotiales | | | | | |
| *Aspergillus flavus* | Asp fl 13 | alkaline serine protease | 34 | | 84 |
| *Aspergillus fumigatus* | Asp f 1 | | 18 | C | M83781, S39330 |
| | Asp f 2 | | 37 | C | U56938 |
| | Asp f 3 | peroxisomal protein | 19 | C | U20722 |
| | Asp f 4 | | 30 | C | AJ001732 |
| | Asp f 5 | metalloprotease | 40 | C | Z30424 |
| | Asp f 6 | Mn superoxide dismut. | 26.5 | C | U53561 |
| | Asp f 7 | | 12 | C | AJ223315 |
| | Asp f 8 | ribosomal prot. P2 | 11 | C | AJ224333 |
| | Asp f 9 | | 34 | C | AJ223327 |
| | Asp f 10 | aspartic protease | 34 | C | X85092 |
| | Asp f 11 | peptidyl-prolyl isomeras | 24 | | 84A |
| | Asp f 12 | heat shock prot. P90 | 90 | | 85 |
| | Asp f 13 | alkaline serine protease | 34 | | 84B |
| | Asp f 15 | | 16 | C | AJ002026 |
| | Asp f 16 | | 43 | C | g3643813 |
| | Asp f 17 | | | C | AJ224865 |
| | Asp f 18 | vacuolar serine protease | 34 | | 84C |
| | Asp f 22w | enolase | 46 | C | AF284645 |
| | Asp f 23 | L3 ribosomal protein | 44 | C | 85A, AF464911 |
| *Aspergillus niger* | Asp n 14 | beta-xylosidase | 105 | C | AF108944 |
| | Asp n 18 | vacuolar serine protease | 34 | C | 84B |
| | Asp n 25 | 3-phytase B | 66-100 | C | 85B, P34754 |
| | Asp n ? | | 85 | C | Z84377 |
| *Aspergillus oryzae* | Asp o 13 | alkaline serine protease | 34 | C | X17561 |
| | Asp o 21 | TAKA-amylase A | 53 | C | D00434, M33218 |
| *Penicillium brevicompactum* | Pen b 13 | alkaline serine protease | 33 | | 86A |
| *Penicillium chrysogenum* | Pen ch 13 | alkaline serine protease | 34 | | 87 |
| (formerly *P. notatum*) | Pen ch 18 | vacuolar serine protease | 32 | | 87 |
| | Pen ch 20 | N-acetyl glucosaminidas | 68 | | 87A |
| *Penicillium citrinum* | Pen c 3 | peroxisomal mem. prot. | 18 | | 86B |
| | Pen c 13 | alkaline serine protease | 33 | | 86A |
| | Pen c 19 | heat shock prot. P70 | 70 | C | U64207 |
| | Pen c 22w | enolase | 46 | C | AF254643 |
| | Pen c 24 | elongation factor 1 beta | | C | AY363911 |
| *Penicillium oxalicum* | Pen o 18 | vacuolar serine protease | 34 | | 87B |
| 1.3 Hypocreales | | | | | |
| *Fusarium culmorum* | Fus c 1 | ribosomal prot. P2 | 11* | C | AY077706 |
| | Fus c 2 | thioredoxin-like prot. | 13* | C | AY077707 |
| 1.4 Onygenales | | | | | |
| *Trichophyton rubrum* | Tri r 2 | | | C | 88 |
| | Tri r 4 | serine protease | | C | 88 |
| *Trichophyton tonsurans* | Tri t 1 | | 30 | P | 88A |
| | Tri t 4 | serine protease | 83 | C | 88 |
| 1.5 Saccharomycetales | | | | | |
| *Candida albicans* | Cand a 1 | | 40 | C | 89 |
| | Cand a 3 | peroxisomal protein | 29 | C | AY136739 |
| *Candida boidinii* | Cand b 2 | | 20 | C | J04984, J04985 |
| 2. Basidiomycotina | | | | | |
| 2.1 Hymenomycetes | | | | | |
| *Psilocybe cubensis* | Psi c 1 | | | | |
| | Psi c 2 | cyclophilin | 16 | | 89A |
| *Coprinus comatus* | Cop c 1 | leucine zipper protein | 11 | C | AJ132235 |
| shaggy cap | Cop c 2 | | | | AJ242791 |
| | Cop c 3 | | | | AJ242792 |
| | Cop c 5 | | | | AJ242793 |
| | Cop c 7 | | | | AJ242794 |
| 2.2 Urediniomycetes | | | | | |
| *Rhodotorula mucilaginosa* | Rho m 1 | enolase | 47 | C | 89B |
| | Rho m 2 | vacuolar serine protease | 31 | C | AY547285 |
| 2.3 Ustilaginomycetes | | | | | |
| *Malassezia furfur* | Mala f 2 | MF1, peroxisomal membrane protein | 21 | C | AB011804, 90 |

-continued

ALLERGENS

| Species Name | Allergen Name | Biochem. ID or Obsolete name | MW | cDNA (C) or protein (P) | Reference, Acc. No. |
|---|---|---|---|---|---|
| | Mala f 3 | MF2, peroxisomal membrane protein | 20 | C | AB011805, 90 |
| | Mala f 4 | mitochondrial malate dehydrogenase | 35 | C | AF084828, 90A |
| *Malassezia sympodialis* | Mala s 1 | | | C | X96486, 91 |
| | Mala s 5 | | 18* | C | AJ011955 |
| | Mala s 6 | | 17* | C | AJ011956 |
| | Mala s 7 | | | C | AJ011957, 91A |
| | Mala s 8 | | 19* | C | AJ011958, 91A |
| | Mala s 9 | | 37* | C | AJ011959, 91A |
| | Mala s 10 | heat shock prot. 70 | 86 | C | AJ428052 |
| | Mala s 11 | Mn superoxide dismut. | 23 | C | AJ548421 |
| 3. Deuteromycotina | | | | | |
| 3.1 Tuberculariales | | | | | |
| *Epicoccum purpurascens* (formerly *E. nigrum*) | Epi p 1 | serine protease | 30 | P | SW: P83340, 91B |
| G. Insects | | | | | |
| *Aedes aegyptii* | Aed a 1 | apyrase | 68 | C | L12389 |
| mosquito | Aed a 2 | | 37 | C | M33157 |
| *Apis mellifera* | Api m 1 | phospholipase A2 | 16 | C | 92 |
| honey bee | Api m 2 | hyaluronidase | 44 | C | 93 |
| | Api m 4 | melittin | 3 | C | 94 |
| | Api m 6 | | 7-8 | P | Kettner p.c. |
| | Api m 7 | CUB serine protease | 39 | C | AY127579 |
| *Bombus pennsylvanicus* | Bom p 1 | phospholipase | 16 | P | 95 |
| bumble bee | Bom p 4 | protease | | P | 95 |
| *Blattella germanica* | Bla g 1 | Bd90k | | C | |
| German cockroach | Bla g 2 | aspartic protease | 36 | C | 96 |
| | Bla g 4 | calycin | 21 | C | 97 |
| | Bla g 5 | glutathione transferase | 22 | C | 98 |
| | Bla g 6 | troponin C | 27 | C | 98 |
| *Periplaneta americana* | Per a 1 | Cr-PII | | C | |
| American cockroach | Per a 3 | Cr-PI | 72-78 | C | 98A |
| | Per a 7 | tropomyosin | 37 | C | Y14854 |
| *Chironomus kiiensis* midge | Chi k 10 | tropomyosin | 32.5* | C | AJ012184 |
| *Chironomus thummi thummi* midge | Chi t 1-9 | hemoglobin | 16 | C | 99 |
| | Chi t 1.01 | component III | 16 | C | P02229 |
| | Chi t 1.02 | component IV | 16 | C | P02230 |
| | Chi t 2.0101 | component I | 16 | C | P02221 |
| | Chi t 2.0102 | component IA | 16 | C | P02221 |
| | Chi t 3 | component II-beta | 16 | C | P02222 |
| | Chi t 4 | component IIIA | 16 | C | P02231 |
| | Chi t 5 | component VI | 16 | C | P02224 |
| | Chi t 6.01 | component VIIA | 16 | C | P02226 |
| | Chi t 6.02 | component IX | 16 | C | P02223 |
| | Chi t 7 | component VIIB | 16 | C | P02225 |
| | Chi t 8 | component VIII | 16 | C | P02227 |
| | Chi t 9 | component X | 16 | C | P02228 |
| *Ctenocephalides felis felis* | Cte f 1 | | | | |
| cat flea | Cte f 2 | M1b | 27 | C | AF231352 |
| | Cte f 3 | | 25 | C | |
| *Thaumetopoea pityocampa* pine processionary moth | Tha p 1 | | 15 | P | PIR: A59396, 99A |
| *Lepisma saccharina* silverfish | Lep s 1 | tropomyosin | 36 | C | AJ309202 |
| *Dolichovespula maculata* | Dol m 1 | phospholipase A1 | 35 | C | 100 |
| white face hornet | Dol m 2 | hyaluronidase | 44 | C | 101 |
| | Dol m 5 | antigen 5 | 23 | C | 102, 103 |
| *Dolichovespula arenaria* yellow hornet | Dol a 5 | antigen 5 | 23 | C | 104 |
| *Polistes annularies* | Pol a 1 | phospholipase A1 | 35 | P | 105 |
| wasp | Pol a 2 | hyaluronidase | 44 | P | 105 |
| | Pol a 5 | antigen 5 | 23 | C | 104 |
| *Polistes dominulus* | Pol d 1 | | | | Hoffman p.c. |
| Mediterranean paper wasp | Pol d 4 | serine protease | 32-34 | C | Hoffman p.c. |
| | Pol d 5 | | | | P81656 |
| *Polistes exclamans* | Pol e 1 | phospholipase A1 | 34 | P | 107 |
| wasp | Pol e 5 | antigen 5 | 23 | C | 104 |
| *Polistes fuscatus* wasp | Pol f 5 | antigen 5 | 23 | C | 106 |

-continued

ALLERGENS

| Species Name | Allergen Name | Biochem. ID or Obsolete name | MW | cDNA (C) or protein (P) | Reference, Acc. No. |
|---|---|---|---|---|---|
| *Polistes gallicus* wasp | Pol g 5 | antigen 5 | 24 | C | P83377 |
| *Polistes metricus* wasp | Pol m 5 | antigen 5 | 23 | C | 106 |
| *Vespa crabo* European hornet | Vesp c 1 | phospholipase | 34 | P | 107 |
|  | Vesp c 5 | antigen 5 | 23 | C | 106 |
| *Vespa mandarina* giant asian hornet | Vesp m 1 |  |  |  | Hoffman p.c. |
|  | Vesp m 5 |  |  |  | P81657 |
| *Vespula flavopilosa* yellowjacket | Ves f 5 | antigen 5 | 23 | C | 106 |
| *Vespula germanica* yellowjacket | Ves g 5 | antigen 5 | 23 | C | 106 |
| *Vespula maculifrons* yellowjacket | Ves m 1 | phospholipase A1 | 33.5 | C | 108 |
|  | Ves m 2 | hyaluronidase | 44 | P | 109 |
|  | Ves m 5 | antigen 5 | 23 | C | 104 |
| *Vespula pennsylvanica* yellowjacket | Ves p 5 | antigen 5 | 23 | C | 106 |
| *Vespula squamosa* yellowjacket | Ves s 5 | antigen 5 | 23 | C | 106 |
| *Vespula vidua* wasp | Ves vi 5 | antigen 5 | 23 | C | 106 |
| *Vespula vulgaris* yellowjacket | Ves v 1 | phospholipase A1 | 35 | C | 105A |
|  | Ves v 2 | hyaluronidase | 44 | P | 105A |
|  | Ves v 5 | antigen 5 | 23 | C | 104 |
| *Myrmecia pilosula* Australian jumper ant | Myr p 1 |  |  | C | X70256 |
|  | Myr p 2 |  |  | C | S81785 |
| *Solenopsis geminata* tropical fire ant | Sol g 2 |  |  |  | Hoffman p.c. |
|  | Sol g 4 |  |  |  | Hoffman p.c. |
| *Solenopsis invicta* fire ant | Sol i 2 |  | 13 | C | 110, 111 |
|  | Sol i 3 |  | 24 | C | 110 |
|  | Sol i 4 |  | 13 | C | 110 |
| *Solenopsis saevissima* Brazilian fire ant | Sol s 2 |  |  |  | Hoffman p.c. |
| *Triatoma protracta* California kissing bug | Tria p 1 | Procalin | 20 | C | AF179004, 111A. |
| H. Foods |  |  |  |  |  |
| *Gadus callarias* cod | Gad c 1 | allergen M | 12 | C | 112, 113 |
| *Salmo salar* Atlantic salmon | Sal s 1 | parvalbumin | 12 | C | X97824 |
| *Bos domesticus* domestic cattle (milk) see also animals | Bos d 4 | alpha-lactalbumin | 14.2 | C | M18780 |
|  | Bos d 5 | beta-lactoglobulin | 18.3 | C | X14712 |
|  | Bos d 6 | serum albumin | 67 | C | M73993 |
|  | Bos d 7 | immunoglobulin | 160 |  | 77 |
|  | Bos d 8 | caseins | 20-30 |  | 77 |
| *Cyprinus carpio* (Common carp) | Cyp c 1 | parvalbumin | 12 | C | 129 |
| *Gallus domesticus* chicken | Gal d 1 | ovomucoid | 28 | C | 114, 115 |
|  | Gal d 2 | ovalbumin | 44 | C | 114, 115 |
|  | Gal d 3 | Ag22, conalbumin | 78 | C | 114, 115 |
|  | Gal d 4 | lysozyme | 14 | C | 114, 115 |
|  | Gal d 5 | serum albumin | 69 | C | X60688 |
| *Metapenaeus ensis* shrimp | Met e 1 | tropomyosin |  | C | U08008 |
| *Penaeus aztecus* shrimp | Pen a 1 | tropomyosin | 36 | P | 116 |
| *Penaeus indicus* shrimp | Pen i 1 | tropomyosin | 34 | C | 116A |
| *Penaeus monodon* black tiger shrimp | Pen m 1 | tropomyosin | 38 | C |  |
|  | Pen m 2 | arginine kinase | 40 | C | AF479772, 117 |
| *Todarodes pacificus* squid | Tod p 1 | tropomyosin | 38 | P | 117A |
| *Helix aspersa* brown garden snail | Hel as 1 | tropomyosin | 36 | C | Y14855, 117B |
| *Haliotis midae* abalone | Hal m 1 |  | 49 |  | 117C |
| *Rana esculenta* edible frog | Ran e 1 | parvalbumin alpha | 11.9* | C | AJ315959 |
|  | Ran e 2 | parvalbumin beta | 11.7* | C | AJ414730 |
| *Brassica juncea* oriental mustard | Bra j 1 | 2S albumin | 14 | C | 118 |

ALLERGENS

| Species Name | Allergen Name | Biochem. ID or Obsolete name | MW | cDNA (C) or protein (P) | Reference, Acc. No. |
|---|---|---|---|---|---|
| *Brassica napus* rapeseed | Bra n 1 | 2S albumin | 15 | P | 118A, P80208 |
| *Brassica rapa* turnip | Bra r 2 | hom: prohevein | 25 | | P81729 |
| *Hordeum vulgare* barley | Hor v 15 | BMAI-1 | 15 | C | 119 |
| | Hor v 16 | alpha-amylase | | | |
| | Hor v 17 | beta-amylase | | | |
| | Hor v 21 | gamma-3 hordein | 34 | C | 119A, SW: P80198 |
| *Secale cereale* rye | Sec c 20 | secalin | | | see isoall. list |
| *Triticum aestivum* wheat | Tri a 18 | agglutinin | | | |
| | Tri a 19 | omega-5 gliadin | 65 | P | PIR: A59156 |
| *Zea mays* maise, corn | Zea m 14 | lipid transfer prot. | 9 | P | P19656 |
| *Oryza sativa* rice | Ory s 1 | | | C | 119B, U31771 |
| *Apium graveolens* celery | Api g 1 | hom: Bet v 1 | 16* | C | Z48967 |
| | Api g 4 | profilin | | | AF129423 |
| | Api g 5 | | 55/58 | P | P81943 |
| *Daucus carota* carrot | Dau c 1 | hom: Bet v 1 | 16 | C | 117D, see isoallergen list |
| | Dau c 4 | profilin | | C | AF456482 |
| *Corylus avellana* hazelnut | Cor a 1.04 | hom: Bet v 1 | 17 | C | see list of isoallergens |
| | Cor a 2 | profilin | 14 | C | AF327622 |
| | Cor a 8 | lipid transfer protein | 9 | C | AF329829 |
| *Malus domestica* apple | Mal d 1 | hom: Bet v 1 | | C | see list of isoallergens |
| | Mal d 2 | hom: thaumatin | | C | AJ243427 |
| | Mal d 3 | lipid transfer protein | 9 | C | Pastorello p.c. |
| | Mal d 4 | profilin | 14.4* | C | see list of isoallergens |
| *Pyrus communis* pear | Pyr c 1 | hom: Bet v 1 | 18 | C | AF05730 |
| | Pyr c 4 | profilin | 14 | C | AF129424 |
| | Pyr c 5 | hom: isoflavone reductas | 33.5 | C | AF071477 |
| *Persea americana* avocado | Pers a 1 | endochitinase | 32 | C | Z78202 |
| *Prunus armeniaca* apricot | Pru ar 1 | hom: Bet v 1 | | C | U93165 |
| | Pru ar 3 | lipid transfer protein | 9 | P | |
| *Prunus avium* sweet cherry | Pru av 1 | hom: Bet v 1 | | C | U66076 |
| | Pru av 2 | hom: thaumatin | | C | U32440 |
| | Pru av 3 | lipid transfer protein | 10 | C | AF221501 |
| | Pru av 4 | profilin | 15 | C | AF129425 |
| *Prunus domestica* European plum | Pru d 3 | lipid transfer protein | 9 | P | 119C |
| *Prunus persica* peach | Pru p 3 | lipid transfer protein | 10 | P | P81402 |
| | Pru p 4 | profilin | 14 | C | see isoallergen list |
| *Asparagus officinalis* Asparagus | Aspa o 1 | lipid transfer protein | 9 | P | 119D |
| *Crocus sativus* saffron crocus | Cro s 1 | | 21 | | Varasteh A-R p.c. |
| *Lactuca sativa* lettuce | Lac s 1 | lipid transfer protein | 9 | | Vieths p.c. |
| *Vitis vinifera* grape | Vit v 1 | lipid transfer protein | 9 | P | P80274 |
| *Musa* x *paradisiaca* banana | Mus xp 1 | profilin | 15 | C | AF377948 |
| *Ananas comosus* pineapple | Ana c 1 | profilin | 15 | C | AF377949 |
| | Ana c 2 | bromelain | 22.8* | C | 119E-G, D14059 |
| *Citrus limon* lemon | Cit l 3 | lipid transfer protein | 9 | P | Torrejon p.c. |
| *Citrus sinensis* sweet orange | Cit s 1 | germin-like protein | 23 | P | Torrejon p.c. |
| | Cit s 2 | profilin | 14 | P | Torrejon p.c. |
| | Cit s 3 | lipid transfer protein | 9 | P | Torrejon p.c. |
| *Litchi chinensis* litchi | Lit c 1 | profilin | 15 | C | AY049013 |
| *Sinapis alba* yellow mustard | Sin a 1 | 2S albumin | 14 | C | 120 |
| *Glycine max* soybean | Gly m 1 | HPS | 7 | P | 120A |
| | Gly m 2 | | 8 | P | A57106 |
| | Gly m 3 | profilin | 14 | C | see list of isoallergens |
| | Gly m 4 | (SAM22) PR-10 prot. | 17 | C | X60043, 120B |
| *Vigna radiata* mung bean | Vig r 1 | PR-10 protein | 15 | C | AY792956 |

ALLERGENS

| Species Name | Allergen Name | Biochem. ID or Obsolete name | MW | cDNA (C) or protein (P) | Reference, Acc. No. |
|---|---|---|---|---|---|
| *Arachis hypogaea* | Ara h 1 | vicilin | 63.5 | C | L34402 |
| peanut | Ara h 2 | conglutin | 17 | C | L77197 |
| | Ara h 3 | glycinin | 60 | C | AF093541 |
| | Ara h 4 | glycinin | 37 | C | AF086821 |
| | Ara h 5 | profilin | 15 | C | AF059616 |
| | Ara h 6 | hom: conglutin | 15 | C | AF092846 |
| | Ara h 7 | hom: conglutin | 15 | C | AF091737 |
| | Ara h 8 | PR-10 protein | 17 | C | AY328088 |
| *Lens culinaris* | Len c 1 | vicilin | 47 | C | see list of isoallergens |
| lentil | Len c 2 | seed biotinylated prot. | 66 | P | 120C |
| *Pisum savitum* | Pis s 1 | vicilin | 44 | C | see list of isoallergens |
| pea | Pis s 2 | convicilin | 63 | C | pending |
| *Actinidia chinensis* | Act c 1 | cysteine protease | 30 | P | P00785 |
| kiwi | Act c 2 | thaumatin-like protein | 24 | P | SW: P81370, 121 |
| *Capsicum annuum* | Cap a 1w | osmotin-like protein | 23 | C | AJ297410 |
| bell pepper | Cap a 2 | profilin | 14 | C | AJ417552 |
| *Lycopersicon esculentum* | Lyc e 1 | profilin | 14 | C | AJ417553 |
| tomato | Lyc e 2 | b-fructofuranosidase | 50 | C | see isoallergen list |
| | Lyc e 3 | lipid transfer prot. | 6 | C | U81996 |
| *Solanum tuberosum* | Sola t 1 | patatin | 43 | P | P15476 |
| potato | Sola t 2 | cathepsin D inhibitor | 21 | P | P16348 |
| | Sola t 3 | cysteine protease inhibitor | 21 | P | P20347 |
| | Sola t 4 | aspartic protease inhibitor | 16 + 4 | P | P30941 |
| *Bertholletia excelsa* | Ber e 1 | 2S albumin | 9 | C | P04403, M17146 |
| Brazil nut | Ber e 2 | 11S globulin seed storage protein | 29 | C | AY221641 |
| *Juglans nigra* | Jug n 1 | 2S albumin | 19* | C | AY102930 |
| black walnut | Jug n 2 | vicilin-like prot. | 56* | C | AY102931 |
| *Juglans regia* | Jug r 1 | 2S albumin | | C | U66866 |
| English walnut | Jug r 2 | vicilin | 44 | C | AF066055 |
| | Jug r 3 | lipid transfer protein | 9 | P | Pastorello |
| *Anacardium occidentale* | Ana o 1 | vicilin-like protein | 50 | C | see isoallergen list |
| Cashew | Ana o 2 | legumin-like protein | 55 | C | AF453947 |
| | Ana o 3 | 2S albumin | 14 | C | AY081853 |
| *Ricinus communis* | Ric c 1 | 2S albumin | | C | P01089 |
| Castor bean | | | | | |
| *Sesamum indicum* | Ses i 1 | 2S albumin | 9 | C | 121A, AF240005 |
| sesame | Ses i 2 | 2S albumin | 7 | C | AF091841 |
| | Ses i 3 | 7S vicilin-like globulin | 45 | C | AF240006 |
| | Ses i 4 | oleosin | 17 | C | AAG23840 |
| | Ses i 5 | oleosin | 15 | C | AAD42942 |
| *Cucumis melo* | Cuc m 1 | serine protease | 66 | C | D32206 |
| muskmelon | Cuc m 2 | profilin | 14 | C | AY271295 |
| | Cuc m 3 | pathogenesis-rel p. PR-1 | 16* | P | P83834 |
| I. Others | | | | | |
| *Anisakis simplex* | Ani s 1 | | 24 | P | 121B, A59069 |
| nematode | Ani s 2 | paramyosin | 97 | C | AF173004 |
| | Ani s 3 | tropomyosin | 41 | C | 121C, Y19221 |
| | Ani s 4 | | 9 | P | P83885 |
| *Argas reflexus* | Arg r 1 | | 17 | C | AJ697694 |
| pigeon tick | | | | | |
| *Ascaris suum* | Asc s 1 | | 10 | P | 122 |
| worm | | | | | |
| *Carica papaya* | Car p 3w | papain | 23.4* | C | 122A, M15203 |
| papaya | | | | | |
| *Dendronephthya nipponica* | Den n 1 | | 53 | P | 122B |
| soft coral | | | | | |
| *Hevea brasiliensis* | Hev b 1 | elongation factor | 58 | P | 123, 124 |
| rubber (latex) | Hev b 2 | 1,3-glucanase | 34/36 | C | 125 |
| | Hev b 3 | | 24 | P | 126, 127 |
| | Hev b 4 | component of microhelix complex | 100-115 | P | 128 |
| | Hev b 5 | | 16 | C | U42640 |
| | Hev b 6.01 | hevein precursor | 20 | C | M36986, p02877 |
| | Hev b 6.02 | hevein | 5 | C | M36986, p02877 |
| | Hev b 6.03 | C-terminal fragment | 14 | C | M36986, p02877 |
| | Hev b 7.01 | hom: patatin from B-serum | 42 | C | U80598 |
| | Hev b 7.02 | hom: patatin from C-serum | 44 | C | AJ223038 |
| | Hev b 8 | profilin | 14 | C | see list of isoallergens |
| | Hev b 9 | enolase | 51 | C | AJ132580 |
| | Hev b 10 | Mn superoxide dismut. | 26 | C | see list of isoallergens |
| | Hev b 11 | class 1 chitinase | | C | see list of isoallergens |

ALLERGENS

| Species Name | Allergen Name | Biochem. ID or Obsolete name | MW | cDNA (C) or protein (P) | Reference, Acc. No. |
|---|---|---|---|---|---|
| | Hev b 12 | lipid transfer protein | 9.3 | C | AY057860 |
| | Hev b 13 | esterase | 42 | P | P83269 |
| Homo sapiens | Hom s 1 | | 73* | C | Y14314 |
| human autoallergens | Hom s 2 | | 10.3* | C | X80909 |
| | Hom s 3 | | 20.1* | C | X89985 |
| | Hom s 4 | | 36* | C | Y17711 |
| | Hom s 5 | | 42.6* | C | P02538 |
| Triplochiton scleroxylon obeche | Trip s 1 | class 1 chitinase | 38.5 | P | Kespohl p.c. |

REFERENCES

1 Marsh, D. G., and L. R. Freidhoff. 1992. ALBE, an allergen database. IUIS, Baltimore, Md., Edition 1.0.
2 Marsh, D. G. et al. 1986. Allergen nomenclature. Bull WHO 64:767-770.
3 King, T. P. et al. 1964. Biochemistry 3:458-468.
4 Lowenstein, H. 1980. Allergy 35:188-191.
5 Aukrust, L. 1980. Allergy 35:206-207.
6 Demerec, M. et al. 1966. Genetics 54:61-75.
7 Bodmer, J. G. et al. 1991. Immunogenetics 33:301-309.
8 Griffith, I. J. et al. 1991. Int. Arch. Allergy Appl. Immunol. 96:296-304.
9 Roebber, M. et al. 1985. J. Immunol. 134:3062-3069.
10 Metzler, W. J. et al. 1992. Biochemistry 31:5117-5127.
11 Metzler, W. J. et al. 1992. Biochemistry 31:8697-8705.
12 Goodfriend, L. et al. 1979. Fed. Proc. 38:1415.
13 Ekramoddoullah, A. K. M. et al. 1982. Mol. Immunol. 19:1527-1534.
14 Ansari, A. A. et al. 1987. J. Allergy Clin. Immunol. 80:229-235.
15 Morgenstern, J. P. et al. 1991. Proc. Natl. Acad. Sci. USA 88:9690-9694.
16 Griffith, I. J. et al. 1992. Gene 113:263-268.
17 Weber, A. et al. 1986. Biochem. Physiol. 83B:321-324.
18 Weber, A. et al. 1987. Allergy 42:464-470.
19 Stanworth, D. R. et al. 1990. Bulletin WHO 68:109-111.
20 Rafnar, T. et al. 1991. J. Biol. Chem. 266: 1229-1236.
21 Rogers, B. L. et al. 1991. J. Immunol. 147:2547-2552.
22 Klapper, D. G. et al. 1980. Biochemistry 19:5729-5734.
23 Ghosh, B. et al. 1993. J. Immunol. 150:5391-5399.
24 Roebber, M. et al. 1983. J. Immunol. 131:706-711.
25 Lubahn, B., and D. G. Klapper. 1993. J. Allergy Clin. Immunol. 91:338.
26 Roebber, M., and D. G. Marsh. 1991. J. Allergy Clin. Immunol. 87:324.
27 Goodfriend L. et al. Mol Immunol 22: 899-906, 1985.
28 Himly M. et al. FASEB J 17: 106-108, 2003.
28A Nilsen, B. M. et al. 1991. J. Biol. Chem. 266:2660-2668.
29 Wopfner N. et al. Biol Chem 383: 1779-1789, 2002.
29A Jimenez A. et al. 1994. Int Arch Allergy Immunol 105: 297-307.
29B Barderas R. et al. Int Arch Allergy Immunol 127: 47-54, 2002.
29C Carnés J. et al. Allergy 56, Supplement 68: 274, 2001.
29D Giuliani A. et al. Allergy 42: 434-440, 1987.
30 Smith, P. M. et al. 1996. J. Allergy Clin. Immunol. 98:331-343.
31 Suphioglu, C. et al. 1997. FEBS Lett. 402:167-172.
31a Asturias J. A. et al. 1997. Clin Exp Allergy 27:1307-1313.
32 Mecheri, S. et al. 1985. Allergy Appl. Immunol. 78:283-289.
33 Roberts, A. M. et al. 1993. Allergy 48:615-623.
33a Guerin-Marchand, C. et al. 1996. Mol. Immunol. 33:797-806.
34 Klysner, S. et al. 1992. Clin. Exp. Allergy 22: 491-497.
35 Perez, M. et al. 1990. J. Biol. Chem. 265:16210-16215.
36 Griffith, I. J. et al. 1991. FEBS Letters 279:210-215.
37 Ansari, A. A. et al. 1989. J. Biol. Chem. 264:11181-11185.
37a Sidoli, A. et al. 1993. J. Biol. Chem. 268:21819-21825.
38 Ansari, A. A. et al. 1989. Biochemistry 28:8665-8670.
39 Singh, M. B. et al. 1991. Proc. Natl. Acad. Sci. 88:1384-1388.
39a van Ree R. et al. 1995. J Allergy Clin Immunol 95:970-978.
40 Suphioglu, C. and Singh, M. B. 1995. Clin. Exp. Allergy 25:853-865.
41 Dolecek, C. et al. 1993. FEBS Lett. 335:299-304.
41A Fischer S. et al. 1996. J Allergy Clin Immunol 98:189-198.
42 Matthiesen, F., and H. Lowenstein. 1991. Clin. Exp. Allergy 21:297-307.
43 Petersen, A. et al. 1995. Int. Arch. Allergy Immunol. 108: 55-59.
43A Marknell DeWitt A. et al. Clin Exp Allergy 32: 1329-1340, 2002.
44 Valenta, R. et al. 1994. Biochem. Biophys. Res. Commun. 199:106-118.
46 Esch, R. E., and D. G. Klapper. 1989. Mol. Immunol. 26:557-561.
47 Olsen, E. et al. 1991. J. Immunol. 147:205-211.
48 Avjioglu, A. et al. 1993. J. Allergy Clin. Immunol. 91:340.
52 Kos T. et al. 1993. Biochem Biophys Res Commun 196: 1086-92.
53 Díaz-Perales A. et al. 2000. Clin Exp Allergy 30:1403-1410.
54 Ipsen, H., and O. C. Hansen. 1991. Mol. Immunol. 28: 1279-1288.
55 Taniai, M. et al. 1988. FEBS Lett. 239:329-332.
56 Griffith, I. J. et al. 1993. J. Allergy Clin. Immunol. 91:339.
57 Sakaguchi, M. et al. Allergy 45: 309-312, 1990.
57A Yokoyama M. et al. Biochem Biophys Res Commun 275: 195-202, 2000.
57B Midoro-Horiuti T. et al. J Immunol 164: 2188-2192, 2000.
57C Tinghino R. et al. J. Allergy Clin. Immunol. 101: 772-777, 1998.
58 Gross G N et al. Scand J Immunol 8: 437-441, 1978.

58A Obispo T M et al. Clin Exp Allergy 23: 311-316, 1993.
58B Midoro-Horiuti T. et al. Clin Exp Allergy 31: 771-778, 2001.
59 Lombardero M. et al. Clin. Exp. Allergy 24: 765-770, 1994.
60 Villalba, M. et al. Eur. J. Biochem. 216: 863-869, 1993.
60A Asturias J A et al. J Allergy Clin Immunol 100: 365-372, 1997.
60B Batanero E. et al. Eur J Biochem 241: 772-778, 1996.
60C Batanero E. et al. FEBS Lett. 410: 293-296, 1997.
60D Tejera M L et al. J Allergy Clin Immunol 104: 797-802, 1999.
60E Ledesma A. et al. FEBS Lett 466: 192-196, 2000.
60F Barral P. et al. J Immunol 172: 3644-3651, 2004.
61 Yi F C et al. Clin Exp Allergy 32: 1203-1210, 2002.
61A Ramos J D et al. Int Arch Allergy Immunol 126: 286-293, 2001.
62 Chua, K. Y. et al. J. Exp. Med. 167: 175-182, 1988.
62A Chua, K. Y. et al. Int. Arch. Allergy Appl. Immunol. 91: 118-123, 1990.
62B Smith A M et al. Int Arch Allergy Immunol 124: 61-63, 2001.
62C Smith A M et al. J Allergy Clin Immunol 107: 977-984, 2001.
63 Smith W A, Thomas W R. Int Arch Allergy Immunol 109: 133-140, 1996.
64 Lake, F. R. et al. J. Allergy Clin. Immunol. 87: 1035-1042, 1991.
65 Tovey, E. R. et al. J. Exp. Med. 170: 1457-1462, 1989.
66 Yasueda, H., T. Shida, T. Ando, S. Sugiyama, and H. Yamakawa. 1991. Allergenic and proteolytic properties of fourth allergens from *Dermatophagoides* mites. In: "Dust Mite Allergens and Asthma. Report of the 2nd international workshop" A. Todt, Ed., UCB Institute of Allergy, Brussels, Belgium, pp. 63-64.
67 Shen, H.-D. et al. Clin. Exp. Allergy 23: 934-940, 1993.
67A O'Neil G M et al. Biochim Biophys Acta, 1219: 521-528, 1994.
67B King C. et al. J Allergy Clin Immunol 98: 739-747, 1996.
68 Lind P. et al. J. Immunol. 140: 4256-4262, 1988.
69 Dilworth, R. J. et al. Clin. Exp. Allergy 21: 25-32, 1991.
70 Nishiyama, C. et al. Int. Arch. Allergy Immunol. 101: 159-166, 1993.
70A Trudinger, M. et al. Clin. Exp. Allergy 21: 33-38, 1991.
71 Shen H D et al. Clin Exp Allergy 25: 1000-1006, 1995.
71A Tategaki A. et al. ACI International suppl. 1: 74-76, 2000.
72 Aki T. et al. J Allergy Clin Immunol 96: 74-83, 1995.
72A Tsai L. et al. Clin Exp Allergy 29: 1606-1613, 1999.
72B Gafvelin G. et al. J Allergy Clin Immunol 107: 511-518, 2001.
73 van Hage-Hamsten. et al. J. Allergy Clin. Immunol. 91:353, 1993.
74 Varela J. et al. Eur J Biochem 225: 93-98, 1994.
74A Schmidt M. et al. FEBS Lett 370: 11-14, 1995.
75 Eriksson T L J et al. Eur. J. Biochem. 268: 287-294, 2001.
75A Saarne T. et al. Int Arch Allergy Immunol 130: 258-265, 2003.
75B Eriksson T L et al. Eur. J. Biochem. 251 (1-2), 443-447, 1998.
76 Rautiainen J, Rytkonen M, Pelkonen A, Pentikainen J, Perola O, Virtanen T, Zeiler T, Mantyjarvi R. BDA20, a major bovine dander allergen characterised at the sequence level is Bos d 2. Submitted.
77 Gjesing B, Lowenstein H. Ann Allergy 53:602, 1984.
78 de Groot, H. et al. J. Allergy Clin. Immunol. 87:1056-1065, 1991.
79 Konieczny, A. Personal communication; Immunologic Pharmaceutical Corp.
79A Bulone, V. Eur J Biochem 253: 202-211, 1998.
79B Swiss-Prot acc. P81216, P81217.
79C Dandeu J. P. et al. (1993). J. Chromatogr. 621:23-31.
79D Goubran Botros H. et al. 1998. J. Chromatogr. B 710: 57-65.
79E Hilger C. et al. Allergy 52: 179-187; and Hilger C. et al. Gene 169:295-296, 1996.
79F Ichikawa K. et al. Clin Exp Allergy, In Press 2001.
80 Fahlbusch B. et al. Allergy 57: 417-422, 2002.
81 McDonald, B. et al. 1988. J. Allergy Clin. Immunol. 83:251.
81A Clarke, A. J. et al. 1984. EMBO J 3:1045-1052.
82 Longbottom, J. L. 1983. Characterisation of allergens from the urines of experimental animals. McMillan Press, London, pp. 525-529.
83 Laperche, Y. et al. 1983. Cell 32:453-460.
83A Bush R K et al. 1999. J Allergy Clin Immunol 104:665-671.
83B Aukrust L, Borch S M. 1979. Int Arch Allergy Appl Immunol 60:68-79.
83C Sward-Nordmo M. et al. 1988. Int Arch Allergy Appl Immunol 85:288-294.
84 Shen, et al. J. Allergy Clin. Immunol. 103:S157, 1999.
84A Crameri R. Epidemiology and molecular basis of the involvement of *Aspergillus fumigatus* in allergic diseases. Contrib. Microbiol. Vol. 2, Karger, Basel (in press).
84B Shen, et al. (manuscript submitted), 1999
84C Shen H D et al. Vacuolar serine proteinase: A major allergen of *Aspergillus fumigatus*. 10th International Congress of Immunology, Abstract, 1998.
85 Kumar A. et al. 1993. J. Allergy Clin. Immunol. 91:1024-1030.
85A Saxena S. et al. 2003. Clin Exp Immunol 134:86-91.
85B Baur X. et al. Allergy 57: 943-945, 2002.
86A Shen H D et al. 1996. Clin Exp Allergy 26:444-451.
86B Shen, et al. Abstract; The XVIII Congress of the European Academy of Allergology and Clinical Immunology, Brussels, Belgium, 3-7 Jul. 1999.
87 Shen H D et al. Clin Exp Allergy 29: 642-651, 1999.
87A Shen H D et al. Clin Exp Allergy 25: 350-356, 1995.
87B Shen H D et al. J Lab Clin Med 137: 115-124, 2001.
88 Woodfolk J A et al. 1998. J Biol Chem 273:29489-96.
88A Deuell, B. et al. 1991. J. Immunol. 147:96-101.
89 Shen, H. D. et al. 1991. Clin. Exp. Allergy 21:675-681.
89A Horner W E et al. 1995. Int Arch Allergy Immunol 107:298-300.
89B Chang C Y et al. J Biomed Sci 9: 645-655, 2002.
90 Yasueda H. et al. Biochem Biophys Res Commun 248: 240-244, 1998. NB: strain TIMM2782 (Teikyo University Institute for Medical Mycology) equal to strain CBS1878 (Central Bureau von Schimmelkulturen).
90A Onishi Y. et al. Eur J Biochem 261: 148-154, 1999. NB: strain TIMM2782 (Teikyo University Institute for Medical Mycology) equal to strain CBS1878 (Central Bureau von Schimmelkulturen).
91 Schmidt M. et al. Eur J Biochem 246:181-185, 1997. NB: strain ATCC no. 42132 (American Type Culture Collection).
91A Rasool O. et al. Eur J Biochem 267: 4355-4361, 2000. NB: strain ATCC no. 42132 (American Type Culture Collection).
91B NB: strain 4625 (Indian Agricultural Research Institute, PUSA; New Delhi, India).
92 Kuchler, K. et al. 1989. Eur. J. Biochem. 184:249-254.

93 Gmachl, M., and G. Kreil. 1993. Proc. Natl. Acad. Sci. USA 90:3569-3573.
93A Hoffman D R. 1977. J. Allergy Clin. Immunol. 59:364-366.
94 Habermann, E. 1972. Science 177:314-322.
95 Hoffman D R, Jacobson R S. 1996. J. Allergy Clin. Immunol. 97:812-821.
95A Hoffman D R, El-Choufani A E, Smith M M, de Groot H. 2001. Occupational allergy to bumblebee venom: Allergens of *Bombus terrestris*. J Allergy Clin Immunol In press.
95B Helm R. et al. 1996. J Allerg Clin Immunol 98:172-180.
95C Pomes A. et al. 1998. J Biol Chem 273:30801-30807.
96 Arruda L K et al. J Biol Chem 270:19563-19568, 1995.
97 Arruda L K et al. J Biol Chem 270:31196-31201, 1995.
98 Arruda L K et al. Int Arch Allergy Immunol 107:295-297, 1995.
98A Wu C H et al. 1998. J Allergy Clin Immunol 101:832-840.
98B Melen E. et al. 1999. J Allergy Clin Immunol 103:859-64.
98C Wu C H et al. J Biol Chem 271:17937-17943, 1996.
98D Wu C H et al. Molecular Immunol 34:1-8, 1997.
98E Santos A B R et al. 1999. J Allergy Clin Immunol 104:329-337.
98F Asturias J A et al. 1999. J Immunol 162:4342-4348.
99 Mazur, G. et al. 1990. Monog. Allergy 28:121-137.
99A Moneo I. et al. Allergy 58: 34-37, 2003.
100 Soldatova, L. et al. 1993. FEBS Letters 320:145-149.
101 Lu, G. et al. 1994. J. Allergy Clin. Immunol. 93:224.
102 Fang, K. S. F. et al. 1988. Proc. Natl. Acad. Sci., USA 85:895-899.
103 King, T. P. et al. 1990. Prot. Seq. Data Anal. 3:263-266.
104 Lu, G. et al. 1993. J. Immunol. 150: 2823-2830.
105 King, T. P. and Lu, G. 1997. Unpublished data.
105A King T P et al. 1996. J. Allergy Clin. Immunol. 98:588-600.
106 Hoffman, D. R. 1993. J. Allergy Clin. Immunol. 92:707-716.
107 Hoffman D R. 1992. Unpublished data.
108 Hoffman D R. J. Allergy Clin. Immunol. 91:187, 1993.
109 Jacobson R S et al. J. Allergy Clin. Immunol. 89:292, 1992.
110 Hoffman D R. J. Allergy Clin. Immunol 91: 71-78, 1993.
111 Schmidt M. et al. FEBS Letters 319: 138-140, 1993.
111A Paddock C D et al. J Immunol 167: 2694-2699, 2001.
112 Elsayed S, Bennich H. Scand J Immunol 3: 683-686, 1974.
113 Elsayed S. et al. Immunochemistry 9: 647-661, 1972.
114 Hoffman, D. R. 1983. J. Allergy Clin. Immunol. 71: 481-486.
115 Langeland, T. 1983. Allergy 38:493-500.
116 Daul C B, Slattery M, Morgan J E, Lehrer S B. 1993. Common crustacea allergens: identification of B cell epitopes with the shrimp specific monoclonal antibodies. In: "Molecular Biology and Immunology of Allergens" (D. Kraft and A. Sehon, eds.). CRC Press, Boca Raton. pp. 291-293.
116A Shanti K N et al. J. Immunol. 151: 5354-5363, 1993.
117 Yu C J et al. J Immunol 170: 445-453, 2003.
117A Miyazawa M et al. J. Allergy Clin. Immunol. 98: 948-953, 1996.
117B Asturias J A et al. Int Arch Allergy Immunol 128: 90-96, 2002.
117C Lopata A L et al. J. Allergy Clin. Immunol. 100: 642-648, 1997.
117D Hoffmann-Sommergruber K. et al. Clin. Exp. Allergy 29: 840-847, 1999.
118 Monsalve R I et al. Biochem. J. 293: 625-632 1993.
118A. Monsalve R I et al. 1997. Clin Exp Allergy 27:833-841.
119 Mena, M. et al. Plant Molec. Biol. 20: 451-458, 1992.
119A Palosuo K. et al. J. Allergy Clin. Immunol. 108: 634-638, 2001.
119B Xu H. et al. Gene 164: 255-259, 1995.
119C Pastorello E A et al. J. Allergy Clin. Immunol. 94: 699-707, 1994.
119D Diaz-Perales A. et al. J Allergy Clin Immunol 110: 790-796, 2002.
119E Galleguillos F, Rodriguez J C. Clin Allergy 8: 21-24, 1978.
119F Baur X. Clin Allergy 9: 451-457, 1979.
119G Gailhofer G. et al. Clin Allergy 18: 445-450, 1988.
120 Menendez-Arias, L. et al. 1988. Eur. J. Biochem. 177: 159-166.
120A Gonzalez R. et al. Lancet 346:48-49, 1995.
120B Kleine-Tebbe J. et al. J Allergy Clin Immunol 110: 797-804, 2002.
120C Sanchez-Monge R. et al. J. Allergy Clin. Immunol. 106: 955-961, 2000.
121 Gavrovic-Jankulovic M. et al. J Allergy Clin Immunol 110: 805-810, 2002.
121A Pastorello E A et al. J. Chromatogr. B Biomed. Sci. Appl. 756: 85-93, 2001.
121B Moneo I. et al. J. Allergy Clin. Immunol. 106: 177-182, 2000.
121C Asturias J A et al. 2000. Allergy 55:898-890.
122 Christie, J. F. et al. 1990. Immunology 69:596-602.
122A Baur X. et al. Clin Allergy 12: 9-17, 1982.
122B Onisuka R. et al. Int Arch Allergy Immunol 125: 135-143, 2001.
123 Czuppon A B et al. J Allergy Clin Immunol 92:690-697, 1993.
124 Attanayaka D P S T G et al. 1991. Plant Mol Biol 16:1079-1081.
125 Chye M L, Cheung K Y. 1995. Plant Mol Biol 26:397-402.
126 Alenius H. et al. 1993. Int Arch Allergy Immunol 102: 61-66.
127 Yeang H Y, Cheong K F, Sunderasan E, Hamzah S, Chew N P, Hamid S, Hamilton R G, Cardosa M J. 1996. The 14.6 kD (REF, Hev b 1) and 24 kD (Hev b 3) rubber particle proteins are recognised by IgE from Spina Bifida patients with Latex allergy. J Allerg Clin Immunol in press.
128 Sunderasan E. et al. 1995. J nat Rubb Res 10:82-99.
129 Swoboda I. et al. 2002. J Immunol. 168:4576-84.

According to a preferred embodiment of the present invention the hypoallergenic molecule exhibits reduced IgE-binding capacity.

According to another preferred embodiment of the present invention the hypoallergenic molecule exhibits reduced T-cell reactivity.

However, also allergen fragments comprising at least one T-cell epitope may be used in the hypoallergenic protein according to the present invention.

"Exhibiting reduced IgE-binding capacity", as used herein, means that the molecules according to the present invention show significantly reduced IgE-binding capacity or activity (at least 50% less, preferably at least 70% less, more preferably at least 80% less, even more preferably at least 90% less, most preferably at least 95% less, binding capacity compared to the wild-type allergen) or even lack them at all.

IgE-binding activity/capacity of molecules like peptides and proteins can be determined by, for example, an enzyme linked immunosorbent assay (ELISA) using, for example, sera obtained from a subject, (i.e., an allergic subject) that has been previously exposed to the wild-type allergen. Briefly, a peptide to be tested is coated onto wells of a microtiter plate. After washing and blocking the wells, an antibody solution consisting of the plasma of an allergic subject, who has been exposed to the peptide being tested or the protein from which it was derived, is incubated in the wells. A labelled secondary antibody is added to the wells and incubated. The amount of IgE-binding is then quantified and compared to the amount of IgE bound by a purified wild-type allergen.

Alternatively, the binding activity of a peptide can be determined by Western blot analysis. For example, a peptide to be tested is run on a polyacrylamide gel using SDS-PAGE. The peptide is then transferred to nitrocellulose and subsequently incubated with serum from an allergic subject. After incubation with the labelled secondary antibody, the amount of IgE bound is determined and quantified.

Another assay which can be used to determine IgE-binding activity of a peptide is a competition ELISA assay. Briefly, an IgE-antibody pool is generated by combining plasma from allergic subjects who have been shown by direct ELISA to be IgE-reactive with wild-type allergen. This pool is used in ELISA competition assays to compare IgE-binding to wild-type allergen to the peptide tested. IgE-binding for the wild-type allergen and the peptide being tested is determined and quantified.

A "T-cell epitope" means a protein (e.g., allergen) or fragment thereof, for which a T-cell has an antigen specific binding site, the result of binding to said binding site activates the T-cell. The term "exhibiting reduced T-cell reactivity", as used herein, refers to molecules which exhibit a T-cell reactivity which is significantly reduced compared to the stimulation induced by the wild-type allergen from which the hypoallergenic molecule is derivedusing equimolar amounts in standard assays known in the art (reduced T-cell reactivity means at least 30%, preferably at least 50%, more preferably at least 70%, most preferably at least 90%, less stimulation of hypoallergenic molecules compared to the wildtype allergen at equimolar amounts). In a particular preferred embodiment of this invention, the molecules may "lack" T-cell epitopes and thus molecule shows reduced T-cell reactivity in the individual(s) to be treated (i.e., who is to receive an epitope-presenting valency platform molecule). It is likely that, for example, an allergen-derived molecule may lack a T-cell epitope(s) with respect to an individual, or a group of individuals, while possessing a T-cell epitope(s) with respect to other individual(s). Methods for detecting the presence of a T-cell epitope are known in the art and include assays which detect T-cell proliferation (such as thymidine incorporation). Immunogens that fail to induce statistically significant incorporation of thymidine above background (i.e., generally p less than 0.05 using standard statistically methods) are generally considered to lack T-cell epitopes, although it will be appreciated that the quantitative amount of thymidine incorporation may vary, depending on the immunogen being tested (see, e.g., Zhen L. et al. (Infect Immun. (2003) 71:3920-3926)). Generally, a stimulation index below about 2-3, more preferably less than about 1, indicates lack of T-cell reactivity and epitopes. The presence of T-cell epitopes can also be determined by measuring secretion of T-cell-derived lymphokines according to standard methods. The stimulation index (SI) may be calculated by dividing the proliferation rate (Thymidine uptake) of stimulated cells through the proliferation rate of unstimulated cells in medium alone. SI=1 means no stimulation, SI<1 indicates toxic effects and SI>1 indicates stimulation of cells. Location and content of T-cell epitopes, if present, can be determined empirically.

The cytokine secretion may be determined in addition to the stimulation of T cells. For example, IFN-gamma has been recognized as a harmful cytokine. Other examples may be TNF-alpha, IL-5, IL-4, IL-8 etc.

The allergen fragment is preferably composed of amino acids 151 to 177, 87 to 117, 1 to 30, 43 to 70 or 212 to 241 of Phl p 1, amino acids 93 to 128, 98 to 128, 26 to 53, 26 to 58, 132 to 162, 217 to 246, 252 to 283 or 176 to 212 of Phl p 5, amino acids 1 to 34 or 35 to 70 of chain 1 of Fel d 1, amino acids 1 to 34, 35 to 63 or 64 to 92 of chain 2 of Fel d 1, amino acids 30 to 59, 50 to 79 or 75 to 104 of Bet v 1, amino acids 1 to 33, 21 to 51, 42 to 73, 62 to 103 or 98 to 129 of Der p 2, amino acids 1 to 30, 20 to 50, 50 to 80, 90 to 125, 125 to 155 or 165 to 198 of Der p 7, amino acids 1-35, 36-70, 71-110, 111-145, 140-170, 175-205, 210-250 or 250-284 of Der p 10, amino acids 1 to 35, 35 to 72, 70 to 100 or 90 to 122 of Der p 21, amino acids 1 to 32, 15 to 48 or 32 to 70 of Clone 30, amino acids 19 to 58, 59 to 95, 91 to 120 or 121 to 157 of Alt a 1, amino acids 31 to 60, 45 to 80, 60 to 96 or 97 to 133 of Par j 2, amino acids 1 to 40, 36 to 66, 63 to 99, 86 to 120 or 107 to 145 of Ole e 1, amino acids 25 to 58, 99 to 133, 154 to 183, 277 to 307, 334 to 363, 373 to 402, 544 to 573, 579 to 608, 58 to 99, 125 to 165, 183 to 224, 224 to 261, 252 to 289, 303 to 340, 416 to 457, 460 to 500 or 501 to 542 of Fel d 2, amino acids 19 to 58, 52 to 91, 82 to 119, 106 to 144 or 139 to 180 of Can f 2, amino acids 19 to 56, 51 to 90, 78 to 118, 106 to 145 or 135-174 of Can f 1, amino acids 27 to 70, 70 to 100 or 92 to 132 of Art v 1, amino acids 31 to 70, 80 to 120, 125 to 155, 160 to 200, 225 to 263, 264 to 300 305 to 350 or 356 to 396 of Amb a 1, amino acids 1 to 34, 35 to 74, 74 to 115, 125 to 165, 174 to 213, 241 to 280, 294 to 333, 361 to 400 or 401 to 438 of Alt a 6, amino acids 1 to 40, 41 to 80, 81 to 120, 121 to 160 of Alt a 2 or fragments or sequence variations thereof.

The specific amino acid sequences of the above identified allergen-derived molecules are:

| Peptide | Position | Sequence | SEQ ID No. |
| --- | --- | --- | --- |
| Pep Alt a 1.1 | 19-58 | APLESRQDTASCPVTTEGDYVWKISEFYGRKPEG-TYYNSL | 23 |
| Pep Alt a 1.2 | 59-95 | GFNIKATNGGTLDFTCSAQADKLEDHKWYSCGENSFM | 24 |
| Pep Alt a 1.3 | 91-120 | ENSFMDFSFDSDRSGLLLKQKVSDDITYVA | 25 |
| Pep Alt a 1.4 | 121-157 | TATLPNYCRAGGNGPKDFVCQGVADAYITLVTLPKSS | 26 |
| Pep Alt a 2.1 | 1-40 | MHSSNNFFKDNIFRSLSKEDPDYSRNIEGQVIRLH-WDWAQ | 27 |
| Pep Alt a 2.2 | 41-80 | LLMLSAKRMKVAFKLDIEKDQRVWDRCTADDLK-GRNGFKR | 28 |

| Peptide | Position | Sequence | SEQ ID No. |
|---|---|---|---|
| Pep Alt a 2.3 | 81-120 | CLQFTLYRPRDLLSLLNEAFFSAFRENRETIINTD-LEYAA | 29 |
| Pep Alt a 2.4 | 121-160 | KSISMARLEDLWKEYQKIFPSIQVITSAFRSIE-PELTVYT | 30 |
| Pep Alt a 2.5 | 161-190 | CLKKIEASFELIEENGDPKITSEIQLLKAS | 31 |
| Pep Alt a 6.1 | 1-34 | MTITKIHARSVYDSRGNPTVEVDIVTETGLHRAI | 32 |
| Pep Alt a 6.2 | 35-74 | VTETGLHRAIVPSGASTGSHEACELRDGDKSKWG-GKGVTK | 33 |
| Pep Alt a 6.3 | 74-115 | APALIKEKLDVKDQSAVDAFLNKLDGTTNKTNL-GANAILGVS | 34 |
| Pep Alt a 6.4 | 125-165 | EKGVPLYAHISDLAGT KKPYVLPVPF QNVLNG-GSHAGGRLA | 35 |
| Pep Alt a 6.5 | 174-213 | CEAPTFSEAMRQGAEVYQKLKALAKKTYGQSAGN-VGDEGG | 36 |
| Pep Alt a 6.6 | 241-280 | IKIAMDVASSEFYKADEKKYDLDFKNPDSDKSKWL-TYEQL | 37 |
| Pep Alt a 6.7 | 294-333 | VSIEDPFAEDDWEAWSYFFKTYDGQIVGDDLTVT-NPEFIK | 38 |
| Pep Alt a 6.8 | 361-400 | AKDAFGAGWGVMVSHRSGETEDVTIADIVVGLRS-GQIKTG | 39 |
| Pep Alt a 6.9 | 401-438 | APARSERLAKLNQILRIEEELGDNAVYAGNNFR-TAVNL | 40 |
| Pep Amb a 1.1 | 31-70 | EILPVNETRRLTTSGAYNIIDGCWRGKADWAEN-RKALADC | 41 |
| Pep Amb a 1.2 | 80-120 | GGKDGDIYTVTSELDDDVANPKEGTLRFGAAQNR-PLWIIFE | 42 |
| Pep Amb a 1.3 | 125-155 | IRLDKEMVVNSDKTIDGRGAKVEIINAGFTL | 43 |
| Pep Amb a 1.4 | 160-200 | NVIIHNINMHDVKVNPGGLIKSNDGPAAPRAGSDG-DAISIS | 44 |
| Pep Amb a 1.5 | 225-263 | GTTRLTVSNSLFTQHQFVLLFGAGDENIEDRGMLAT-VAF | 45 |
| Pep Amb a 1.6 | 264-300 | NTFTDNVDQRMPRCRHGFFQVVNNNYDKWGSYAIGGS | 46 |
| Pep Amb a 1.7 | 305-350 | ILSQGNRFCAPDERSKKNVLGRHGEAAAESMKWN-WRTNKDVLENGA | 47 |
| Pep Amb a 1.8 | 356-396 | GVDPVLTPEQSAGMIPAEPGESALSLTSSAGVLSC-QPGAPC | 48 |
| Pep Art v 1.1 | 27-70 | SKLCEKTSKTYSGKCDNKKCDKKCIEWEKAQHGACH-KREAGKES | 49 |
| Pep Art v 1.2 | 70-100 | SCFCYFDCSKSPPGATPAPPGAAPPPAAGGS | 50 |
| Pep Art v 1.3 | 92-132 | APPPAAGGSPSPPADGGSPPPPADGGSPPVDGG-SPPPPSTH | 51 |
| Can f 1 Pep 1 | 19-56 | QDTPALGKDTVAVSGKWYLKAMTADQEVPEKPDSVT-PM | 52 |
| Can f 1 Pep 2 | 51-90 | DSVTPMILKAQKGGNLEAKITMLTNGQCQNITVVL-HKTSE | 53 |
| Can f 1 Pep 3 | 78-118 | CQNITVVLHKTSEPGKYTAYEGQRVVFIQPSPVRD-HYILYC | 54 |
| Can f 1 Pep 4 | 106-145 | QPSPVRDHYILYCEGELHGRQIRMAKLLGRD-PEQSQEALE | 55 |

-continued

| Peptide | Position | Sequence | SEQ ID No. |
|---|---|---|---|
| Can f 1 Pep 5 | 135-174 | RDPEQSQEALEDFREFSRAKGLNQEILELAQSETC-SPGGQ | 56 |
| Can f 2 Pep 1 | 19-58 | QEGNHEEPQGGLEELSGRWHSVALASNKSDLIKP-WGHFRV | 57 |
| Can f 2 Pep 2 | 52-91 | PWGHFRVFIHSMSAKDGNLHGDILIPQDGQCEK-VSLTAFK | 58 |
| Can f 2 Pep 3 | 82-119 | CEKVSLTAFKTATSNKFDLEY-WGHNDLYLAEVDPKSYL | 59 |
| Can f 2 Pep 4 | 106-144 | NDLYLAEVDPKSYLILYMINQYN-DDTSLVAHLMVRDLSR | 60 |
| Can f 2 Pep 5 | 139-180 | VRDLSRQQDFLPAFESVCEDIGLHKDQIVVLS-DDDRCQGSRD | 61 |
| Fel d 2 Pep 1 | 25-58 | EAHQSEIAHRFNDLGEEHFRGLVLVAFSQYLQQC | 62 |
| Fel d 2 Pep 2 | 99-133 | CTVASLRDKYGEMADCCEKKEPERNECFLQHKDDN | 63 |
| Fel d 2 Pep 3 | 154-183 | NEQRFLGKYLYEIARRHPYFYAPELLYYAE | 64 |
| Fel d 2 Pep 4 | 277-307 | CADDRADLAKYICENQDSISTKLKECCGKPV | 65 |
| Fel d 2 Pep 5 | 334-363 | VEDKEVCKNYQEAKDVFLGTFLYEYSRRHP | 66 |
| Fel d 2 Pep 6 | 373-402 | LAKEYEATLEKCCATDDPPACYAHVFDEFK | 67 |
| Fel d 2 Pep 7 | 544-573 | EKQIKKQSALVELLKHKPKATEEQLKTVMG | 68 |
| Fel d 2 Pep 8 | 579-608 | VDKCCAAEDKEACFAEEGPKLVAAAQAALA | 69 |
| Fel d 2 Pep 9 | 58-99 | CPFEDHVKLVNEVTEFAKGCVADQSAANCEK-SLHELLGDKLC | 70 |
| Fel d 2 Pep 10 | 125-165 | CFLQHKDDNPGFGQLVTPEADAMCTAFHENEQRFLG-KYLYE | 71 |
| Fel d 2 Pep 11 | 183-224 | EEYKGVFTECCEAADKAACLTPKVDALREKVLAS-SAKERLKC | 72 |
| Fel d 2 Pep 12 | 224-261 | CASLQKFGERAFKAWSVARLSQKFPKAE-FAEISKLVTD | 73 |
| Fel d 2 Pep 13 | 252-289 | FAEISKLVTDLAKIHKECCHGDLLECADDRADLAKY-IC | 74 |
| Fel d 2 Pep 14 | 303-340 | CGKPVLEKSHCISEVERDELPADLPPLAVD-FVEDKEVC | 75 |
| Fel d 2 Pep 15 | 416-457 | CELFEKLGEYGFQNALLVRYTKKVPQVST-PTLVEVSRSLGKV | 76 |
| Fel d 2 Pep 16 | 460-500 | CTHPEAERLSCAEDYLSVVLNRLCVLHEKTPVSER-VTKC | 77 |
| Fel d 2 Pep 17 | 501-542 | CTESLVNRRPCFSALQVDETYVPKEFSAETFTF-HADLCTLPE | 78 |
| Pep Ole e 1.1 | 1-40 | EDIPQPPVSQFHIQGQVYCDTCRAGFITELSEFIP-GASLR | 79 |
| Pep Ole e 1.2 | 36-66 | GASLRLQCKDKENGDVTFTEVGYTRAEGLYS | 80 |
| Pep Ole e 1.3 | 63-99 | GLYSMLVERDHKNEFCEITLISSGRKDCNEIPTEGWA | 81 |
| Pep Ole e 1.4 | 86-120 | GRKDCNEIPTEGWAKPSLKFKLNTVNGTTRTVNPL | 82 |
| Pep Ole e 1.5 | 107-145 | LNTVNGTTRTVNPLGFFKKEALPKCAQVYNKL-GMYPPNM | 83 |
| Pep Par j 2.1 | 31-60 | GEEACGKVVQDIMPCLHFVKGEEKEPSKEC | 84 |
| Pep Par j 2.2 | 45-80 | CLHFVKGEEKEPSKECCSGTKKLSEEVKTTEQKREA | 85 |

-continued

| Peptide | Position | Sequence | SEQ ID No. |
|---|---|---|---|
| Pep Par j 2.3 | 60-96 | CCSGTKKLSEEVKTTEQKREACKCIVRATKGISGIKN | 86 |
| Pep Par j 2.4 | 97-133 | ELVAEVPKKCDIKTTLPPITADFDCSKIQSTIFRGYY | 87 |
| Der p 1 Pep 1 | 1-30 | TNACSINGNAPAEIDLRQMRTVTPIRMQGG | 88 |
| Der p 1 Pep 2 | 52-84 | NQSLDLAEQELVDCASQHGCHGDTIPRGIEYIQ | 89 |
| Der p 1 Pep 3 | 85-115 | HNGVVQESYYRYVAREQSCRRPNAQRFGISN | 90 |
| Der p 1 Pep 4 | 99-135 | REQSCRRPNAQRFGISNYCQIYPPNVNKIREALAQTH | 91 |
| Der p 1 Pep 5 | 145-175 | KDLDAFRHYDGRTIIQRDNGYQPNYHAVNIV | 92 |
| Der p 1 Pep 6 | 155-187 | GRTIIQRDNGYQPNYHAVNIVGYSNAQGVDYWI | 93 |
| Der p 1 Pep 7 | 175-208 | VGYSNAQGVDYWIVRNSWDTNWGDNGYGYFAANI | 94 |
| Der p 1 Pep 8 | 188-222 | VRNSWDTNWGDNGYGYFAANIDLMMIEEYPYVVIL | 95 |
| Der p 2 Pep 1 | 1-33 | DQVDVKDCANHEIKKVLVPGCHGSEPCIIHRGK | 96 |
| Der p 2 Pep 2 | 21-51 | CHGSEPCIIHRGKPFQLEAVFEANQNSKTAK | 97 |
| Der p 2 Pep 3 | 42-73 | EANQNSKTAKIEIKASIEGLEVDVPGIDPNAC | 98 |
| Der p 2 Pep 4 | 62-103 | EVDVPGIDPNACHYMKCPLVKGQQYDIKYTWIVP-KIAPKSEN | 99 |
| Der p 2 Pep 5 | 98-129 | APKSENVVVTVKVMGDNGVLACAIATHAKIRD | 100 |
| Der p 5 Pep 1 | 1-35 | MEDKKHDYQNEFDFLLMERIHEQIKKGELALFYLQ | 101 |
| Der p 5 Pep 2 | 25-60 | KKGELALFYLQEQINHFEEKPTKEMKDKIVAEMDTI | 102 |
| Der p 5 Pep 3 | 65-95 | DGVRGVLDRLMQRKDLDIFEQYNLEMAKKSG | 103 |
| Der p 5 Pep 4 | 78-114 | DLDIFEQYNLEMAKKSGDILERDLKKEEARVKKIEV | 104 |
| Der p 7 Pep 1 | 1-30 | DPIHYDKITEEINKAVDEAVAAIEKSETFD | 105 |
| Der p 7 Pep 2 | 20-50 | VAAIEKSETFDPMKVPDHSDKFERHIGIIDL | 106 |
| Der p 7 Pep 3 | 50-80 | LKGELDMRNIQVRGLKQMKRVGDANVKSEDG | 107 |
| Der p 7 Pep 4 | 90-125 | VHDDVVSMEYDLAYKLGDLHPNTHVISDIQDFVVEL | 108 |
| Der p 7 Pep 5 | 125-155 | LSLEVSEEGNMTLTSFEVRQFANVVNHIGGL | 109 |
| Der p 7 Pep 6 | 165-198 | LSDVLTAIFQDTVRAEMTKVLAPAFKKELERNNQ | 110 |
| Der p 10 Pep 1 | 1-35 | MEAIKKKMQAMKLEKDNAIDRAEIAEQKARDANLR | 111 |
| Der p 10 Pep 2 | 36-70 | AEKSEEEVRALQKKIQQIENELDQVQEQLSAANTK | 112 |
| Der p 10 Pep 3 | 71-110 | LEEKEKALQTAEGDVAALNRRIQLIEEDLERSEER-LKIAT | 113 |
| Der p 10 Pep 4 | 111-145 | AKLEEASQSADESERMRKMLEHRSITDEERMEGLE | 114 |
| Der p 10 Pep 5 | 140-170 | RMEGLENQLKEARMMAEDADRKYDEVARKLA | 115 |
| Der p 10 Pep 6 | 175-205 | DLERAEERAETGESKIVELEEELRVVGNNLK | 116 |
| Der p 10 Pep 7 | 210-250 | SEEKAQQREEAHEQQIRIMTTKLKEAEARAEFAERS-VQKLQ | 117 |
| Der p 10 Pep 8 | 250-284 | QKEVDRLEDELVHEKEKYKSISDELDQTFAELTGY | 118 |
| Der p 21 Pep 1 | 1-35 | MFIVGDKKEDEWRMAFDRLMMEELETKIDQVEKGL | 119 |
| Der p 21 Pep 2 | 35-72 | LHLSEQYKELEKTKSKELKEQILRELTIGENFMKGAL | 120 |
| Der p 21 Pep 3 | 70-100 | GALKFFEMEAKRTDLNMFERYNYEFALESIK | 121 |
| Der p 21 Pep 4 | 90-122 | YNYEFALESIKLLIKKLDELAKKVKAVNPDEYY | 122 |

-continued

| Peptide | Position | Sequence | SEQ ID No. |
|---|---|---|---|
| Clone 30 Pep 1 | 1-32 | MANDNDDDPTTTVHPTTTEQPDDKFECPSRFG | 123 |
| Clone 30 Pep 2 | 15-48 | PTTTEQPDDKFECPSRFGYFADPKDPHKFYICSN | 124 |
| Clone 30 Pep 3 | 32-70 | GYFADPKDPHKFYICSNWEAVHKDCPGNTRWNEDEETCT | 125 |
| Bet v 1 Pep 1 | 30-59 | LFPKVAPQAISSVENIEGNGGPGTIKKISF | 126 |
| Bet v 1 Pep 2 | 50-79 | GPGTIKKISFPEGFPFKYVKDRVDEVDHTN | 127 |
| Bet v 1 Pep 3 | 75-104 | VDHTNFKYNYSVIEGGPIGDTLEKISNEIK | 128 |
| Fel d 1 chain 1 Pep 1 | 1-34 | EICPAVKRDVDLFLTGTPDEYVEQVAQYKALPVVC | 129 |
| Fel d 1 chain 1 Pep 2 | 35-70 | LENARILKNCVDAKMTEEDKENALSLLDKIYTSPLC | 130 |
| Fel d 1 chain 2 Pep 1 | 1-34 | VKMAITCPIFYDVFFAVANGNELLLDLSLTKVNAC | 131 |
| Fel d 1 chain 2 Pep 2 | 35-63 | TEPERTAMKKIQDCYVENGLISRVLDGLVC | 132 |
| Fel d 1 chain 2 Pep 3 | 64-92 | CMTTISSSKDCMGEAVQNTVEDLKLNTLGR | 133 |
| Phl p 5 Pep 1 | 98-128 | CGAASNKAFAEGLSGEPKGAAESSSKAALTSK | 134 |
| Phl p 5 Pep 2 | 26-58 | ADLGYGPATPAAPAAGYTPATPAAPAEAAPAGKC | 135 |
| Phl p 5 Pep 3 | 132-162 | AYKLAYKTAEGATPEAKYDAYVATLSEALRIC | 136 |
| Phl p 5 Pep 4 | 217-246 | CEAAFNDAIKASTGGAYESYKFIPALEAAVK | 137 |
| Phl p 5 Pep 5 | 252-283 | TVATAPEVKYTVFETALKKAITAMSEAQKAAKC | 138 |
| Phl p 5 Pep 6 | 176-212 | CAEEVKVIPAGELQVIEKVDAAFK-VAATAANAAPANDK | 139 |
| Phl p 5 Pep 1a | 93-128 | CFVATFGAASNKAFAEGLSGEPKGAAESSSKAALTSK | 141 |
| Phl p 5 Pep 2b | 26-53 | ADLGYGPATPAAPAAGYTPATPAAPAEAC | 142 |

The terms "fragments thereof" and "sequence variations thereof" refer to peptides which are deduced from the allergen-derived molecules disclosed herein and show biochemical properties (e.g. the capacity to prevent IgE binding to the allergen from which those molecules are derived from) which are comparable or identical to said allergen-derived molecules. The fragments of the present invention comprise at least 5, preferably at least 7, more preferably at least 10, successive and/or a maximum of 95%, preferably a maximum of 90%, more preferably a maximum of 80% amino acid residues of the allergen-derived molecule. The term "sequence variation" includes modifications of the peptides such as fragmentation (see above), amino acid substitutions (e.g. with other natural or non-natural amino acids or amino acid derivatives), deletions or additions. "Sequence variation" refers also to said allergen-derived molecules of the above table, wherein at least 1, preferably at least 2, more preferably at least 3, even more preferably at least 4 (5, 6, 7, 8, 9, 10, 15, 20) amino acid residues are added to the C- and/or N-terminus.

It is noted that the clone 30 allergen is an allergen derived from the house dust mite *Dermatophagoides pteronyssinus* and consists of the following sequence: MANDND-DDPTTTVHPTTTEQPDDKFECPSRFGY-FADPKDPHKFYICSNWEAVHKDCPGNTR-WNEDEETCT (SEQ ID No. 140; see also AT A 733/2006).

According to the present invention also peptides are encompassed which are at least 80% identical, preferably 90% identical, to the amino sequences disclosed above.

Another aspect of the present invention relates to a nucleic acid molecule encoding a fused hypoallergenic protein according to the present invention.

Another aspect of the present invention relates to a vector comprising a nucleic acid molecule according to the present invention.

Said vector is preferably an expression vector.

The vector harbouring the nucleic acid molecule of the present invention may be used for cloning purposes or for the production of expression vectors. Said vector can be a plasmid, cosmid, virus, bacteriophage or any other vector commonly used in genetic engineering, and can include, in addition to the nucleic acid molecule of the invention, eukaryotic or prokaryotic elements for the control of the expression, such as regulatory sequences for the initiation and the termination of the transcription and/or translation, enhancers, promoters, signal sequences and the like.

According to a preferred embodiment of the present invention the vector is a bacterial, fungal, insect, viral or mammalian vector.

The vector of the present invention may preferably be employed for cloning and expression purposes in various hosts. Therefore, said vector comprises besides a nucleic acid encoding for a hypoallergenic molecule or fusion protein according to the present invention host specific regulatory sequences.

Another aspect of the present invention relates to a host comprising a nucleic acid molecule or a vector according to the present invention.

The nucleic acid molecule and the vector according to the present invention may be introduced into a suitable host. Said molecule may be incorporated into the genome of the host. The vector may exist extrachromosomally in the cytoplasm or incorporated into the chromosome of the host.

Yet another aspect of the present invention relates to an antibody directed against a hypoallergenic molecule, hypoallergenic fusion protein or a fusion protein according to the present invention.

According to a preferred embodiment of the present invention the antibody is a monoclonal or polyclonal antibody.

Antibodies according to the present invention include, but are not limited to, polyclonal, monoclonal, multispecific, humanized or chimeric antibodies, single chain antibodies, Fab fragments, F(ab') fragments and epitope-binding fragments of any of the above. Furthermore, antibodies are considered to be immunoglobulin molecules and immunologically active portions of immunoglobulin molecules, i.e., molecules that contain an antigen binding site that immunospecifically binds an antigen. The immunoglobulin molecules of the invention are preferably of the types IgG, IgM, IgD, IgA and IgY, class (e.g., IgG1, IgG2, IgG3, IgG4, IgA1 and IgA2) or subclass of immunoglobulin molecule.

Polyclonal antibodies can be prepared by administering a polypeptide of the invention, preferably using an adjuvant, to a non-human mammal and collecting the resultant antiserum. Improved titers can be obtained by repeated injections over a period of time. There is no particular limitation to the species of mammals which may be used for eliciting antibodies; it is generally preferred to use rabbits or guinea pigs, but horses, cats, dogs, goats, pigs, rats, cows, sheep, camels etc., can also be used. In the production of antibodies, a definite amount of immunogen of the invention is, e.g., diluted with physiological saline solution to a suitable concentration, and the resulting diluted solution is mixed with, e.g., complete Freund's adjuvant to prepare a suspension or with mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. The suspensions and mixtures are administered to mammals, e.g., intraperitoneally, e.g., to a rabbit, using from about 50 µg to about 2,500 µg polypeptide of the invention per administration. The suspension is preferably administered about every two weeks over a period of up to about 2-3 months, preferably about 1 month, to effect immunization. The antibody is recovered by collecting blood from the immunized animal after the passage of 1 to 2 weeks after the last administration, centrifuging the blood and isolating serum from the blood.

Monoclonal antibodies may, e.g., be of human or murine origin. Murine monoclonal antibodies may be prepared by the method of Köhler and Milstein (Köhler, G. and Milstein, C., Nature 256 (1975) 495), e.g., by fusion of spleen cells of hyperimmunized mice with an appropriate mouse myeloma cell line.

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., (1989) J. Immunol. Methods 125:191-202; U.S. Pat. No. 5,807,715; U.S. Pat. No. 4,816,567 and U.S. Pat. No. 4,816,397.

Humanized antibodies are antibody molecules from a non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modelling of the interactions of the CDR and framework residues to identify framework residues important for antigen binding and sequence comparison to identify unusual framework residues at particular positions (see, e.g., Queen et al., U.S. Pat. No. 5,585,089; Riechmann et al., Nature 332: 323 (1988)). Antibodies can be humanized using a variety of techniques known in the art including, for example, CDR-grafting (EP 239,400; WO 91/09967; U.S. Pat. No. 5,225,539; U.S. Pat. No. 5,530,101; and U.S. Pat. No. 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-913 (1994)), and chain shuffling (U.S. Pat. No. 5,565,332).

The antibodies according to the present invention may advantageously be used for desensitization of an individual suffering from an allergy, in particular from house dust mite allergy. For passive immunisation the antibody is preferably an IgG or a derivative thereof (e.g., chimeric or humanized antibody). Furthermore, this antibody may also be used for desensibilisation of an individual.

Another aspect of the present invention relates to a vaccine formulation comprising a hypoallergenic protein or an antibody according to the present invention.

The vaccine formulation according to the present invention may be formulated as known in the art and necessarily adapted to the way of administration of said vaccine formulation.

Preferred ways of administration of the vaccine formulation (of the present invention) include all standard administration regimes described and suggested for vaccination in general and allergy immunotherapy specifically (orally, transdermally, intraveneously, intranasally, via mucosa, rectally, etc). However, it is particularly preferred to administer the molecules and proteins according to the present invention subcutaneously or intramusculary.

The vaccine formulation according to the present invention may only comprise a viral capsid protein or fragments thereof of a member of the genus of rhinovirus Said formulation preferably further comprises at least one adjuvant, pharmaceutical acceptable excipient and/or preservative.

In order to increase the immunogenicity of the hypoallergenic molecules according to the present invention, adjuvants, for instance, may be used in a medicament according to the present invention. An adjuvant according to the present invention is an auxiliary agent which, when administered together or in parallel with an antigen, increases its immunogenicity and/or influences the quality of the immune response. Hence, the adjuvant can, e.g., considerably influence the extent of the humoral or cellular immune response.

Customary adjuvants are, e.g., aluminum compounds, lipid-containing compounds or inactivated mycobacteria.

Generally, adjuvants can be of different forms, provided that they are suitable for administration to human beings. Further examples of such adjuvants are oil emulsions of mineral or vegetal origin, mineral compounds such as aluminium phosphate or hydroxide, or calcium phosphate, bacterial products and derivatives, such as P40 (derived from the cell wall of *Corynebacterium granulosum*), monophosphoryl lipid A (MPL, derivative of LPS) and muramyl peptide derivatives and conjugates thereof (derivatives from mycobacterium components), alum, incomplete Freund's adjuvant, liposyn, saponin, squalene, etc. (see, e.g., Gupta R. K. et al. (Vaccine 11:293-306 (1993)) and Johnson A. G. (Clin. Microbiol. Rev. 7:277-289).

According to another preferred embodiment of the present invention said formulation comprises 10 ng to 1 g, preferably 100 ng to 10 mg, especially 0.5 µg to 200 µg of said hypoallergenic molecule or antibody.

Another aspect of the present invention relates to the use of a hypoallergenic protein or an antibody according to the present invention for manufacturing a medicament for the treatment or prevention of a viral infection and/or an allergy in a human or animal.

Said medicament preferably further comprises at least one adjuvant, pharmaceutical acceptable excipient and/or preservative.

The medicament according to the present invention may be used for active (administration of the hypoallergenic protein and/or molecules of the invention) as well as for passive immunization (antibodies directed to the hypoallergenic protein and/or molecules of the invention).

According to a preferred embodiment of the present invention said medicament comprises 10 ng to 1 g, preferably 100 ng to 10 mg, especially 0.5 µg to 200 µg of said hypoallergenic molecule, nucleic acid molecule, vector, host or antibody.

The medicament is preferably administered to an individual in amount of 0.01 mg/kg body weight to 5 mg/kg body weight, preferably 0.1 mg/kg body weight to 2 mg/kg body weight.

The particular dosage regimen, i.e., dose, timing and repetition, will depend on the particular individual and that individual's medical history. Empirical considerations, such as the half life, will generally contribute to determination of the dosage. Frequency of administration may be determined and adjusted over the course of therapy.

The individual to whom the medicament according to the present invention is administered is preferably an individual or animal which is at risk to become an allergy.

Subjects having or at risk of having an allergic condition, disorder or disease include subjects with an existing allergic condition or a known or a suspected predisposition towards developing a symptom associated with or caused by an allergic condition. Thus, the subject can have an active chronic allergic condition, disorder or disease, an acute allergic episode, or a latent allergic condition, disorder or disease. Certain allergic conditions are associated with seasonal or geographical environmental factors. Thus, at risk subjects include those at risk from suffering from a condition based upon a prior personal or family history, and the season or physical location, but which the condition or a symptom associated with the condition may not presently manifest itself in the subject.

The administration of the medicament according to the present invention, which comprises at least one hypoallergenic molecule as described herein, to an individual may prevent sensitization of said individual or may induce an appropriate immune response to allergens. If the medicament of the present invention is used to prevent sensitization, it should be administered to an individual prior to the first contact with said allergen. Therefore, it is preferred to administer the medicament according to the present invention to neonates and children. It turned out that also the administration of the medicament according to the present invention to pregnant individuals will induce the formation of antibodies directed against allergens in the unborn child. It is especially beneficiary to use hypoallergenic molecules according to the present invention for such therapies, because due to the lack of T-cell epitopes side effects occurring in the course of allergen immunotherapy can significantly be reduced or even be completely avoided.

Yet another aspect of the present invention relates to the use of a hypoallergenic protein or an antibody according to the present invention for the diagnosis of an allergy and/or a viral infection in an individual.

Another aspect of the present invention relates to the use a viral capsid protein from a virus of the family of picornaviridae as a carrier in medicaments or vaccines or for diagnosing a viral infection, in particular common cold.

As a valuable alternative to the widely spread KLH carrier protein viral capsid proteins of viruses of the family of picornaviridae may be used. The carrier may be conjugated chemically or fused with recombinant techniques to peptides, proteins and polypeptides or other antigens. Furthermore, the viral capsid protein may be used to detect, e.g., antibodies directed to said capsid protein in the serum of an individual.

One of the advantages of such a carrier is that not only the antigen fused or conjugated thereon may be exposed to the immune system, but also an immune response against the capsid protein of a rhinovirus is induced. Consequently, such a vaccination leads to the prevention and/or treatment of diseases caused by rhinoviruses. The virus is preferably of the species of human rhinoviruses, in particular human rhinovirus 89 and 14.

Another aspect of the present invention relates to a hypoallergenic molecule derived from Phl p 5 (Genbank Nr. X7435) having a C- and/or N-terminal truncation and lacking substantially IgE-binding capacity.

Grass pollen is one of most potent outdoor seasonal sources of airborne allergens responsible for hay fever and allergic asthma.

More than 40% of allergic individuals display IgE-reactivity with grass pollen allergens, which are divided into more than 11 groups. More than 80% of the grass pollen allergic patients react with group 5 allergens.

Group 5 allergens are non-glycosylated, highly homologous proteins with a molecular mass range from 25-33 kD. Several group 5 allergens have been cloned and/or immunologically characterized.

The trial to reduce the allergenic activity by introducing pointmutations, mutations of several amino acids in row or deletions showed no effect (Schramm G, et al. J Immunol 1999; 162: 2406-1435). IgE-binding regions of Phl p 5 (Flicker S, et al. J Immunol 2000; 165: 3849-3859) have already been described and the three-dimensional structure has been solved (Maglio O, et al. 2002. Protein Eng. 15:635-642).

It turned out that in particular the Phl p 5 peptides according to the present invention, which are C- and/or N-terminally truncated and lack IgE-binding capacity, may be employed for the active vaccination of individuals.

According to a preferred embodiment of the present invention the truncated molecule lacks T-cell epitopes.

As already outlined above, late side effects of allergen immunotherapy can be significantly reduced or even be avoided if the hypoallergenic molecules substantially lack T-cell epitopes.

Truncated Phl p 5 molecules lacking T-cell epitopes are composed of amino acids 93 to 128, 98 to 128, 26 to 53, 26 to 58 or 252 to 283 of Phl p 5 or fragments or sequence variations thereof.

In particular these truncated molecules substantially show no T-cell epitopes and are, nevertheless, able to provoke an appropriate immune response directed against the wild-type allergen.

According to another preferred embodiment of the present invention the hypoallergenic truncated Phl p 5 is composed of amino acids 132 to 162, 217 to 246 or 176 to 212 of Phl p 5 or sequence variations thereof.

These hypoallergenic molecules comprise one or more T-cell epitopes but lack IgE-binding capacity.

Another aspect of the present invention relates to a hypoallergenic molecule derived from Fel d 1 (Genbank Nr. X62477 and X62478) having a C- and/or N-terminal truncation and lacking IgE-binding capacity.

Allergies to animals affect up to 40% of allergic patients. In the domestic environment, allergies to the most popular pets, cats and dogs, are particularly prevalent and connected with perennial symptoms. Animal allergens are present in dander, epithelium, saliva, serum or urine. Exposure to the allergens can occur either by direct skin contact or by inhalation of particles carrying the allergens. The major cat and dog allergens were shown to be present widespread and could even be detected in non-pet owning households and in public places, e.g., schools. This can be attributed to the high and increasing number of households keeping pets in industrialized countries (about 50%) and the high stability of the allergens, which are carried off and distributed.

Fel d 1 was identified as the major cat allergen, which is recognized by more than 90% of cat allergic patients. Fel d 1 represents a 38 kDa acidic glycoprotein of unknown biological function. It consists of two identical non-covalently linked heterodimers, which, again, are composed of two polypeptide chains antiparallely linked by three disulfide bonds. Chain 1 and chain 2 are encoded on different genes, each consisting of 3 exons. Recombinant Fel d 1 (rFel d 1), expressed as a chain 2- to chain 1 fusion protein, has been generated in *E. coli*. This recombinant Fel d 1 is able to completely mimic the immunological properties of the wild-type allergen.

Peptides derived from the major cat allergen Fel d 1, and lacking IgE-binding capacity are suitable, e.g., for immunotherapy and prophylactic allergy vaccination. These peptides may be comprised in a larger polypeptide or be coupled to a suitable carrier protein such as keyhole limpet hemocyanin (KLH). The Fel d 1-derived synthetic peptides—like the Phl p 5 and allergen-derived peptides disclosed herein—are capable of inducing an IgG response, i.e., the production of so called "blocking antibodies" or "protective antibodies". These antibodies prevent IgE-binding to the allergen Fel d 1. A significant reduction in allergic symptoms may thus be achieved.

According to a preferred embodiment of the present invention the truncated molecule exhibits reduced T-cell reactivity.

In order to avoid or to significantly reduce late side effects the Fel d 1 derived hypoallergenic molecule exhibits reduced T-cell reactivity as defined in the present invention.

The truncated Fel d 1 is preferably composed of amino acids 1 to 34 or 35 to 70 of chain 1 of Fel d 1, amino acids 1 to 34, 35 to 63 or 64 to 92 of chain 2 of Fel d 1 or sequence variations thereof.

Another aspect of the present invention relates to hypoallergenic molecules being composed of or comprising amino acids 1 to 33, 21 to 51, 42 to 73, 62 to 103 or 98 to 129 of Der p 2, amino acids 1 to 30, 20 to 50, 50 to 80, 90 to 125, 125 to 155 or 165 to 198 of Der p 7, amino acids 1 to 35, 35 to 72, 70 to 100 or 90 to 122 of Der p 21, amino acids 1 to 32, 15 to 48 or 32 to 70 of Clone 30, amino acids 19 to 58, 59 to 95, 91 to 120 or 121 to 157 of Alt a 1, amino acids 31 to 60, 45 to 80, 60 to 96 or 97 to 133 of Par j 2, amino acids 1 to 40, 36 to 66, 63 to 99, 86 to 120 or 107 to 145 of Ole e 1, amino acids 25 to 58, 99 to 133, 154 to 183, 277 to 307, 334 to 363, 373 to 402, 544 to 573, 579 to 608, 58 to 99, 125 to 165, 183 to 224, 224 to 261, 252 to 289, 303 to 340, 416 to 457, 460 to 500 or 501 to 542 of Fel d 2, amino acids 19 to 58, 52 to 91, 82 to 119, 106 to 144 or 139 to 180 of Can f 2, amino acids 19 to 56, 51 to 90, 78 to 118, 106 to 145 or 135-174 of Can f 1, amino acids 27 to 70, 70 to 100 or 92 to 132 of Art v 1, amino acids 31 to 70, 80 to 120, 125 to 155, 160 to 200, 225 to 263, 264 to 300 305 to 350 or 356 to 396 of Amb a 1, amino acids 1 to 34, 35 to 74, 74 to 115, 125 to 165, 174 to 213, 241 to 280, 294 to 333, 361 to 400 or 401 to 438 of Alt a 6, amino acids 1 to 40, 41 to 80, 81 to 120, 121 to 160 of Alt a 2 or fragments or sequence variations thereof.

Another aspect of the present invention relates to a hypoallergenic fusion protein comprising at least two hypoallergenic molecules according to the present invention exhibiting reduced IgE-binding capacity and exhibiting optionally reduced T-cell reactivity.

The hypoallergenic molecules of the present invention which are derived from an allergen and lack IgE-binding capacity may be fused recombinantly or conjugated chemically to each other. As single components (allergen fragments) of the fusion protein/polypeptide also said fusion protein/polypeptide lacks IgE-binding capacity.

The fusion protein according to the present invention may comprise at least two, preferably at least three, more preferably at least four, even more preferably at least five, hypoallergenic molecules according to the present invention. It is, of course, also possible to fuse the hypoallergenic molecules to other peptides, polypeptides and proteins not derived from allergens. These peptides, polypeptides and proteins may when administered to an individual also induce an immunologic reaction or may act as a carrier or exhibit enzymatic activities. The hypoallergenic molecules in the fusion protein according to the present invention may be coupled directly to each other or via a linker which is preferably composed of amino acid residues.

Methods for the production of fusion proteins are well known in the art and can be found in standard molecular biology references such as Sambrook et al. (Molecular Cloning, 2nd ed., Cold Spring Harbor Laboratory Press, 1989) and Ausubel et al. (Short Protocols in Molecular Biology, 3rd ed; Wiley and Sons, 1995). In general, a fusion protein is produced by first constructing a fusion gene which is inserted into a suitable expression vector, which is, in turn, used to transfect a suitable hosT-cell. In general, recombinant fusion constructs are produced by a series of restriction enzyme digestions and ligation reactions which result in the desired sequences being incorporated into a plasmid. If suitable restriction sites are not available, synthetic oligonucleotide adapters or linkers can be used as is known by those skilled in the art and described in the references cited above. The polynucleotide sequences encoding allergens and native proteins can be assembled prior to insertion into a suitable vector or the sequence encoding the allergen can be inserted adjacent to a sequence encoding a native sequence already present in a vector. Insertion of the sequence within the vector should be in frame so that the sequence can be transcribed into a protein. It will be apparent to those of ordinary skill in the art that the precise restriction enzymes, linkers and/or adaptors required as well as the precise reaction conditions will vary with the sequences and cloning vectors used. The assembly of DNA constructs, however, is routine in the art and can be readily accomplished by a person skilled in the art.

According to a preferred embodiment of the present invention the molecules are fused to each other in an order differing from the order of the fragments in the wild-type allergen if the at least two molecules are derived from the same allergen.

The fusion protein according to the present invention may comprise at least two hypoallergenic molecules which are derived from the same wild-type allergen. In such a case the single molecules (allergen fragments) are fused to each other in an order differing from the order in the wild-type allergen. Such an approach prevents the re-formation of potential IgE-binding sites/epitopes in the hypoallergenic fusion protein.

Another aspect of the present invention relates to a nucleic acid molecule coding for a hypoallergenic molecule and a fusion protein according to the present invention.

The nucleic acid molecule of the present invention may be employed, e.g., for producing said molecules recombinantly.

Said nucleic acid molecule may—according to another aspect of the present invention—be comprised in a vector.

This vector is preferably an expression vector.

Another aspect of the present invention relates to a vaccine formulation comprising a hypoallergenic molecule, a fusion protein or an antibody according to the present invention.

The formulation further comprises preferably at least one adjuvant, pharmaceutical acceptable excipient and/or preservative.

The use of particular carrier substances such as KLH (keyhole Limpet Hemocyanin) is also among the latest current methods to increase immune responses. The hypoallergenic molecules of the present invention may also be fused or conjugated to viral capsid proteins which may act also as a carrier (see above).

According to a preferred embodiment of the present invention said formulation comprises 10 ng to 1 g, preferably 100 ng to 10 mg, especially 0.5 µg to 200 µg of said hypoallergenic molecule or antibody.

The vaccine formulation may be substantially composed as the medicament of the present invention (see above).

Another aspect of the present invention relates to the use of a hypoallergenic molecule, a fusion protein, or an antibody according to the present invention for manufacturing a medicament for the treatment or prevention of an allergy in an individual.

The hypoallergenic molecule, fusion protein and antibody according to the present invention may be used for vaccination of an individual. This vaccination may reduce or prevent the allergic response caused by a wild-type allergen.

According to a preferred embodiment of the present invention said medicament further comprises at least one adjuvant, pharmaceutical acceptable excipient and/or preservative.

The medicament according to the present invention comprises preferably 10 ng to 1 g, preferably 100 ng to 10 mg, especially 0.5 µg to 200 µg of said immunogenic molecule, nucleic acid molecule, vector, host or antibody.

According to another preferred embodiment of the present invention the medicament is administered to an individual in the amount of 0.01 mg/kg body weight to 5 mg/kg body weight, preferably 0.1 mg/kg body weight to 2 mg/kg body weight.

According to a preferred embodiment of the present invention said individual is at risk to get an allergy.

Another aspect of the present invention relates to the use of a hypoallergenic molecule, a fusion protein or an antibody according to the present invention for diagnosing an allergy or monitoring the progress of an allergy therapy in an individual.

The hypoallergenic molecule, fusion protein or antibody according to the present invention may not only be used in medicaments but can also be suitably employed for various diagnostic purposes. For instance, these molecules and fusion proteins may be used for diagnosing an allergy by exposing, e.g., a sample of an individual comprising histamine releasing cells to said polypeptide (see, e.g., Purohit et al., Clin. Exp. Allergy 35 (2005): 186-192). Furthermore, these molecules, fusion proteins and antibodies may be immobilized on a surface in order to form a polypeptide array/chip. Such arrays may be used, e.g., in high throughput screening in order to diagnose an allergy in a number of samples taken from a number of individuals.

The present invention is further illustrated by the following figures and examples, however, without being restricted thereto.

FIGS. 1B and 1C show the DNA sequence of the multiple cloning site of the pET-17b vector and the 89VP1 encoding gene.

Figure 3:
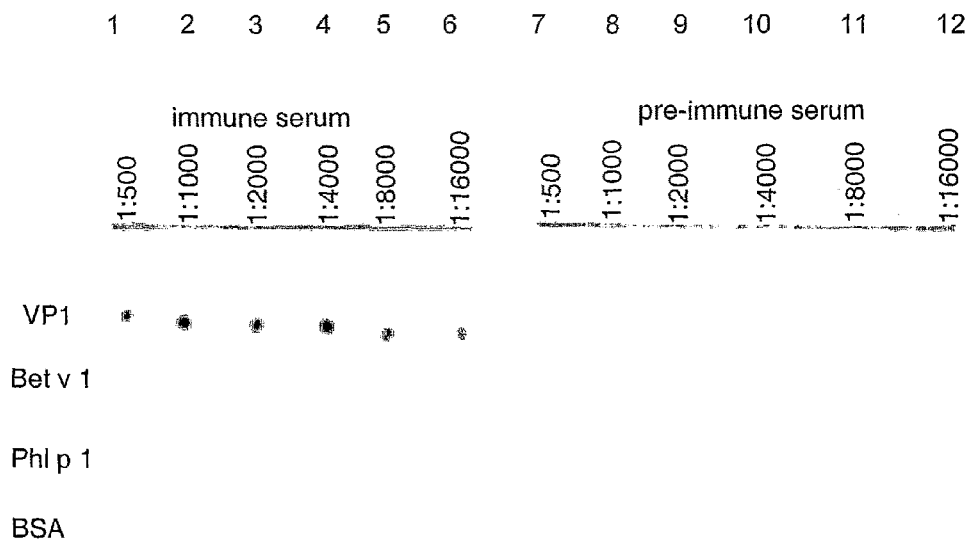

FIG. 3 shows IgG recognition of 14VP1: Immunoblotting of 14VP1 and controls. Dots are visualized by autoradiography (Lane 1-6: Incubation with 1:500-1:16000 diluted rabbit anti-14VP1 antiserum; Lane 7-12: Incubation with 1:500-1:16000 diluted preimmune serum).

Figure 4:
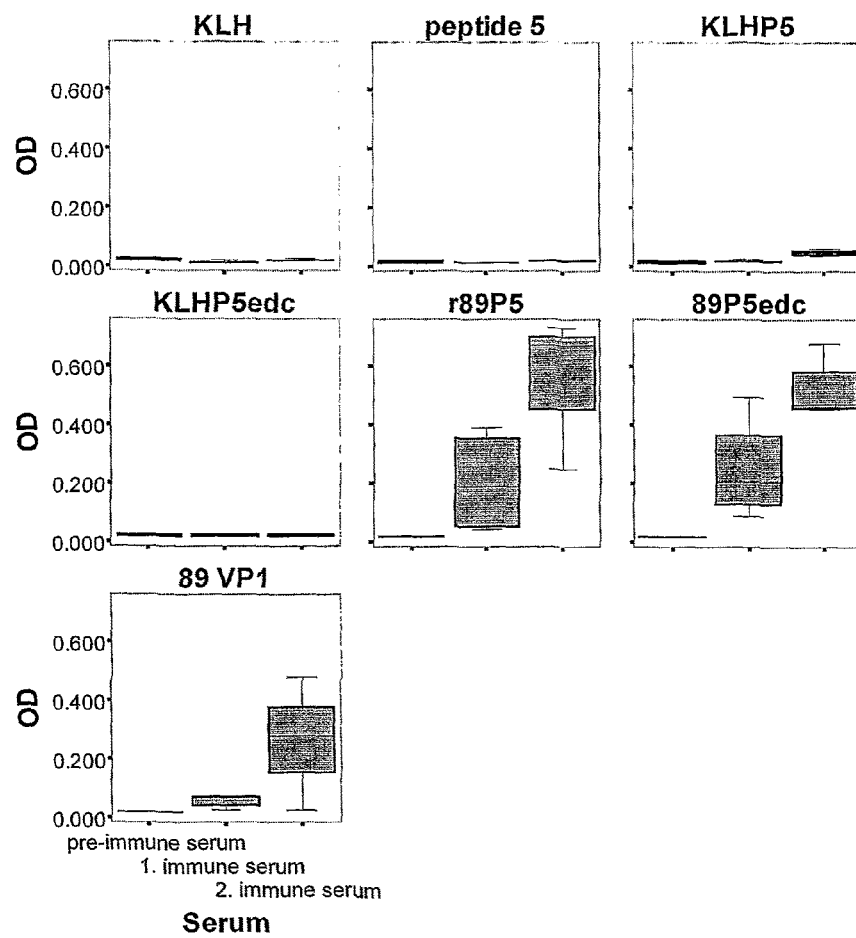

FIG. 4 shows 89VP1-specific IgG1 response in mice. Groups of mice were immunized with different antigens as indicated on top of each box. 89VP1-specific IgG1 titers were measured by ELISA and are expressed as OD values on the y-axis. The results are shown as box plots, where 50% of the values are within the boxes and non-outliers between the bars. The line within the boxes indicates the median values.

Figure 5:
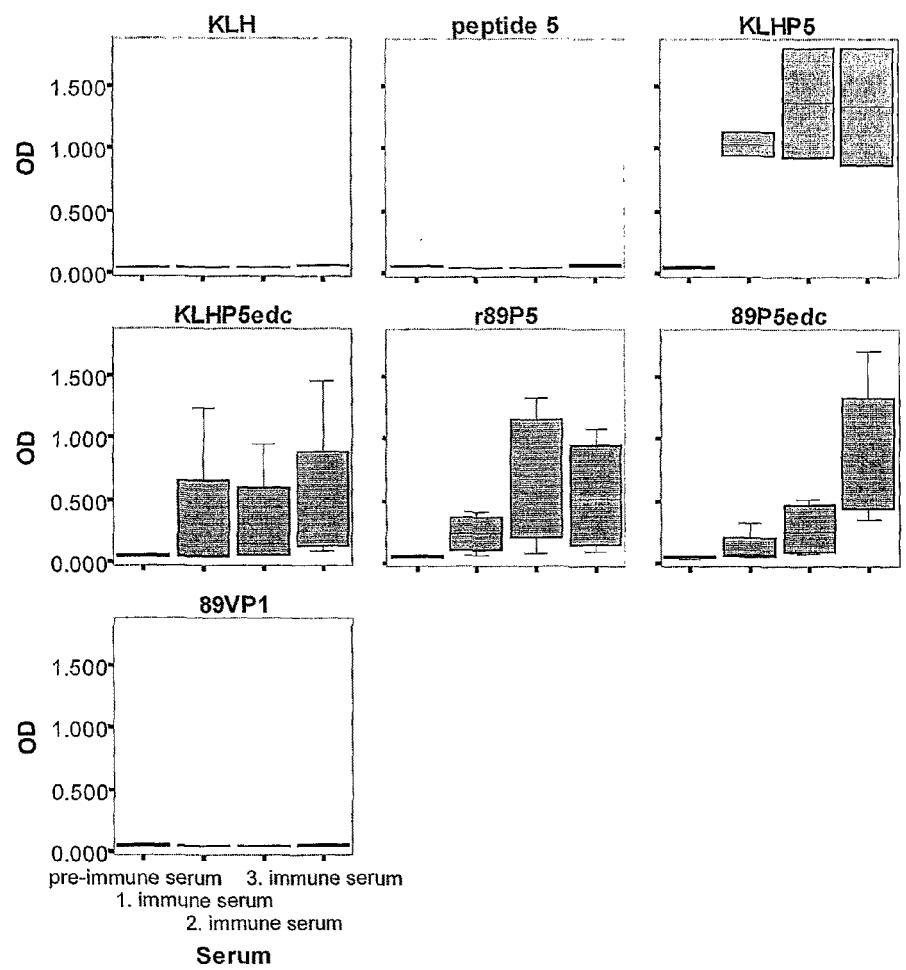

FIG. 5 shows Phl p 1-specific IgG1 response in mice. Groups of mice were immunized with different antigens as indicated on top of each box. rPhl p 1-specific IgG1 titers were measured by ELISA and are expressed as optical value (OD 405 nm) on the y-axis. The optical value corresponds to the level of IgG1 antibody in the mouse sera. The results are shown as box plots were 50% of the values are within the boxes and non-outliers between the bars. The line within the boxes indicates the median values.

Figure 6:
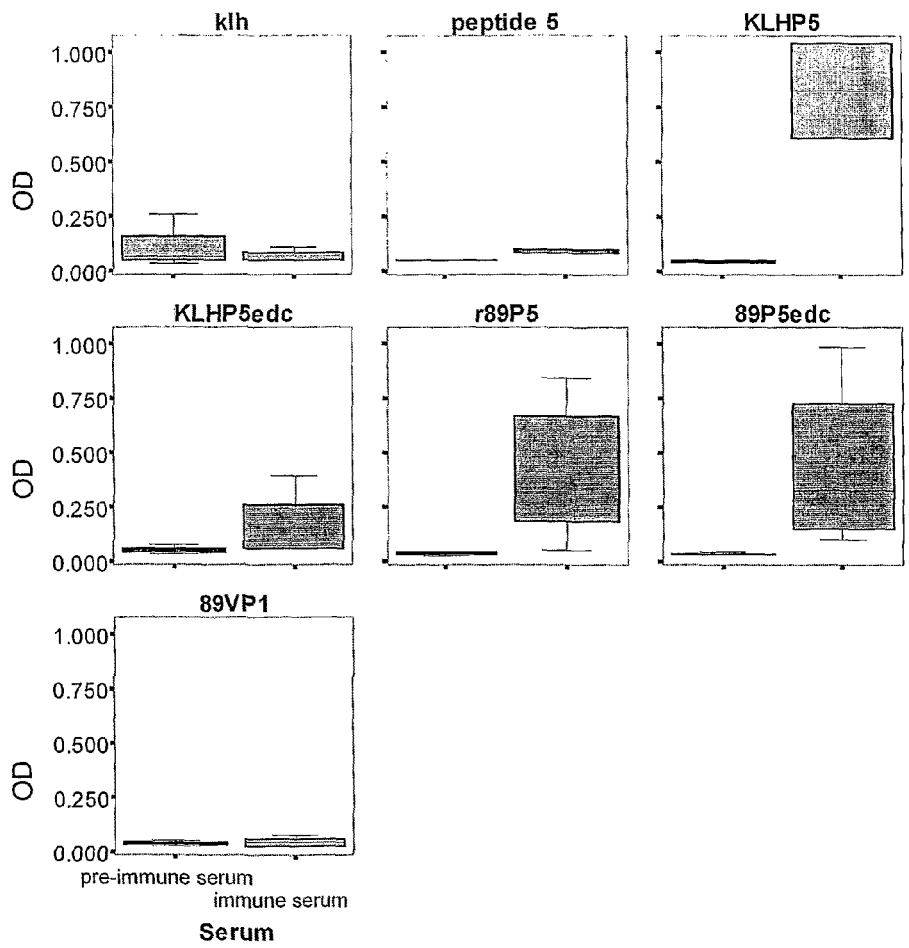

FIG. 6 shows Timothy grass pollen extract-specific IgG1 response in immunized mice. Groups of mice were immunized with different antigens as indicated on top of each box. Timothy grass pollen extract-specific IgG1 titers were measured by ELISA and are expressed as optical value (OD 405 nm) on the y-axis. The optical value corresponds to the level of IgG1 antibody in the mouse sera. The results are shown as box plots, where 50% of the values are within the boxes and non-outliers between the bars. The line within the boxes indicates the median values.

Figure 7:
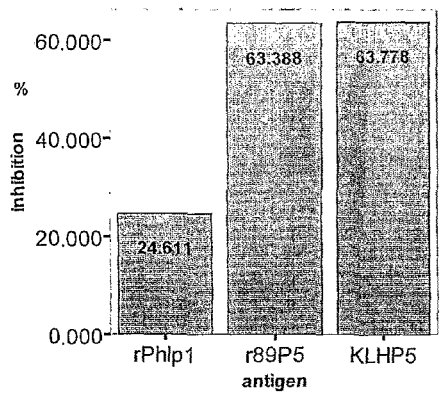

FIG. 7 shows the mean of % inhibition of patient's IgE-binding to rPhl p 1 by preincubation with antisera against rPhl p 1, r89P5 and KLHP5 of all 19 patients. The % inhibition is shown on the y-axis. The results are shown as bars.

Figure 8:
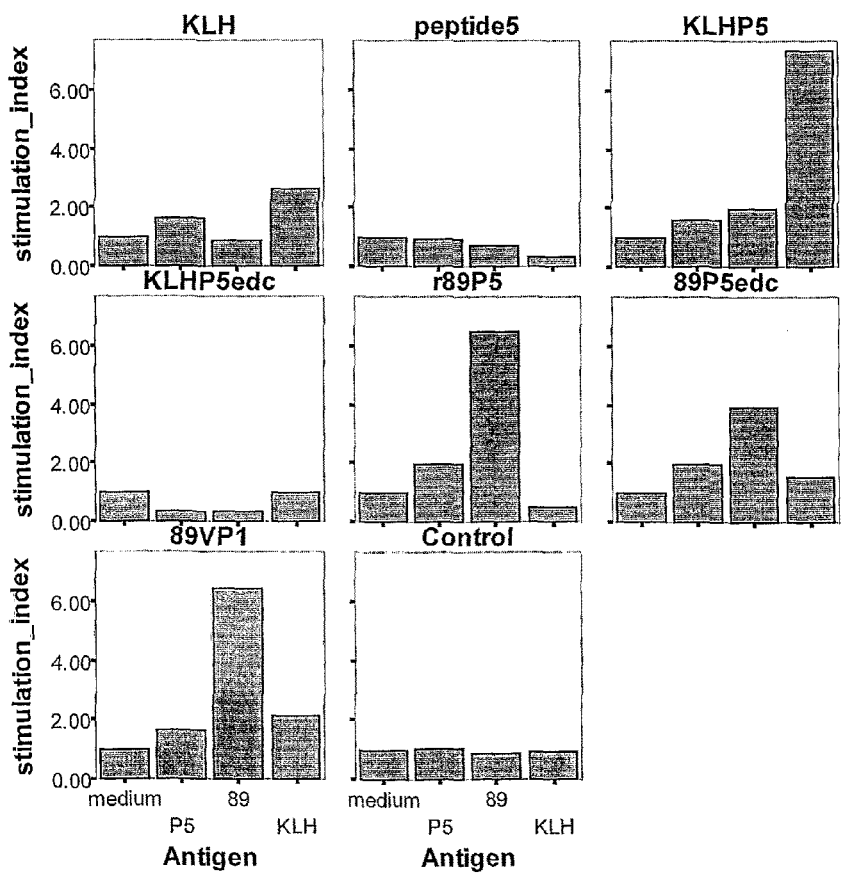

FIG. 8 shows the proliferation of spleen cells of immunized mice. T-cells of immunized mice with different antigens as indicated on top of each box were stimulated with peptide 5, 89VP1(89) and KLH. Medium was used as a reference. At the y-axis the stimulation index is shown. The results are displayed in bars.

Figure 9:
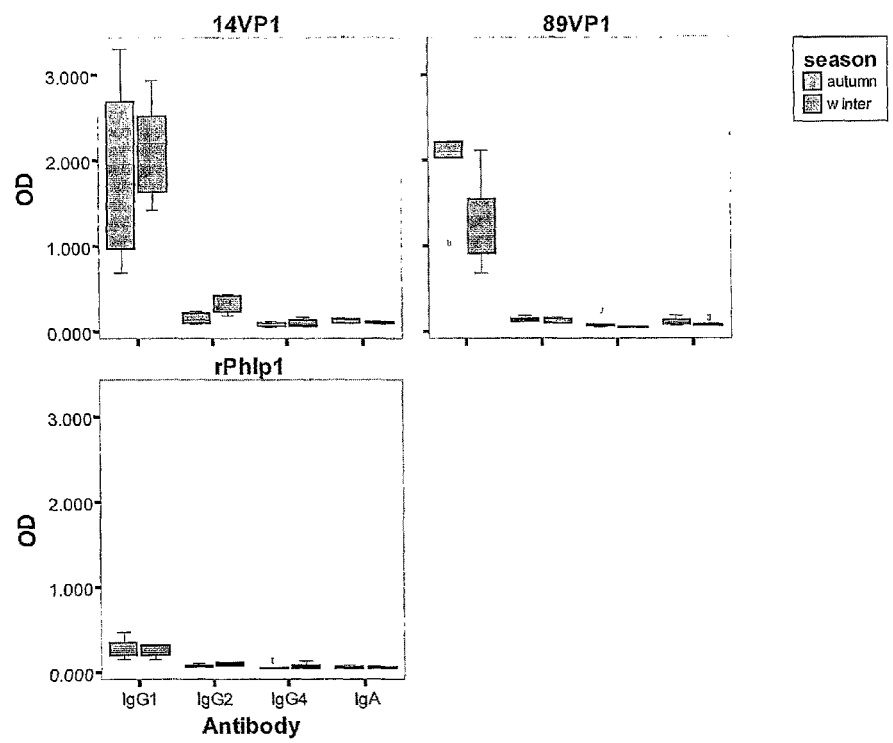

FIG. 9 shows IgG1, IgG2, IgG4 and IgA response to 14VP1, 89VP1 and rPhl p 1 detected in human sera by ELISA measurement. 10 patient's sera were tested for four antibodies specific for 89VP1, 14VP1 and rPhl p 1 as indicated on top of each box. Sera taken in autumn and winter are shown on the left hand and right hand of each "bar pair", respectively. Titers were measured by ELISA and are expressed as optical value (OD 405 nm) on the y-axis. The optical value corresponds to the level of antibody in the human sera. The results are shown as box plots, where 50% of the values are within the boxes and non-outliers between the bars. The line within the boxes indicates the median values.

Figure 10:
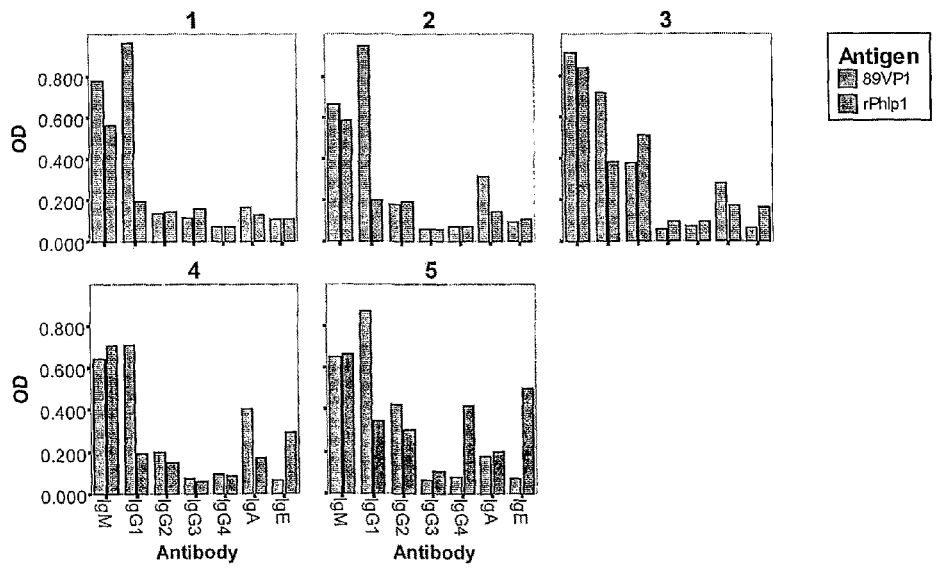

FIG. 10 shows the detection of anti-89VP1 and anti-rPhl p 1 antibodies in sera of allergic patients. 5 Phl p 1 allergic patient's sera were tested for seven antibodies specific for 89VP1 (left bar of each pair) and rPhl p 1 (right bar of each pair). Titers were measured by ELISA and are expressed as optical value (OD 405 nm) on the y-axis. The optical value corresponds to the level of antibody in the human sera. The results are shown as box plots, where 50% of the values are within the boxes and non-outliers between the bars. The line within the boxes indicates the median values.

Figure 11:
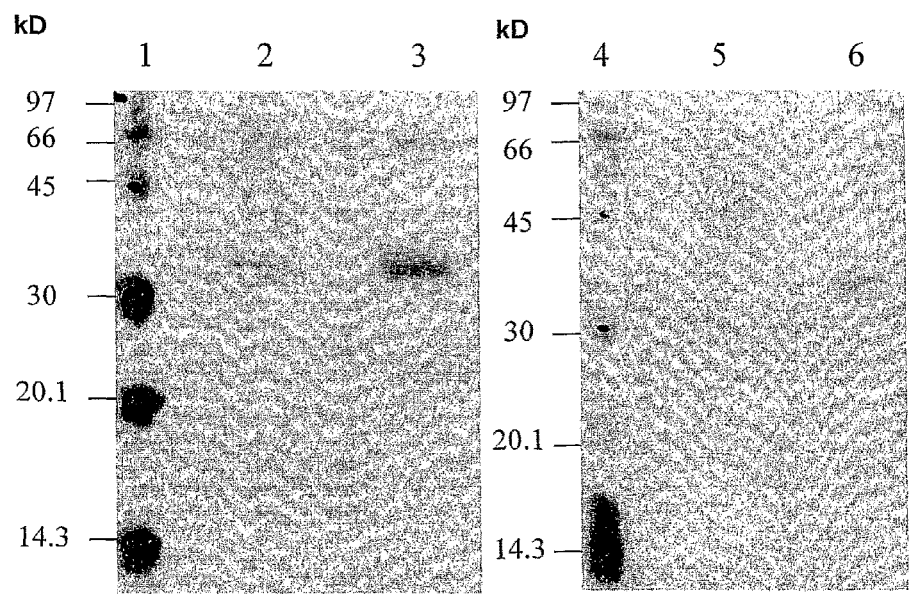

FIG. 11 shows anti-14VP1 IgG binding to HRV14 protein extract and purified 14VP1 (Lane 1 and 4: 5 μg Marker; lane 2 and 4: Virus extract; lane 2 and 5: 5 μg 14VP1). Blot A und B was incubated with anti-14VP1 immune serum and preimmune serum, respectively. Bound IgG was detected by Western blotting and visualized by autoradiography.

Figure 12:
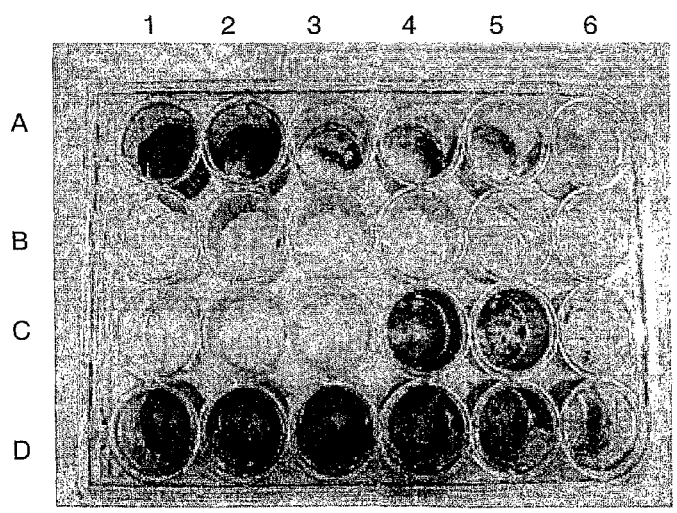
Figure 12A:
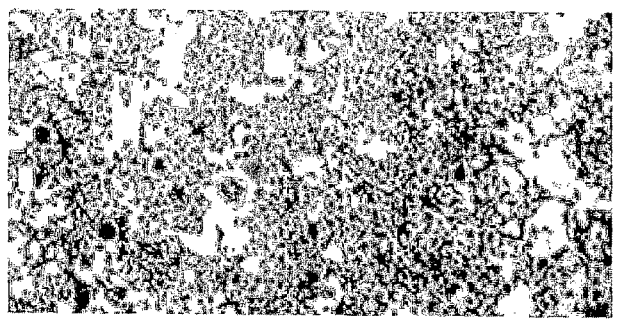
Figure 12B:
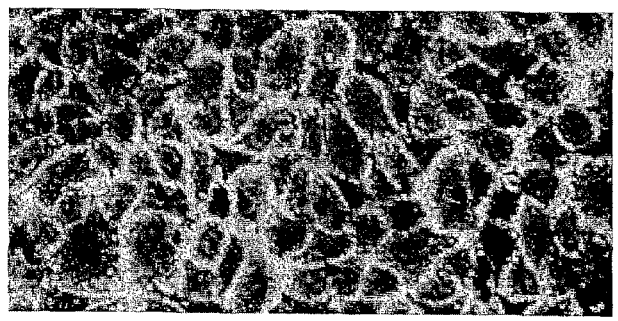

FIG. 12 shows the neutralization of HRV14 (Lane A (cell control): Cells after preincubation of HRV14 with a dilution of anti-14VP1 immune serum $1:10^2$-$1:10^8$ (row A1-A6); Lane B: Cells after preincubation of HRV14 with a dilution of preimmune serum $1:10^2$-$1:10^8$ (row B1-B6); Lane C: cells after Incubation with HRV14 10 TCD50-$10^6$ TCD50 (row C1-C6); D5: cells after incubation with preimmune serum; D6: cells after incubation with immune serum). Cells were plated out in all wells and colored with crystal violet after three days.

Figure 13:
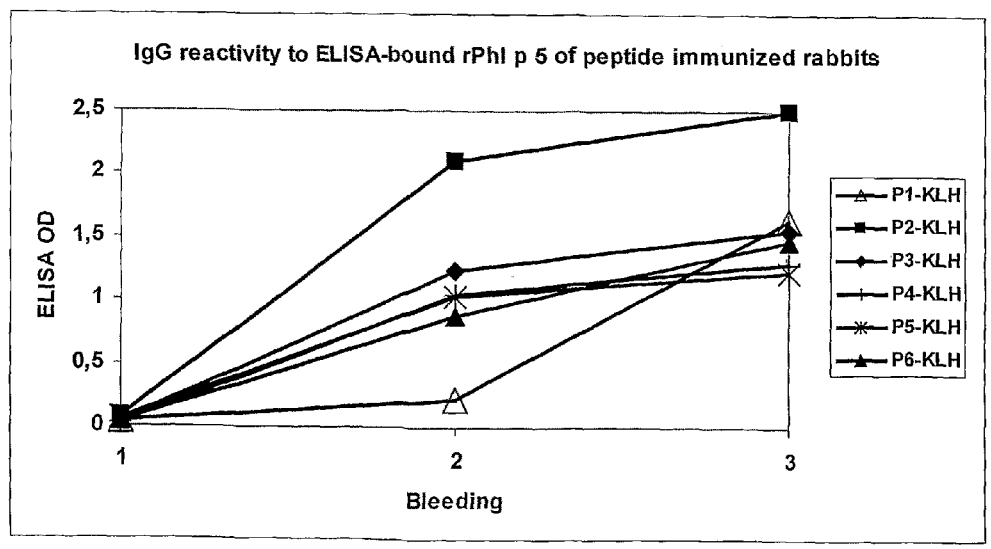

FIG. 13 shows IgG reactivity of anti-peptide antisera with the complete Phl p 5 allergen. IgG reactivities (OD values) to Phl p 5 are shown for 3 serum samples (bleeding 1: preimmune serum; bleedings 2-3: serum samples collected in monthly intervals) obtained from 6 rabbits, each of which was immunized with one of the KLH-conjugated peptides.

Figure 14:
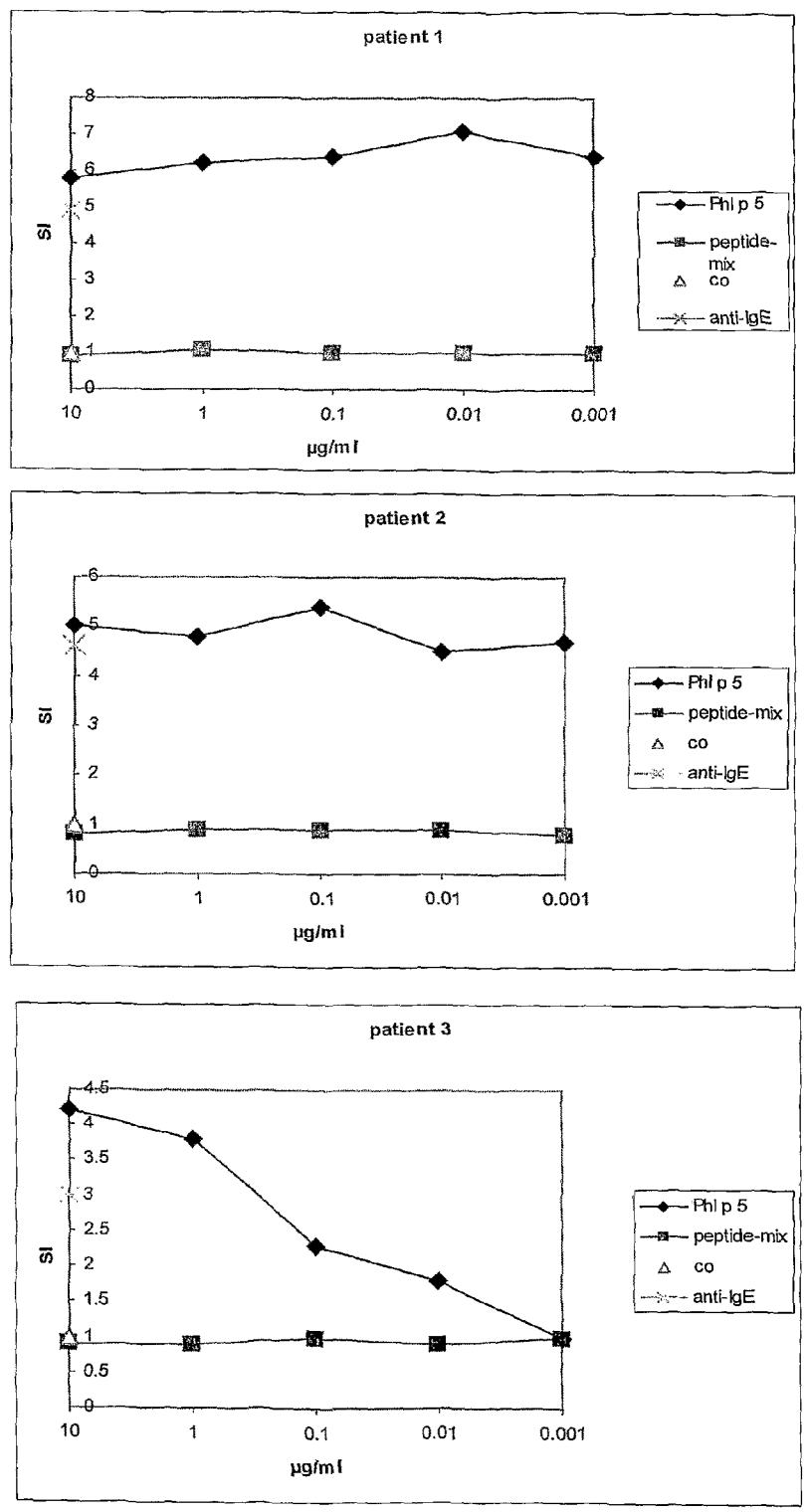

FIG. 14 shows allergenic activity of rPhl p 5, and the peptide mix as detected by CD203c expression. Heparinized blood samples from three patients allergic to Phl p 5 were incubated with serial dilutions from $10^{-4}$ to 10 μg/mL of recombinant allergen, an equimolar mix of Phl p 5 derived peptides, anti-IgE or control buffer (co, x-axis). Cells were then stained with CD203c mAb and analyzed for CD203c expression on a FACScan. The stimulation index (SI) is displayed on the y-axis.

Figure 15:
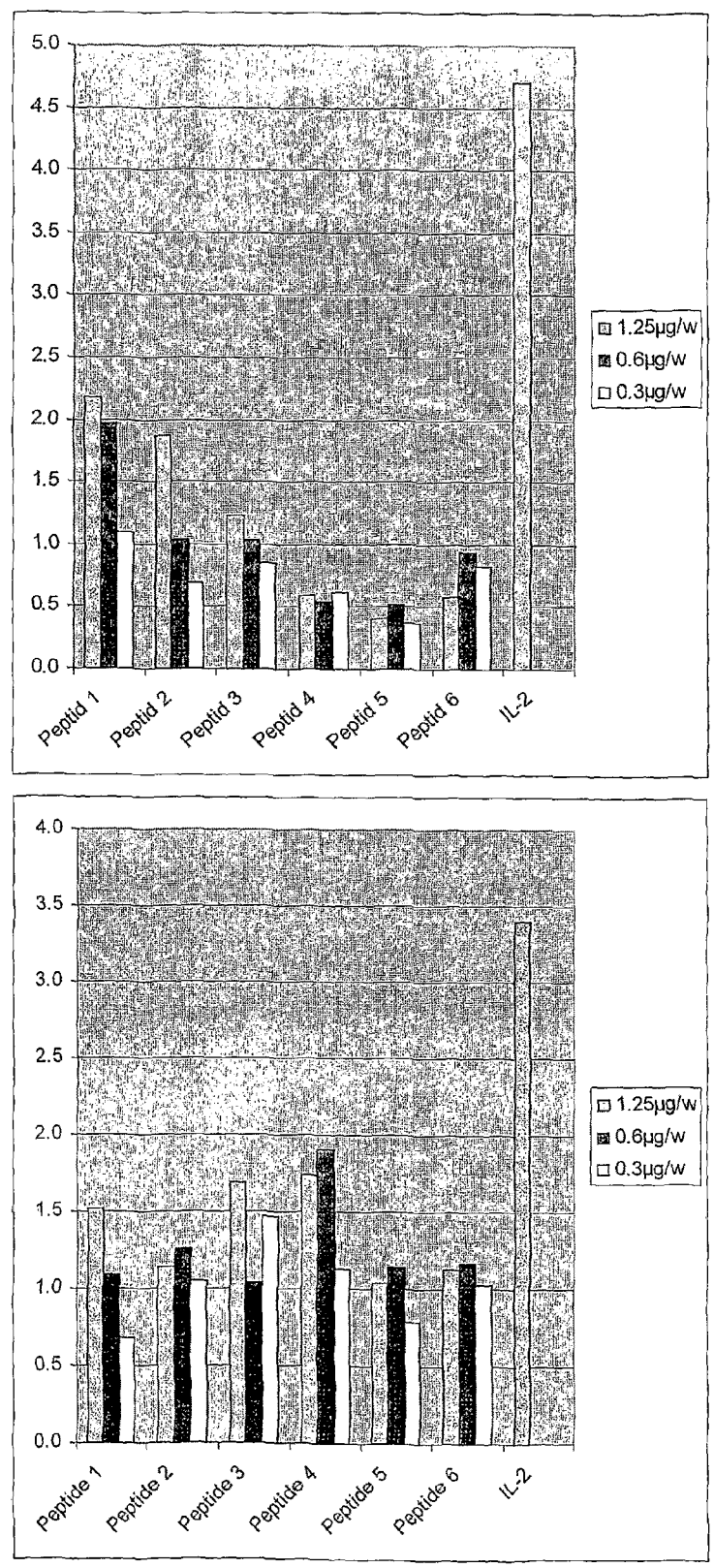

FIG. 15 shows identification of Phl p 5-derived peptides which induce low lymphoproliferative responses. PBMCs from timothy pollen allergic patients were stimulated with different concentrations of peptides and, for control purposes, with interleukin-2 (x-axis). Stimulation indices (SI) are indicated on the y-axis.

Figure 16:
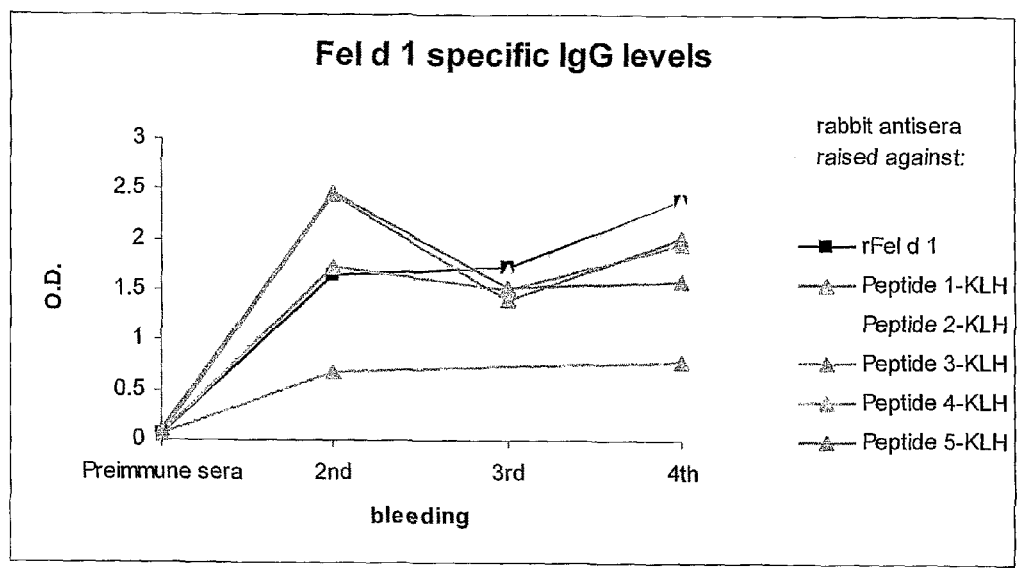

FIG. 16 shows Fel d 1-derived synthetic peptides which induce Fel d 1 specific IgG immune responses in rabbits. Six rabbits were immunized with the KLH-conjugated Fel d 1-derived synthetic peptides or unconjugated rFel d 1 and 3-4 bleedings were drawn in monthly intervals. IgG reactivities of the preimmune sera and the antisera to ELISA plate-bound rFel d 1 are shown as optical densities (O.D. values, y-axis).

Figure 17:
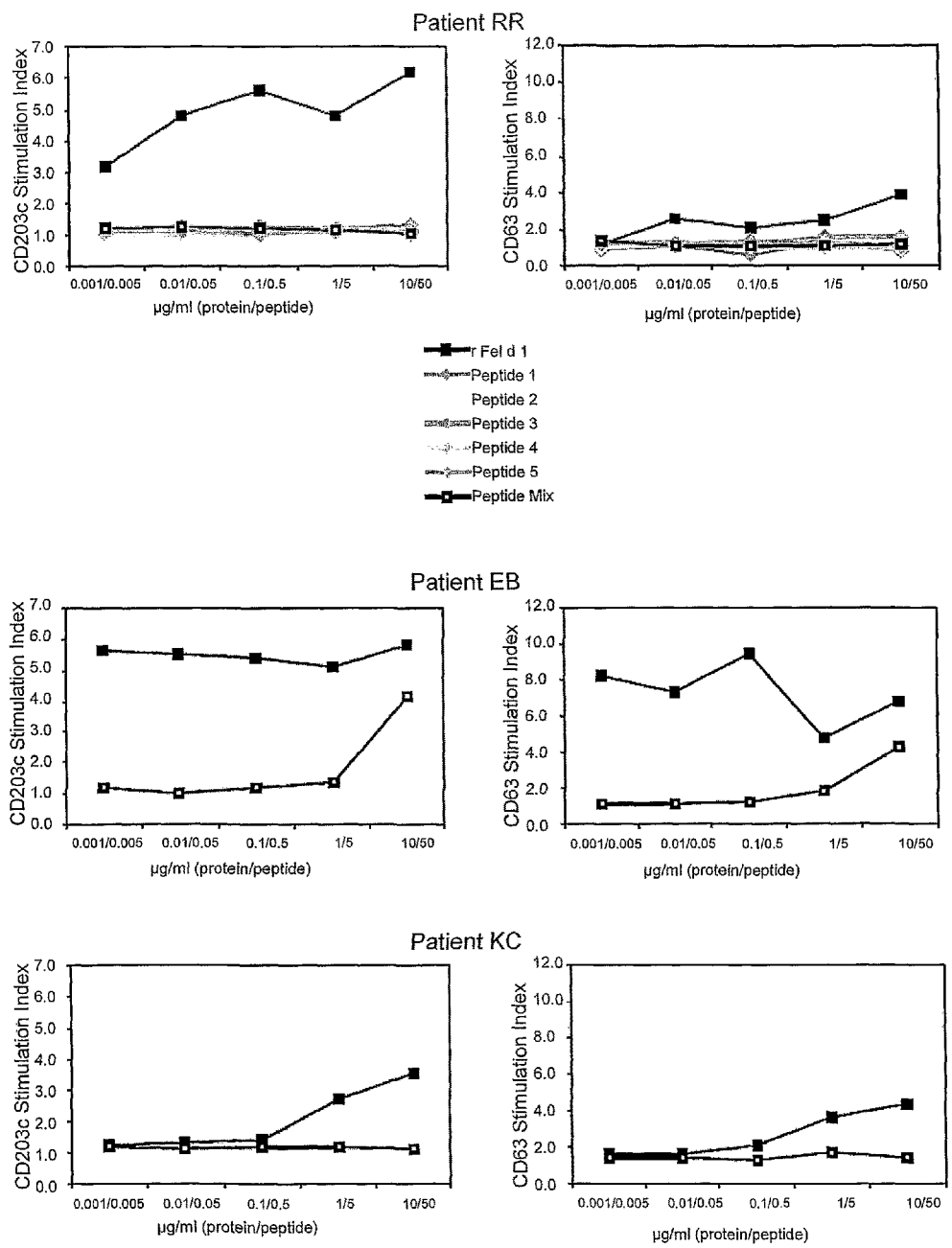

FIG. 17 shows the low allergenic activity of Fel d 1-derived synthetic peptides as determined by CD63 and CD203c expression on basophils of allergic patients. PBMCs from 5 cat allergic patients were incubated with serial dilutions of Fel d 1 (closed boxes) or a mixture of Fel d 1-derived synthetic peptides (open boxes) (x-axis). For patient RR PBMCs were also probed with serial dilutions of Fel d 1-derived synthetic peptides as single components. Induction of expression of surface markers CD203c and CD63 was measured as mean fluorescence intensities, and calculated stimulation indices are shown on the y-axis.

Figure 18:
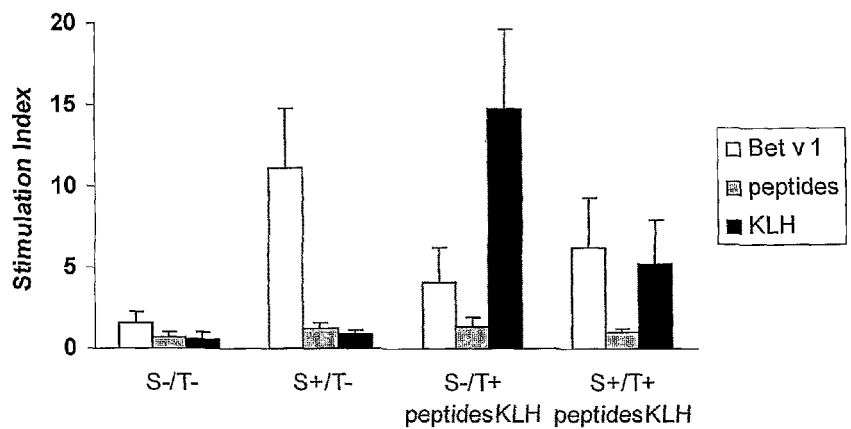

FIG. 18 shows that a treatment with KLH-coupled Bet v 1-derived peptides reduces lymphoproliferative responses to rBet v 1 in sensitized mice. T-cell proliferation was measured in spleen cell cultures after in vitro stimulation with the recombinant birch pollen allergen Bet v 1 (white bars), KLH (black bars), or the peptide mix (grey bars). The bars represent the mean stimulation indices (SI±SD) for the different groups of mice.

Figure 19:
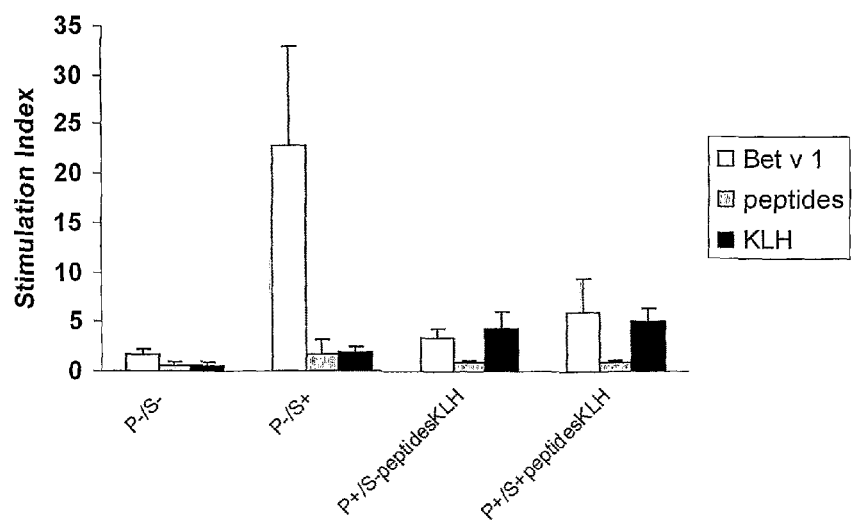

FIG. 19 shows the prophylactic vaccination of naive mice with KLH-coupled Bet v 1-derived peptides which reduces lymphoproliferative responses to rBet v 1 after sensitization.

Figure 20:
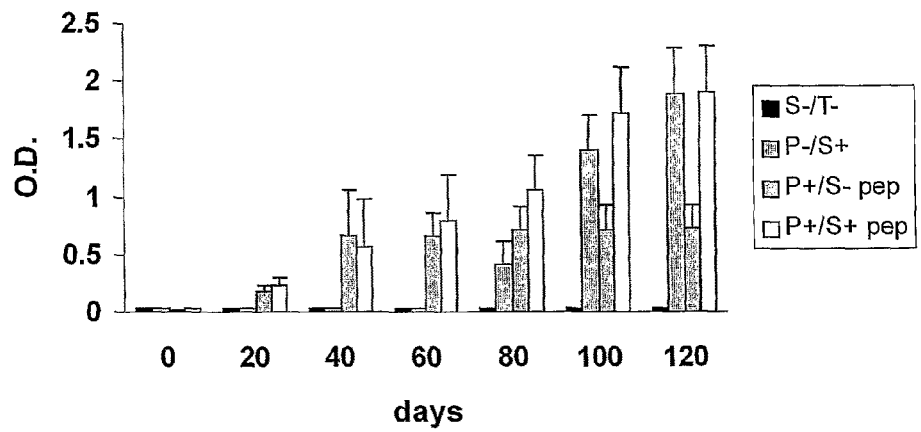

FIG. 20 shows that the prophylactic vaccination of naive mice with KLH-coupled Bet v 1-derived peptides induces a Bet v 1-specific IgG response and primes for the induction of allergen-specific IgG responses by the complete allergen. IgG responses (OD values: y-axis) to Bet v 1 were measured in the four treatment groups at different points of time (x-axis).

Figure 21:
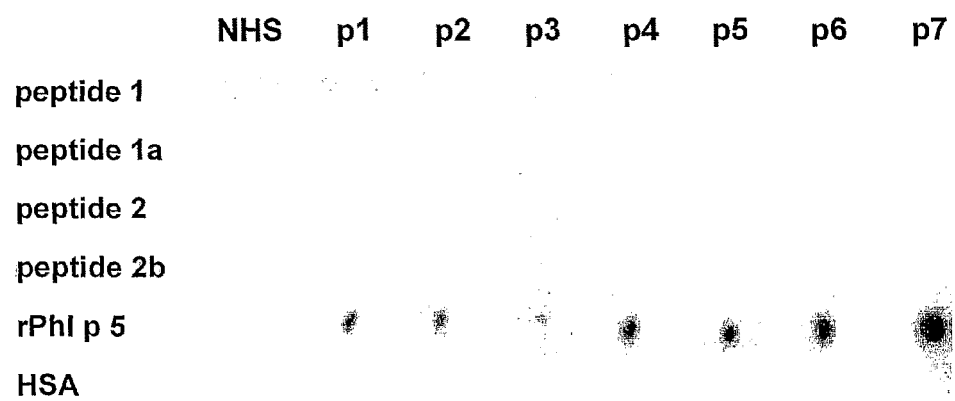

FIG. 21 shows a comparison of IgE-reactivity: IgE binding capacity of Phl p 5 derived peptides (1, 2) and variants (1a, 2b) was determined in dot blot assays applying 0.2 □g/dot using sera from 7 grass-pollen allergic patients (p1-p7) and the serum from a non-atopic individual (NHS). rPhl p 5 was used as positive control and HSA as negative control. Bound IgE was detected with 125 I-labelled anti-human IgE.

Figure 22:
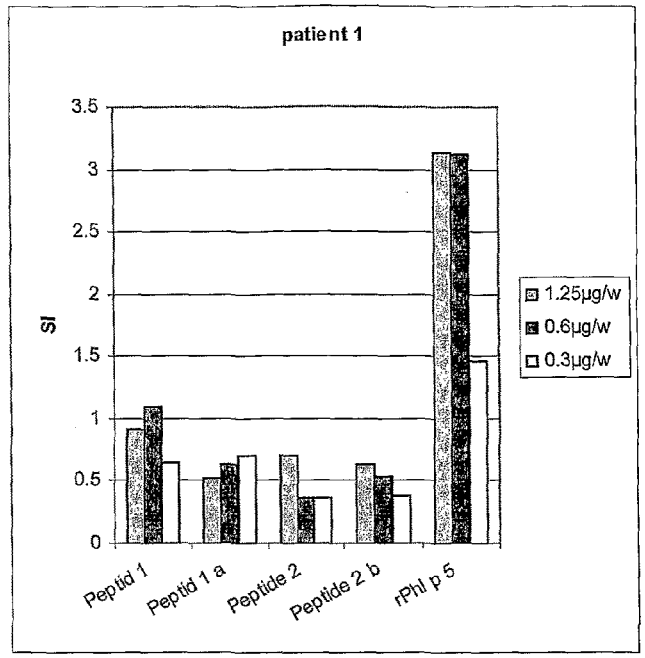
Figure 22:
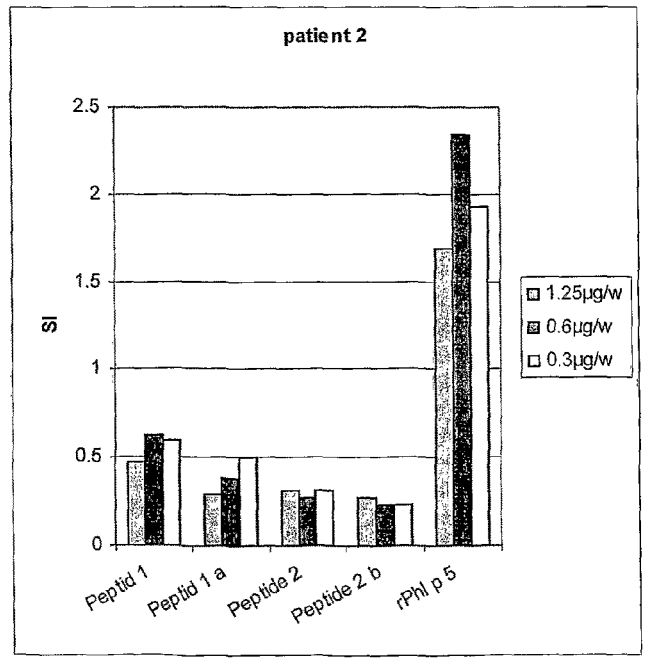

FIG. 22 shows a lymphoproliferative responses of Phl p 5 derived peptides (1, 2) and variants (1a, 2b). PBMCs from grass pollen allergic patients were stimulated with different concentrations of peptides and, for control purposes, with equimolar concentrations of rPhl p 5. Stimulation indices (SI) are indicated on the y-axis.

Figure 23:
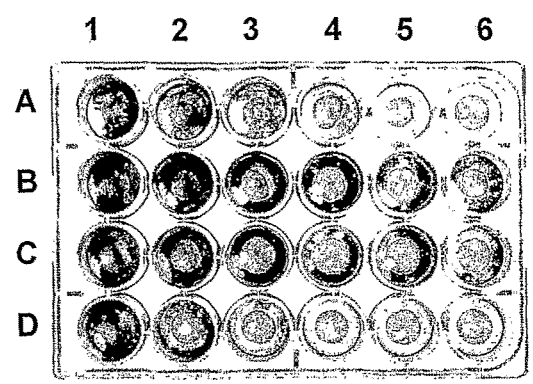

FIG. 23 shows the cross protection of anti VP1 antibodies.

EXAMPLES

Example 1

Construction of Vector p89VP1

Virus stock samples were prepared for RT-PCR by addition of 1 μl of RNase inhibitor (Boehringer GmbH, Germany) to a final concentration of 0.01 U/μl after RNA extraction from cell culture supernatants by QIAamp viral RNA kit (Qiagen, Germany).

Plasmid p89VP1 (FIG. 1A) was constructed by replacing the NdeI/EcoRI fragment of the multiple cloning site of pET-17b with the cDNA sequence encoding for the VP1 protein of human rhinovirus strain 89 (89VP1). The NdeI and EcoRI restriction sites (in pET-17b) were used for insertion of AseI/EcoRI linked 89VP1 with ATG at the 5' end, six histidin followed by the stop-codon TGA at the 3' end (FIG. 1B).

The insertion of 89VP1 in pET-17b was confirmed by nucleotide sequencing.

After NdeI/AseI fusion instead of the NdeI site CATAAT was created and could not be cut with any available enzyme. Therefore, the site was mutated to CTTAAG, the restriction site of Afl II. To insert a further allergen fragment, the ACCGTT sequence at the 3' end was mutated to ACCGGT, the restriction site of AgeI. The amino acid sequences are displayed below the nucleotide sequences of 89VP1. The restriction sites are shown underlined in FIG. 1B.

Figure 1A:
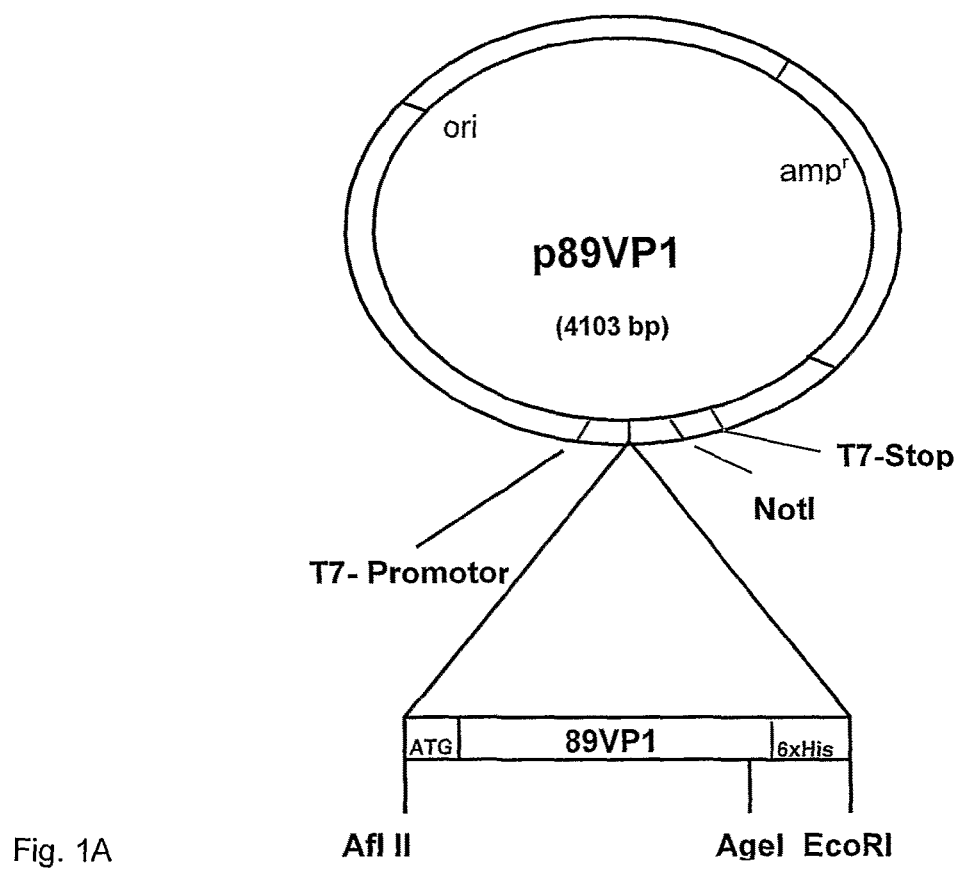
FIG. 1A shows a schematic overview of the vector p89VP1.
Figure 1D:
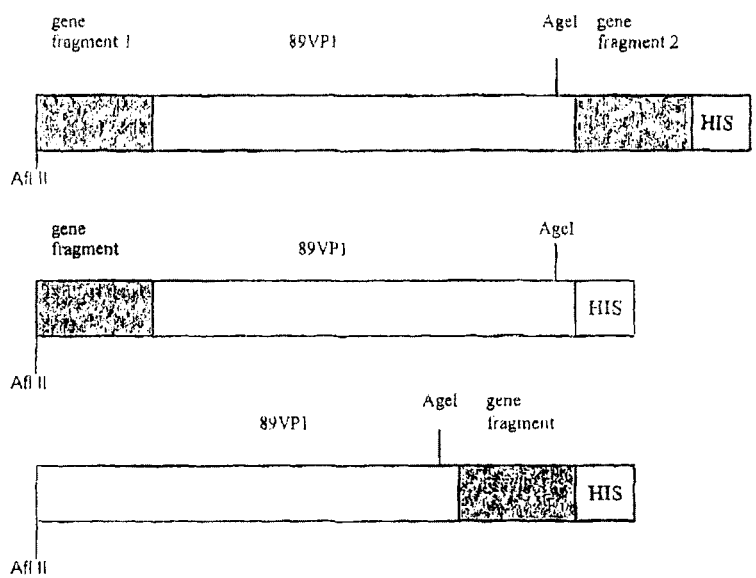
FIG. 1D shows the schematic representation of three possibilities for creating nucleic acid fusions.
Figure 2:
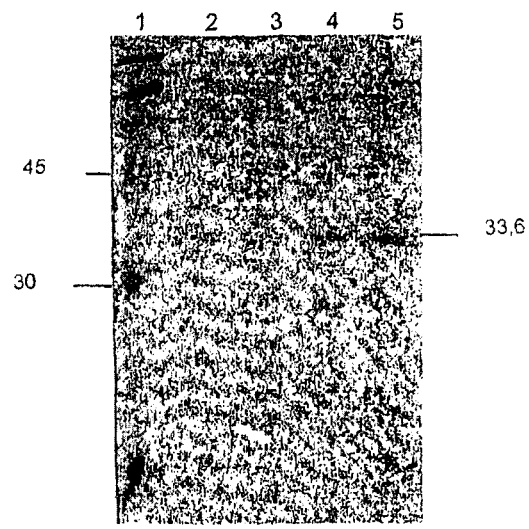
FIG. 2 shows a Coomassie blue stained 12% SDS-PAGE gel containing purified 89VP1 his-tagged protein (Lane 1: 5 µg molecular marker; Lane 2-5: 10 µl 89VP1 elution samples).

Said Afl II and AgeI restriction sites were created with the Quick change site mutagenesis Kit (Stratagene).

cDNAs for gene fragments can thus be inserted for easy purification into the remaining restrictions sites either at the 5' end (using Afl II) or at the 3' end (using AgeI) of 89VP1 or into both sites as indicated in FIG. 1C. Recombinant allergen fragments will thus be expressed at the N-terminus and/or the C-terminus of the 89VP1.

TABLE I

Cloning and mutagenesis primers (5' to 3')

| 89VP1 cloning | | SEQ ID No. |
|---|---|---|
| 89VP1 forward | CGGAATTCATTAATATGAACCCAGTTGAAAAT-TATATAGATAGTGTATTA | 1 |
| 89VP1 reverse | CGATTAATTCAGTGGTGGTGGTGGTGGTG-GACGTTTGTAACGGTAA | 2 |
| Mutagenesis | | |
| Afl II forward | CTTTAAGAAGGAGATATACTTAAGATGAAC-CCAGTTG | 3 |
| Afl II reverse | CAACTGGGTTCATCTTAAGTATATCTCCTTCT-TAAAG | 4 |
| AgeI forward | CCTGATGTTTTTACCGGTACAAACGTCCACCAC | 5 |
| AgeI reverse | GTGGTGGACGTTTGTACCGGTAAAAACATCAGG | 6 |

Example 2

Cloning of a Construct Expressing a 89VP1-Allergen Fragment Fusion Protein

The approach described above was exemplified for a C-terminal Phl p 1 allergen fragment, namely peptide 5 (CVRYT-TEGGTKTEAEDVIPEGWKADTAYESK; M. Focke et al. FASEB J (2001) 15:2042-4). The peptide 5 DNA sequence was amplified by PCR using the Phl p 1 cDNA (GenBank: X78813) as a template (Primers: Phl p 1 forward 5'-CGCGCTTAAGATGGTCCGCTACACCAC-CGAGGGC-3' (SEQ ID No. 7); Phl p 1 reverse 5'-CGCGCTTAAGCTTGGACTCGTAGGCGGTGTCGGC-3' (SEQ ID No. 8)). The PCR product was inserted into the Afl II restriction site of the p89VP1 vector, and the resulting construct is referred to as vector p89P5 and gene product r89P5.

Example 3

Expression and Purification of 89VP1 Peptide 5-Fusion Protein and 89VP1

In order to achieve expression of 89VP1 or r89P5 (recombinant 89VP1-peptide 5 fusion protein), plasmids were transformed into *E. coli* BL21 (DE3). Transformed *E. coli* cells were grown in 250 ml LB medium containing 100 mg/l ampicillin at 37° C. to an optical density (600 nm) of 0.4, and protein expression was induced by addition of isopropyl-beta-D-thiogalactosidase (IPTG) to a final concentration of 1 mM. *E. coli* cells were harvested after 4 hours by centrifugation at 3500 rpm at 4° C. for 10 min. Purification was performed with the Qiagen protocol using Qiagen Ni-NTA and columns. The cell pellet was resuspended under denaturing conditions in 5 ml 6 M guanidinium hydrochloride for 1 hour. After centrifugation (20 min, 10000×g) the supernatant was incubated with 1 ml Ni-NTA for an additional hour. The suspension was then loaded on a column, washed twice with 5 ml wash buffer (8 M urea pH 6.3) and then eluted with 4 ml elution buffer (8 M urea pH 3.5). Renaturation was achieved after dialysis with decreasing molarity of urea.

Purity and size of the purified protein were analyzed by SDS-PAGE as shown in FIG. 2. Protein bands correlated with the calculated protein size of 33.6 kD. Integrity of the proteins was also confirmed by Western blot analysis, using anti-histidine tag antibody.

Example 4

Detection of 14VP1-Specific Rabbit Antibodies by Immunoblotting

5 μg 14VP1 (VP1 protein of the human rhinovirus strain 14) and controls (Bet v 1, Phl p 5, BSA) were dotted onto nitrocellulose membrane strips. These strips were exposed to a dilution of rabbit anti-14VP1 antiserum (lane 1-6) and pre-immune serum (lane 8-12). Bound rabbit IgG antibodies were detected with 125I-labeled donkey anti-rabbit IgG 1:1000 and visualized by autoradiography (FIG. 3).

Dot blot analysis of rabbit anti-14 VP1 serum shows that 14VP1 is strongly immunogenic. IgG antibodies were still detected with a 1:16000 dilution of the antiserum in contrast to the preimmune serum and the Bet v 1, Phl p 5 and BSA controls.

Example 5

89VP1-Specific Antibody Response in Immunized Mice Determined by ELISA

In order to determine the immunogenicity of 89VP1 and its ability to act as a carrier for peptide 5, groups of six week old female balb/c mice (Charles River) were immunized with the following antigens: KLH, KLH maleimide coupled peptide 5 (KLHP5) and KLH EDC coupled peptide 5 (KLHP5edc). The chemical coupling was made with the Imject maleimide activated mcKLH and Imject Immunogen EDC Kit (Pierce). The maleimide group reacts with SH groups and the EDC reacts with carboxyl and amino groups to form stable bonds. Groups of 4 mice were immunized with 89VP1, r89P5 and 89P5edc and 2 mice were immunized with peptide 5 only (5 μg each and mixed 1:2 with aluminium hydroxide). The mice were immunized subcutaneously in approximately three-week intervals and bled from the tail veins. The 89VP1-specific IgG1 antibody level was determined by ELISA.

ELISA plates (Nunc) were coated with 5 μg/ml 89VP1. The mice anti-89VP1, anti-r89P5 and peptide 5 sera were diluted 1:500. Bound IgG1 was detected with rat anti-mouse IgG1 (BD Pharmingen) 1:1000 and then with goat anti rat IgG POX-coupled (Amersham Bioscience) 1:2000. The optical value (OD 405 nm) is displayed on the y-axis and corresponds to the level of IgG1 antibody in the mouse sera (FIG. 4).

KLHP5, KLHP5edc, KLH and peptide 5 were used as controls. IgG1 antibodies were detected with an increasing titer during immunization in mice injected with 89VP1 (89VP1, 89P5edc and r89P5). Rabbits immunized with 89VP1, r89P5 and KLHP5 show the same result.

Example 6 rPhl p 1-Specific Antibody Response in Immunized Mice Determined by ELISA

To evaluate whether immunization with r89P5 will induce IgG antibodies that react with complete Phl p 1, the same method and the same mice sera were used as described in example 5. ELISA plates were coated with 5 µg/ml rPhl p 1 and the IgG1 antibody titer was determined (FIG. 5).

All Phl p 1 derived peptides either coupled to KLH or 89VP1 induced rPhl p 1 specific IgG1 antibodies with increasing responses during immunizations. Rabbits immunized with r89P5 and KLHP5 show the same result.

Example 7

ELISA Detection of Timothy Grass Pollen Extract-Specific IgG1 Antibodies

Immunization of mice and ELISA analysis was performed as described in section 5. Whole timothy grass pollen extract was coated (100 µg/ml) on ELISA plates and the IgG1 antibody titer was determined (FIG. 6).

After three immunizations extract-specific IgG1 antibodies could be detected in mice immunized with peptide 5.

Example 8

Rabbit Anti-r89P5 Antibodies Block Patient's IgE-Binding to rPhl p 1

To determine the ability of peptide-induced rabbit Ig to inhibit the binding of allergic patients' IgE antibodies to rPhl p 1, ELISA plates were coated with 1 µg/ml rPhl p 1, washed and blocked. The plates were preincubated with 1:100-diluted rabbit anti-peptide (89P5, KLHP5), a rabbit anti rPhl p 1 and, for control purposes, with the corresponding preimmune sera. After washing, plates were incubated with human sera from Phl p 1-allergic patients (1:3 diluted) and bound IgE was detected with mouse anti-human IgE (Pharmingen 1:1000) and then with sheep anti-mouse IgG POX-coupled (Amersham Bioscience) 1:2000. The percentage of inhibition of IgE-binding achieved by preincubation with the anti peptide antisera was calculated as follows: $100 - OD_i/OD_p \times 100$.

$OD_i$ and $OD_p$ represent the extinctions after preincubation with the rabbit immune and preimmune serum, respectively. Table 2 shows the capacity of anti-Phl p 1 peptide antibodies to inhibit the binding of 19 allergic patients' IgE to complete rPhl p 1. FIG. 7 displays the mean inhibition (in %) of all anti-rPhl p 1, anti-r89P5 and anti-KLHP5 immune sera. Anti-peptide sera blocked the IgE-binding much better then rPhl p 1. The ability for inhibition is with 89P5 and KLHP5 almost alike. Table 2 shows the inhibition (in %) of all 19 patients.

TABLE 2

% inhibition of 19 patients' IgE-binding to rPhl p 1 after incubation with rabbit anti-rPhl p 1, r89P5 and anti-KLHP5 antisera

| | % inhibition | | |
|---|---|---|---|
| patient | rPhl p 1 | r89P5 | KLHP5 |
| 1 | 32.343 | 68.291 | 68.213 |
| 2 | 29.373 | 64.915 | 61.509 |
| 3 | 10.367 | 59.469 | 66.270 |
| 4 | 28.087 | 73.906 | 71.330 |
| 5 | 13.808 | 49.358 | 45.372 |
| 6 | 22.597 | 66.259 | 67.331 |
| 7 | 5.375 | 26.667 | 18.902 |
| 8 | 22.478 | 42.612 | 47.979 |
| 9 | 5.019 | 39.822 | 56.837 |
| 10 | 13.756 | 53.878 | 63.047 |
| 11 | 26.444 | 58.430 | 57.944 |
| 12 | 25.795 | 67.243 | 62.458 |
| 13 | 41.330 | 75.694 | 79.517 |
| 14 | 35.543 | 85.714 | 87.012 |
| 15 | 45.796 | 84.255 | 75.185 |
| 16 | 32.641 | 76.508 | 77.412 |
| 17 | 26.483 | 63.171 | 47.735 |
| 18 | 19.229 | 85.750 | 86.642 |
| 19 | 31.142 | 62.428 | 71.086 |

Example 9

T-Cell Proliferation of Mouse Spleen Cells after Antigen Stimulation

Groups of three mice were immunized with KLH, KLHP5 and KLHP5edc. Groups of 4 mice were immunized four times with 89VP1, r89P5 and 89P5edc, and 2 mice were immunized with peptide 5 only (5 µg each). Spleen cells were taken 10 days after the last immunization and single cell cultures were stimulated in triplicates in 96 well plates with peptide 5 (P5), 89VP1, KLH, Con A and a medium as a positive and negative control, respectively. After four days radioactive [$^3$H]thymidine 0.5 µCi was added to each well. Cells were then harvested with a Packard Cell Harvester onto unifilter plates after 15 hours. Cell-associated radioactivity was measured with a beta-counter. Stimulation indices where calculated and are shown at the y-axis. The antigen which was used for stimulation is shown on the x-axis. Each box represents the data of the antigen which was used for immunization of the mice (FIG. 8). All values above two count as positive. The KLH and KLHP5 immunized mice are only positive when stimulated with KLH and the peptide 5 mice are completely negative. The KLHP5edc group is also negative which corresponds to the ELISA results. Cells from r89P5, 89P5edc and 89VP1 immunized mice proliferated only after stimulation with 89VP1. The naive control mouse shows no proliferation in all cases. These results show that T-cell epitopes are provided by the carrier 89VP1 and not by the peptide 5.

Example 10

Detection of 14VP1-, 89VP1- and rPhl p 1-Specific Antibodies in Human Sera Obtained in Autumn and Winter by ELISA Five human sera of randomly chosen persons were taken in autumn and five in winter. The IgG1, IgG2, IgG4 and IgA antibody level against 14VP1, 89VP1 and rPhl p 1 was determined by ELISA as described in example 5. Human IgG1, IgG2, IgG4 and IgA were detected (BD Pharmingen) 1:1000 with sheep anti mouse IgG POX-coupled (Amersham Bioscience) 1:2000. A high anti-14VP1 and 89VP1 IgG1 titer of sera taken in autumn and winter could be detected (FIG. 9). The anti-rPhl p 1 IgG1 antibody titer was much lower. IgG2, IgG4 and IgA antibodies could be detected in all cases at a very low level. The VP1 proteins of the different HRV strains are closely related and cross-reactivity has been shown in other studies.

Example 11

Anti-89VP1 and Anti-rPhl p 1 Antibodies of Phl p 1 Allergic Patients

Sera of five Phl p 1 allergic patients were taken and an ELISA experiment was performed as described in example 5. ELISA plates were coated with rPhl p 1 and 89VP1 and the specific IgM, IgG1, IgG2, IgG3, IgG4, IgA and IgE antibody titer were determined (FIG. 10). More anti-89VP1 IgG1 antibodies than anti-rPhl p 1 IgG1 antibodies could be detected.

Example 12

Detection of Anti-14VP1 Antibody Binding to the Whole Virus by Western Blot Analysis The IgG antibody binding of sera of the 14VP1 injected rabbit to the whole virus was confirmed by using the whole HRV14 virus (lane 2 and 5) and 5 µg purified 14VP1 (lane 3 and 6) as control. The virus extract was separated by 12% SDS-Page and blotted onto nitrocellulose membrane. Rabbit anti-14VP1 antiserum (lane 1-3) 1:500 and preimmune serum (lane 4-6) 1:500 were tested for binding to HRV14 and 14VP1. Bound IgG was detected with 125I-labelled donkey anti-rabbit antibody and visualized by autoradiography (FIG. 11).

The binding of 14VP1-antiserum could be detected at the same seize (33.6 kD) as 14VP1.

Example 13

Anti-14VP1 Antibodies Neutralization of Intact Human Rhinovirus 14

The tissue culture dosis 50 (TCD50) of HRV14 was determined. Therefore, a virus dilution from $1:10^2$-$1:10^8$ in MEM-Eagle 1% FCS and 40 mM $MgCl_2$ was performed and incubated in 24 well plates at 34° C. in a humidified 5% $CO_2$ atmosphere together with HeLa Ohio cells for three days. A control without the virus was also spread out.

The cytotoxic effect of the virus was visualized with crystal violet after three days and the TCD50 (the dilution where 50% of the cells are dead) was calculated.

Serum dilutions and virus (100TCD50) in row A and B were incubated at 34° C. After 2 hours cells were spread out in all wells. D5 and D6 are serum controls. The experimental schema is shown in FIG. 12. The neutralization effect of the antibodies was detected after three days with crystal violet (FIG. 12).

Example 14

Characteristics of Phl p 5-Derived Synthetic Peptides

Peptides were synthesized using Fmoc-strategy with HBTU-activation (0.1 mmol small-scale cycles) on the Applied Biosystems peptide synthesizer Model 433A as described. (Focke et al. Faseb J (2001) 15:2042). After in-depth analysis of the Phl p 5 allergen six Phl p 5-derived peptides ranging from 31 (P1: 3026 Dalton) to 38 (P6: 3853 Dalton) amino acids in length which are rich in solvent-exposed amino acids were prepared (Table 3).

These peptides have isoelectric points between 4.32 and 8.98 and three of them (peptide 3, 4 and 6) may contain human T-cell epitopes.

TABLE 3

Characteristics of non-allergenic Phl p 5-derived synthetic peptides. Position (in relation to the Phl p 5 molecule), sequence, length, molecular weight (MW), isoelectric point (pI) and presence of T-cell epitopes of the Phl p 5-derived peptides are displayed. The cysteine residue added to facilitate the coupling is marked in bold and underlined.

|  | aa position | Sequence | aa length | MW | pI | T-cell epitope |
|---|---|---|---|---|---|---|
| Pept. 1 (SEQ ID No. 9) | 98-128 | CGAASNKAFAEGLSGEP-KGAAESSSKAALTSK | 32 | 3026 | 8.16 | − |
| Pept. 2 (SEQ ID No. 10) | 26-58 | ADLGYGPATPAAPAAGYT-PATPAAPAEAAPAGKC | 34 | 3068 | 4.37 | − |
| Pept. 3 (SEQ ID No. 11) | 132-162 | AYKLAYKTAEGATPEAKY-DAYVATLSEALRIC | 32 | 3482 | 6.29 | + |
| Pept. 4 (SEQ ID No. 12) | 217-246 | CEAAFNDAIKASTG-GAYESYKFIPALEAAVK | 31 | 3236 | 4.87 | + |
| Pept. 5 (SEQ ID No. 13) | 252-283 | TVATA-PEVKYTVFETALKKAITAM-SEAQKAAKC | 33 | 3501 | 8.98 | − |

TABLE 3-continued

Characteristics of non-allergenic Phl p 5-derived synthetic peptides. Position (in relation to the Phl p 5 molecule), sequence, length, molecular weight (MW), isoelectric point (pI) and presence of T-cell epitopes of the Phl p 5-derived peptides are displayed. The cysteine residue added to facilitate the coupling is marked in bold and underlined.

| | aa position | Sequence | aa length | MW | pI | T-cell epitope |
|---|---|---|---|---|---|---|
| Pept. 6 (SEQ ID No. 14) | 176-212 | CAEEVKVIPAGELQVIEK-VDAAFKVAATAANAAPANDK | 38 | 3853 | 4.66 | + |

Example 15

Phl p 5-Derived Peptides Lack IgE Reactivity and Allergenic Activity 15.1. Lack of IgE Reactivity To analyze the IgE reactivity of the six Phl p 5-derived peptides, the isolated as well as KLH-coupled Phl p 5-derived peptides were compared with complete rPhl p 5 regarding IgE-binding capacity by ELISA using sera from 29 grass pollen allergic patients (Table 4).

TABLE 4

Serological characterization of 29 grass pollen allergic patients and a non-allergenic control. Sex, age, total serum IgE levels (kU/L), timothy extract-specific IgE (kUA/L), IgE antibodies specific for rPhl p 5 and the 6 isolated (P1-P6) and KLH-coupled (KLH-P1-KLH-P6) peptides were measured by ELISA and ODs (optical densities) are shown. Dashes indicate the lack of IgE reactivity to the isolated as well as to the KLH-coupled peptides.

| Patient | sex | age | total IgE (kU/L) | timothy kUA/L | rPhl p 5 | P1 | P2 | P3 | P4 | P5 | P6 |
|---|---|---|---|---|---|---|---|---|---|---|---|
| 1 | m | 29 | 140.0 | 25.90 | 1.437 | — | — | — | — | — | — |
| 2 | m | 39 | 76.2 | 10.50 | 0.456 | — | — | — | — | — | — |
| 3 | f | 29 | 100.0 | 33.50 | 0.699 | — | — | — | — | — | — |
| 4 | f | 31 | 261.0 | 28.10 | 0.930 | — | — | — | — | — | — |
| 5 | m | 33 | 380.0 | 32.00 | 0.545 | — | — | — | — | — | — |
| 6 | f | 31 | 278.0 | 37.00 | 1.720 | — | — | — | — | — | — |
| 7 | m | 43 | 128.0 | 20.70 | 1.118 | — | — | — | — | — | — |
| 8 | f | 29 | 200.0 | 18.40 | 0.489 | — | — | — | — | — | — |
| 9 | f | 34 | 76.6 | 18.70 | 0.571 | — | — | — | — | — | — |
| 10 | m | 35 | 144.0 | 39.30 | 0.157 | — | — | — | — | — | — |
| 11 | f | 33 | 79.2 | 29.60 | 0.574 | — | — | — | — | — | — |
| 12 | f | 30 | 30.3 | 10.70 | 0.350 | — | — | — | — | — | — |
| 13 | f | 34 | 106.0 | 20.80 | 0.395 | — | — | — | — | — | — |
| 14 | f | 52 | 448.0 | 43.00 | 1.320 | — | — | — | — | — | — |
| 15 | f | 25 | 294.0 | 95.50 | 1.638 | — | — | — | — | — | — |
| 16 | m | 30 | 471.0 | 82.60 | 0.752 | — | — | — | — | — | — |
| 17 | m | 44 | 2000.0 | 100.00 | 2.500 | — | — | — | — | — | — |
| 18 | f | 30 | 168.0 | 66.60 | 0.806 | — | — | — | — | — | — |
| 19 | m | 42 | 512.0 | 50.30 | 1.175 | — | — | — | — | — | — |
| 20 | f | 28 | 253.0 | 54.00 | 1.954 | — | — | — | — | — | — |
| 21 | m | 30 | 315.0 | 100.00 | 1.054 | — | — | — | — | — | — |
| 22 | f | 42 | 401.0 | 89.50 | 2.297 | — | — | — | — | — | — |
| 23 | f | 28 | 100.0 | 82.10 | 1.802 | — | — | — | — | — | — |
| 24 | m | 42 | 52.5 | 3.52 | 0.885 | — | — | — | — | — | — |
| 25 | m | 34 | 136.0 | 6.11 | 2.036 | — | — | — | — | — | — |
| 26 | m | 30 | 31.2 | 9.17 | 1.909 | — | — | — | — | — | — |
| 27 | m | 36 | 24.9 | 4.34 | 0.233 | — | — | — | — | — | — |
| 28 | f | 41 | 41.5 | 2.19 | 0.281 | — | — | — | — | — | — |
| 29 | f | 51 | 370.0 | 90.10 | 1.296 | — | — | — | — | — | — |
| NHS | m | 39 | 0.0 | 0.00 | 0.065 | — | — | — | — | — | — |

ELISA plates (Nunc Maxisorp, Denmark) were coated with Phl p 5-derived peptides (5 µg/ml) or rPhl p 5 as control (5 µg/ml), washed and blocked. Subsequently, plates were incubated with 1:3 diluted sera from 29 grass pollen allergic patients and from a non-atopic individual overnight at 4° C. Grass pollen allergic patients suffering from allergic rhinoconjunctivitis and/or asthma were selected according to case history indicative for seasonal grass pollinosis and characterized by skin prick testing with timothy pollen extract and serological CAP-FEIA (Pharmacia Diagnostics, Uppsala, Sweden) testing. Total IgE levels in the sera were determined by CAP measurements (Pharmacia). IgE antibodies specific for rPhl p 5 were determined by ELISA. Sera from 29 grass pollen allergic patients and a non-atopic individual were used for IgE competition studies. The grass pollen allergic patients group consisted of 13 males and 16 females with a mean age of 35 years (ranging from 25-51 years) (Table 4).

Bound IgE antibodies were detected with a 1:1000 diluted alkaline-phosphatase-coupled mouse monoclonal anti-human IgE antibody (Pharmingen, Calif.).

Total IgE levels and grass pollen extract-specific IgE ranged from 24.9-2000 kU/L (mean: 262.7) and 2.2-100 kUA/L (mean: 41.5), respectively. All patients contained rPhl p 5-specific IgE antibodies ranging between 0.157-2.530 OD units (mean: 1.082 OD units), but none of the 29 patients showed IgE reactivity to any of the peptides (P1-P6) or to an equimolar mix of the peptides (OD≤0.08). This result demonstrates that no serum contained detectable IgE antibodies with specificity for any of the six Phl p 5 derived peptides.

15.2. Reduced Allergenic Activity of the Peptides as Detected by CD 203 C Expression on Basophils: Basophil Activation and Flow Cytometry:

The upregulation of CD 203 c has been described as a surrogate marker for allergen-induced basophil activation and degranulation (Hauswirth et al., J Allergy Clin Immunol 2002; 110:102). Therefore, the allergenic activity of complete rPhl p 5 allergen and an equimolar mix of peptides by measuring CD 203 c upregulation on basophils of grass pollen allergic patients was compared.

Peripheral blood cells were obtained from 3 allergic donors after informed consent had been given. Heparinized blood aliquots (100 µl) were incubated with serial dilutions of recombinant allergens (10-4 to 10 µg/ml), anti-IgE antibody (1 µg/ml) or control buffer (phosphate-buffered saline=PBS) for 15 minutes at 37° C. After incubation, cells were washed in PBS containing 20 mM EDTA. Cells were then incubated with 10 µl of PE-conjugated CD203c mAb 97A6 for 15 minutes at room temperature (RT). Thereafter, erythrocytes were lysed with 2 mL FACS™ Lysing Solution. Cells were then washed, resuspended in PBS, and analyzed by two-color flow cytometry on a FACScan (Becton Dickinson), using Paint-a-Gate Software. Allergen-induced upregulation of CD203c was calculated from mean fluorescence intensities (MFIs) obtained with stimulated (MFIstim) and unstimulated (MFIcontrol) cells, and expressed as stimulation index (MFIstim: MFIcontrol). An SI of ≥2.0 (≥2-fold upregulation) was considered indicative of a specific response.

As shown in FIG. 14 it was found that complete rPhl p 5 shows a dose-dependent (10-4 to 10 µg/mL) increase in expression of CD203c on peripheral blood basophils in a sensitized individual, whereas an equimolar mix of the peptides shows no effect.

Determination of CD 203c expression on basophils from grass-pollen allergic patients indicates that no allergenic activity can be observed with the Phl p 5 derived peptides.

Example 16

Immunization with Phl p 5 Derived Peptides Induces IgG Antibodies Reactive with rPhl p 5 and Natural Allergens from Different Grass Species 16.1. Recombinant Allergens and Allergen Extracts Purified recombinant Phl p 5 were expressed in *E. coli* as described (Vrtala et al. J of Immunol (1993) 151:4773-4781).

Grass pollen from *Phleum pratense, Lolium perenne, Poa pratensis, Dactylis glomerata, Secale cereale, Triticum aestivum, Avena sativa, Hordeum vulgare, Anthoxanthum odoratum* were obtained from Allergon Pharmacia (Sweden), and an aqueous pollen extract was prepared as described (Vrtala et al., Int Arch Allergy Immunol (1993) 102:160-9.).

16.2. Immunization of Rabbits

HPLC-purified peptides were coupled to KLH (keyhole limpet hemocyanin, MW $4.5 \times 10^3$-$1.3 \times 10^7$, Pierce, USA) according to the manufacturers advice and purified using a Conjugation Kit (Sigma, USA).

Rabbits were immunized with each of the KLH conjugated-peptides (200 µg/injection) and, for control purposes, with complete rPhl p 5 using Freunds complete and incomplete adjuvant (Charles River). Serum samples were obtained in four week intervals.

16.3. Reactivity of Rabbit Antibodies with Complete rPhl p 5 and Natural Allergens from Different Grass Species In order to investigate whether antibodies induced after immunization with KLH-coupled peptides recognize the rPhl p 5, natural Phl p 5 and Phl p 5-related grass pollen allergens from other grass pollen species, ELISA experiments were performed.

For ELISA detection, plates (Nunc Maxisorp, Denmark) were coated with pollen allergen extracts (100 µg/ml: *Phleum pratense, Lolium perenne, Poa pratensis Dactylis glomerata, Secale cereale, Triticum aestivum, Avena sativa, Hordeum vulgare, Anthoxanthum odoratum*) or purified recombinant allergen (5 µg/ml: rPhl p 5). ELISA plates were washed and blocked and subsequently incubated with rabbit anti-peptide antisera and corresponding pre-immunsera diluted 1:2500. Bound rabbit IgG was detected with a HRP-coupled goat anti-rabbit Ig antiserum (Jackson Immunresearch, Pennsylvania). Results represent means of duplicate determination with an error of <5% (FIG. 13, Table 5).

Table 5: Crossreactivity of anti-Phl p 5 peptide antisera with rPhl p 5 and natural group 5 allergens from *Phleum pratense, Lolium perenne, Poa pratensis, Dactylis glomerata, Secale cereale, Triticum aestivum, Avena sativa, Hordeum vulgare, Anthoxanthum odoratum*. IgG reactivities (OD values) of peptide antisera (anti-P1 to anti-P6) to Phl p 5 and pollen extracts from grass pollen are displayed for 6 rabbits which were immunized with KLH-conjugated Phl p 5-derived peptides (P1-P6).

| Crossreactivity of anti-peptide antisera with rPhl p 5 and grass pollen extracts | | | | | | |
|---|---|---|---|---|---|---|
| | anti-P1 | anti-P2 | anti-P3 | anti-P4 | anti-P5 | anti-P6 |
| rPhl p 5a | 1.115 | 2.418 | 1.336 | 1.600 | 1.540 | 2.142 |
| *Phleum pratense* | 0.227 | 1.155 | 0.955 | 0.703 | 1.138 | 1.000 |
| *Lolium perenne* | 0.056 | 1.320 | 0.834 | 0.238 | 0.163 | 2.500 |
| *Poa pratensis* | 0.070 | 1.491 | 1.045 | 1.880 | 2.200 | 2.500 |
| *Dactylis glomerata* | 0.060 | 0.390 | 0.728 | 0.689 | 0.154 | 0.657 |
| *Secale cereale* | 0.090 | 0.292 | 0.777 | 0.676 | 0.162 | 0.843 |
| *Triticum aestivum* | 0.116 | 1.076 | 0.734 | 0.404 | 0.570 | 0.703 |
| *Avena sativa* | 0.150 | 0.790 | 1.029 | 0.551 | 0.224 | 1.494 |
| *Anthoxanthum* | 0.114 | 1.209 | 1.531 | 0.827 | 1.114 | 1.115 |
| *Hordeum vulgare* | 0.080 | 1.972 | 1.150 | 1.184 | 0.602 | 1.513 |

16.4. Immunization with Phl p 5-Derived Peptides Induces Cross-Reactive IgG Antibodies Immunization with each of the peptides induced a robust Phl p 5-specific IgG response which became detectable four weeks after the first immunization and increased after the second immunization (FIG. 13). Immunization with peptide 2 induced the highest Phl p 5 specific IgG response followed by peptides 6, 4, 5 and 1 which induced the lowest response. With the exception of anti-peptide 1 antibodies which lacked reactivity with group 5 allergens in *Lolium perenne, Poa pratensis, Dactylis glomerata, Secale cereale* and *Hordeum vulgare*, the other peptide antisera cross-reacted with each of the grass pollen extracts tested (Table 5).

Example 17

Immunization with Phl p 5-Derived Peptides Induces IgG Antibodies which Inhibit the Binding of Crass Pollen Allergic Patients IgE to Phl p 5

17.1. Inhibition of Allergic Patients' IgE-Binding to rPhl p 5a by Peptide-Specific IgG Information regarding the capacity of the peptides to induce blocking antibodies is important since blocking antibodies were shown to play a major role in immunotherapy.

In order to examine the ability of peptide-induced rabbit Ig to inhibit the binding of allergic patients IgE to complete rPhl p 5 ELISA, competition experiments were performed using sera from 29 grass allergic patients.

ELISA plates were coated with rPhl p 5 (1 µg/ml) and preincubated either with a 1:250 dilution of each of the anti-peptide antisera (anti-P1-anti-P6), a mixture of the anti-peptide antisera, an anti-rPhl p 5 antiserum or for control purposes, with the corresponding preimmune sera or a mixture of the preimmune sera. After washing, the plates were incubated with 1:3 diluted sera from 29 grass pollen allergic patients and bound IgE antibodies were detected with the alkaline phosphatase-coupled mouse monoclonal anti-human IgE antibody (Pharmingen). The percentage inhibition of IgE-binding achieved by preincubation with the anti-peptide antisera was calculated as follows: % inhibition of IgE-binding=100−$OD_I/OD_P \times 100$. $OD_I$ and $OD_P$ represent the extinctions after preincubation with the rabbit's immune and preimmune serum, respectively. Preincubation of Phl p 5 with peptide-induced rabbit IgG inhibited allergic patients IgE reactivity to a varying degree. The average degree of inhibition of IgE binding ranged from 19.3% for anti-peptide 6 IgG to 28.5% with anti-peptide 1 IgG. Rabbit antibodies raised agains complete Phl p 5 induced a mean inhibition of IgE binding of 43.6%.

TABLE 6

Rabbit anti-Phl p 5 peptide antisera inhibit serum IgE-binding of timothy pollen allergic patients to Phl p 5. The percentage inhibition of IgE-binding to Phl p 5 is displayed for each patient after preincubation of Phl p 5 with anti-peptide antisera (anti-P1-anti-P6), with a mix of the six anti-peptide antisera (anti-P1-P6) or with an anti-rPhl p 5 antiserum. The mean percentage inhibition is displayed in the bottom line.

% Inhibition of IgE-binding to Phl p 5 with antisera specific for

| Patient | P1 | P2 | P3 | P4 | P5 | P6 | P1-P6 | Phl p 5 |
|---|---|---|---|---|---|---|---|---|
| 1 | 0 | 5 | 4 | 0 | 0 | 0 | 0 | nd |
| 2 | 1 | 10 | 4 | 0 | 0 | 0 | 0 | nd |
| 3 | 28 | 35 | 28 | 39 | 37 | 38 | 46 | 50 |
| 4 | 33 | 40 | 33 | 42 | 35 | 45 | 54 | 20 |
| 5 | 0 | 0 | 3 | 8 | 8 | 0 | 9 | nd |
| 6 | 46 | 34 | 39 | 47 | 47 | 34 | 21 | 56 |
| 7 | 41 | 48 | 46 | 49 | 50 | 45 | 49 | 60 |
| 8 | 41 | 8 | 34 | 18 | 39 | 0 | 0 | 8 |
| 9 | 6 | 0 | 0 | 0 | 0 | 0 | 0 | nd |
| 10 | 34 | 46 | 30 | 35 | 39 | 42 | 48 | 38 |
| 11 | 28 | 0 | 32 | 0 | 28 | 9 | 0 | nd |
| 12 | 33 | 0 | 27 | 4 | 33 | 0 | 0 | nd |
| 13 | 30 | 31 | 29 | 0 | 29 | 11 | 15 | 0 |
| 14 | 46 | 14 | 49 | 17 | 47 | 2 | 8 | 15 |
| 15 | 48 | 44 | 55 | 22 | 46 | 25 | 23 | 72 |
| 16 | 41 | 0 | 44 | 24 | 41 | 19 | 8 | 28 |
| 17 | 52 | 71 | 50 | 57 | 49 | 59 | 73 | 82 |
| 18 | 43 | 17 | 42 | 0 | 32 | 0 | 10 | 0 |
| 19 | 5 | 17 | 19 | 16 | 7 | 0 | 4 | nd |
| 20 | 42 | 54 | 43 | 38 | 38 | 41 | 48 | 65 |
| 21 | 39 | 51 | 46 | 43 | 43 | 43 | 40 | 39 |
| 22 | 44 | 49 | 44 | 46 | 44 | 40 | 50 | 70 |
| 23 | 38 | 54 | 40 | 42 | 48 | 40 | 50 | 66 |
| 24 | 23 | 0 | 15 | 0 | 0 | 0 | 0 | nd |
| 25 | 0 | 35 | 0 | 8 | 4 | 28 | 43 | nd |
| 26 | 51 | 26 | 31 | 21 | 24 | 0 | 19 | nd |
| 27 | 14 | 15 | 3 | 0 | 9 | 11 | 25 | nd |
| 28 | 9 | 0 | 17 | 0 | 9 | 0 | 0 | nd |
| 29 | 10 | 44 | 11 | 31 | 21 | 28 | 24 | 73 |
| mean | 28.5 | 25.8 | 28.2 | 20.9 | 27.8 | 19.3 | 23.0 | 43.6 | nd: not done.

Example 18

Phl p 5-Derived Peptides Induce Low Specific Lymphoproliferative Responses 18.1. Lymphoproliferation Assays In order to identify peptides with the lowest possible T-cell reactivity to minimize therapy-related side effects, the T-cell reactivity was examined by lymphoproliferation assays. Peripheral blood mononuclear cells (PBMC) were isolated from 2 grass pollen allergic patients by Ficoll (Amersham Pharmacia Biotech, UK) density gradient centrifugation. PBMC ($2 \times 10^5$) were cultured in triplicates in 96-well plates (Nunclone; Nalge Nunc International, Denmark) in 200 µl serum-free Ultra Culture medium (BioWhittaker, Rockland, Me.) supplemented with 2 mM L-glutamine (SIGMA, USA), 50 µM beta-mercaptoethanol (SIGMA) and 0.1 mg gentamicin per ml (SIGMA) at 37° C. and 5% $CO_2$ in a humidified atmosphere. Cells were stimulated with different concentrations of synthetic peptides (1.25, 0.6 and 0.3 µg per well) and, for comparison, with 4 U Interleukin-2 per well (Boehringer Mannheim, Germany) and with medium alone. After 6 d culture 0.5 µCi per well [$^3$H]thymidine (Amersham Pharmacia Biotech) was added and 16 h thereafter incorporated radioactivity was measured by liquid scintillation counting using a microbeta scintillation counter (Wallac ADL, Germany). Mean cpm were calculated from the triplicates, and stimulation indices (SI) were calculated as the quotient of the cpm obtained by antigen or interleukin-2 stimulation and the unstimulated control.

PBMCs from timothy pollen allergic patients were stimulated with different concentrations of synthetic peptides. Stimulation indices with peptides were significantly lower than with IL2. Phl p 5-derived peptides induced low specific lymphoproliferative responses. The lowest response was seen with peptide 5 followed by peptide 4.

Example 19

Characteristics of Fel d 1-Derived Synthetic Peptides

In order to obtain peptides suitable for cat allergy vaccination, five peptides which are 30 to 36 amino acids long and cover the whole molecule were designed according to the known amino acid sequence of Fel d 1.

Peptides were synthesized using a Fmoc (9-fluorenyl-methoxycarbonyl)-strategy with HBTU (2-(1H-benzotriazol-1-yl) 1,1,3,3 tetramethyluronium hexafluorophosphate)-activation (0.1 mmol small-scale cycles) on the Applied Biosystems peptide synthesizer Model 433A (USA). Preloaded PEG-PS (polyethylenglycol polystyrene) resins (0.15-0.2 mmol/g loading) (PerSeptive Biosystems, UK) were used as solid phase to build up the peptides. Chemicals were purchased from Applied Biosystems. Coupling of amino acids was confirmed by conductivity monitoring in a feedback control system. One cystein residue was added to peptides 1, 3, 4, and 5 to facilitate coupling to carriers (Table 7). Peptides were cleaved from the resins with a mixture of 250 µl distilled water, 250 µl triisopropylsilan (Fluka, Switzerland), 9.5 ml TFA for 2 h and precipitated in tert-butylmethylether (Fluka, Switzerland) (Focke 2001). The identity of the peptides was checked by mass-spectrometry and peptides were purified to >90% purity by preparative HPLC (PiChem, Austria).

TABLE 7

Molecular characteristics of Fel d 1-derived synthetic peptides. Position within the native Fel d 1 molecule, amino acid sequence, number of amino acids, calculated molecular weight (MW) and theoretical isoelectric point (pI) of the Fel d 1-derived synthetic peptides are shown. All peptides are soluble in water.

| | Position | Amino acid sequence | aa length | MW | pI |
|---|---|---|---|---|---|
| Pept. 1 SEQ ID No. 15 | chain 1, aa 1-34 | EICPAVKRDVDLFLTGTP-DEYVEQVAQYKALPVVC | 35 | 3911 | 4.30 |

TABLE 7-continued

Molecular characteristics of Fel d 1-derived synthetic peptides. Position within the native Fel d 1 molecule, amino acid sequence, number of amino acids, calculated molecular weight (MW) and theoretical isoelectric point (pI) of the Fel d 1-derived synthetic peptides are shown. All peptides are soluble in water.

|  | Position | Amino acid sequence | aa length | MW | pI |
|---|---|---|---|---|---|
| Pept. 2 SEQ ID No. 16 | chain 1, aa 35-70 | LENARILKNCVDAKMTEEDKEN-ALSLLDKIYTSPLC | 36 | 4083 | 4.72 |
| Pept. 3 SEQ ID No. 17 | chain 2, aa 1-34 | VKMAITCPIFYDVFFAVANG-NELLLDLSLTKVNAC | 35 | 3835 | 4.56 |
| Pept. 4 SEQ ID No. 18 | chain 2, aa 35-63 | TEPERTAMKKIQDCYVENG-LISRVLDGLVC | 30 | 3382 | 4.93 |
| Pept. 5 SEQ ID No. 19 | chain 2, aa 64-92 | CMTTISSSKD-CMGEAVQNTVEDLKLNTLGR | 30 | 3246 | 4.78 |

The five Fel d 1-derived synthetic peptides have molecular weights in the range of 3246 to 4083 Dalton and have calculated isoelectric points of from 4.30 to 4.93. All five peptides are watersoluble and Peptides 1, 2 and 3 may contain human T-cell epitopes (Table 7).

TABLE 8

Reduced IgE reactivity of Fel d 1-derived synthetic peptides compared to rFel d 1

| Patient | sex | age | total IgE (kU/l) | cat dander specific IgE (kUA/l) | rFel d 1 (O.D.) | Peptide 1 (O.D.) | Peptide 2 (O.D.) | Peptide 3 (O.D.) | Peptide 4 (O.D.) | Peptide 5 (O.D.) |
|---|---|---|---|---|---|---|---|---|---|---|
| 1 | f | 36 | >2000 | 48.2 | 2.314 | 0.112 | — | — | — | 0.056 |
| 2 | m | 27 | 798 | 62.2 | 2.255 | 0.069 | 0.123 | — | — | 0.140 |
| 3 | m | 33 | 153 | 9.48 | 1.394 | — | — | — | — | — |
| 4 | m | 25 | 122 | 13.2 | 1.194 | 1.998 | 0.113 | 0.186 | — | 0.073 |
| 5 | f | 42 | 267 | 42.1 | 1.793 | 0.074 | — | — | — | 0.677 |
| 6 | f | 35 | 494 | 37.0 | 2.007 | — | — | — | — | 0.204 |
| 7 | m | 27 | 129 | 31.3 | 2.259 | — | — | — | — | 0.149 |
| 8 | m | 36 | 1150 | 13.5 | 1.384 | — | — | — | — | 0.130 |
| 9 | f | 32 | 580 | 17.3 | 0.569 | — | — | — | — | — |
| 10 | f | 22 | 189 | 4.65 | 0.553 | 0.051 | — | — | — | 0.057 |
| 11 | f | 53 | >2000 | >100 | 2.838 | 0.504 | — | — | — | 0.644 |
| 12 | f | 75 | 4567 | 47.3 | 2.519 | — | 0.060 | — | — | 0.161 |
| 13 | m | 34 | >2000 | 40.0 | 1.244 | — | — | — | — | — |
| 14 | m | n.d. | n.d. | 1.99 | 0.178 | — | — | — | — | — |
| NHS | f | 27 | <2 | <0.35 | — | — | — | — | — | — |

Example 20

Fel d 1-Derived Synthetic Peptides have Reduced IgE Reactivity Compared to rFel d 1 and Fel d 1-Derived Synthetic Peptides Lack Allergenic Activity Serum IgE reactivity to the Fel d 1-derived synthetic peptides in order to identify hypoallergenic peptides suited for vaccination was investigated.

The diagnosis of IgE-mediated cat allergy was based on anamnesis, skin prick testing (Allergopharma, Reinbek, Germany) and measurement of total serum IgE as well as of cat dander-specific serum IgE (CAP-FEIA, Pharmacia Diagnostics, Sweden). Non-allergic persons were included for control purposes.

20.1. IgE-Binding Capacity Measured in ELISA Assays

The IgE-binding capacity of the five Fel d 1-derived synthetic peptides was compared with that of the complete rFel d 1 allergen using sera from 14 cat allergic patients. ELISA plates (Nunc Maxisorb, Denmark) were coated with Fel d 1-derived synthetic peptides or rFel d 1 as control (0.5 µg/well), washed and blocked. Plates were then incubated overnight at 4° C. with 1:5 diluted sera from cat allergic patients and from a non-atopic individual. Bound IgE antibodies were detected with a 1:2500 diluted horse-raddish-peroxidase labeled anti-human IgE antibody (KPL, USA).

Sera from 7 female and 7 male cat allergic patients at the age of 22 to 75 years were subjected to CAP-FEIA determinations. Measured total IgE levels ranged from 122 to >4000 kU/l and cat dander specific IgE levels from 1.99 to >100 kUA/l (Table 7). In ELISA assays the IgE reactivity of all 14 tested sera to the major cat allergen Fel d 1 was confirmed. Results were obtained as optical densities (OD) and ranged from 0.178 to 2.838 OD units. IgE reactivity of the 14 sera to Fel d 1-derived synthetic peptides was measured in the same ELISA assay. It was found that IgE-binding was retained for Peptides 1, 2, 3, and 5. IgE-binding was observed for 6/14 sera to Peptide 1, for 3/14 sera to Peptide 2, for 1/14 sera to Peptide 3 and for 10/14 sera to Peptide 5. Measured OD were between 0.051 and 1.998 for Peptide 1, between 0.060 and 0.123 for Peptide 2, 0.186 for Peptide 3 and between 0.056 and 0.677 for Peptide 5. In summary, all measured OD units were considerably lower than the respective values measured for the whole Fel d 1 allergen.

This demonstrates that Fel d 1-derived synthetic peptides have a reduced IgE reactivity compared to the whole Fel d 1 allergen. Fel d 1-derived synthetic peptides can therefore be considered hypoallergenic, providing the advantage of reduced IgE-mediated side-effects, when used in SIT.

20.2. Specific Induction of Expression of Surface Markers CD203c and CD63 on Human Basophils (FIG. 17)

Since IgE-binding is a prerequisite but not ample for induction of type 1 allergic reactions that also require cross-link of effector cell bound specific IgE, the actual allergenic activity of Fel d 1-derived synthetic peptides was investigated in basophil activation assays. These assays detect an allergen-specific upregulation of surface markers CD203c and CD63, both recognized as markers for basopil activation (Hauswirth et al. J Allergy Clin Immunol. (2002) 110:102-109).

Heparinized blood samples were taken from 5 cat-allergic patients after informed consent had been given. Blood aliquots (100 µl) were incubated with serial dilutions of rFel d 1, Fel d 1-derived synthetic peptides as single components or as equimolar mixture, anti-IgE antibody or buffer (PBS) for 15 minutes at 37° C. After incubation, cells were washed in PBS containing 20 mM EDTA. Cells were then incubated with 10 µl of PE-conjugated CD203c mAb 97A6 and 20 µl of FITC-conjugated CD63 mAb CLB-gran12 for 15 minutes at room temperature. Thereafter, the samples were subjected to erythrocyte lysis with 2 ml FACS™ Lysing Solution. Cells were then washed, resuspended in PBS, and analyzed by two-color flow cytometry on a FACScan (Becton Dickinson, USA), using Paint-a-Gate Software. Allergen-induced upregulation of CD203c and CD63 was calculated from mean fluorescence intensities (MFIs) obtained with stimulated (MFIstim) and unstimulated (MFIcontrol) cells, and expressed as stimulation index (MFIstim:MFIcontrol). An SI of more than 2.0 (i.e. more than 2-fold upregulation) was considered indicative of a specific (diagnostic) response.

On basophils of all five studied cat-allergic patients (RR, EB, KC, MG and SM) stimulation with rFel d 1 induced an allergen-specific upregulation of surface markers CD203c and CD63. The upregulation of CD203c and CD63 was observed to be dose-dependent for 4/5 patients (RR, KC, MG and SM). For these patients CD203c stimulation indices ranged from 1.1 (SM) to 3.2 (RR) for the lowest tested concentration of 0.001 µg rFel d 1/ml and from 3.6 (KC) to 6.2 (RR) for the highest tested concentration of 10 µg rFel d 1/ml. CD63 stimulation indices determined in the same assay ranged from 1.1 (RR) to 2.0 (MG) for the lowest tested rFel d 1 concentration of 0.001 µg/ml and from 3.9 (RR) to 7.3 (MG) for the highest tested rFel d 1 concentration of 10 µg/ml. For Patient EB 0.001 µg/ml Fel d 1 were already sufficient to induce a high-level upregulation of surface markers CD203c and CD63 preventing an observation of dose-dependency of the surface marker upregulation.

Basophils from all five cat-allergic patients were probed with five increasing concentrations (0.005, 0.05, 0.5, 5 and 50 µg/ml) of an equimolar mix of the five Fel d 1-derived synthetic peptides. Basophils from patient RR were additionally probed with five increasing concentrations of the five single Fel d 1-derived synthetic peptides (0.001, 0.01, 0.1, 1 and 10 µg/ml). Peptides were found to be deficient in upregulating the basophil surface markers CD203c and CD63. Peptides were unable to induce any increased expression of CD203c and CD63 on cells of patient RR, KC and SM. A slight upregulation of CD203c (SI=2.3) and of CD63 (SI=2.5) could be detected for patient MG but only for the highest tested concentration of 50 µg peptide mixture/ml, while the lower concentrations applied had also no stimulating effect. A more pronounced upregulation of CD203c (SI=4.2) and CD63 (SI=4.3) was observed for patient EB but, again, only for the highest tested peptide mixture concentration. In both cases, patient MG and EB, the rate of upregulation after stimulation with peptides was considerably lower than the corresponding values for stimulation with the whole Fel d 1 allergen.

This demonstrates that Fel d 1-derived synthetic peptides provide the advantage of holding a lower allergenic activity than the whole Fel d 1 allergen. This is relevant for a decreased risk of IgE-mediated side-effects when Fel d 1-derived synthetic peptides are used in SIT.

Example 21

Immunization with Fel d 1-Derived Synthetic Peptides Induces IgG Antibodies Reactive with the Whole rFel d 1 Allergen Fel d 1-derived synthetic peptides were shown to be deficient in IgE-binding. As candidate molecules for vaccination, which aims at the induction of allergen-specific IgG antibodies, peptides must retain specific allergen structures and must still be able to induce an IgG immune response specific for the whole allergen. In order to find out whether Fel d 1-derived synthetic peptides fulfill these requirements, immunization experiments in rabbits were performed.

Rabbits were immunized with uncoupled rFel d 1 and KLH-coupled Fel d 1-derived synthetic peptides. HPLC-purified peptides were coupled to KLH via their cysteine residues, using an Imject Maleimide Activated Immunogen Conjugation Kit (Pierce, USA).

Rabbits (New Zealand White rabbits) were immunized with the immunogens (200 µg/injection) using CFA (first immunization) and IFA (first booster injection after 4 weeks; a second booster injection with incomplete adjuvant was given after 7 weeks) (Charles River Breeding Laboratories, Germany). Rabbits were bled 8 weeks after the first immunization and in four-week intervals thereafter.

The induction of peptide- and rFel d 1-specific antibodies was monitored in ELISA assays. ELISA plates (Nunc Maxisorb, Denmark) were coated with rFel d 1 (0.5 µg/well), washed and blocked. Plate-bound rFel d 1 was then probed in duplicates with 1:1000 diluted rabbit antisera and the corresponding rabbit preimmune sera, and bound IgG was detected with an 1:2000 diluted hoseraddish-peroxidase labelled goat anti-rabbit antiserum (Jackson ImmunoResearch Inc., USA). Means of duplicates were calculated and showed errors of less than 5%.

Immunization with Fel d 1-derived synthetic peptides induces Fel d 1 reactive IgG antibodies. Eight weeks after the first immunization with each of the five Fel d 1-derived synthetic peptides, IgG antibodies reactive to the whole Fel d 1 allergen could be detected in each of the five rabbit antisera. IgG antibody levels remained at comparable levels in the subsequent bleedings (FIG. 16).

Anti-Peptide 1, anti-Peptide 2, anti-Peptide 4 and anti-Peptide 5 rabbit antisera showed IgG reactivities to Fel d 1 at about the same magnitude than the anti-Fel d 1 rabbit antiserum. Also the anti-Peptide 3 rabbit antiserum showed a distinct but a somewhat lower IgG reactivity to Fel d 1.

This indicates that all 5 Fel d 1-derived synthetic peptides are candidate molecules to induce an Fel d 1 specific IgG antibody response.

Example 22

Fel d 1-Derived Synthetic Peptides Induce Weaker Lymphoproliferative Responses than Fel d 1

Desired candidate molecules for improved SIT do not only offer the advantage of reduced IgE-mediated side effects but also of reduced T-cell mediated side effects. In order to investigate the T-cell activating properties of Fel d 1-derived synthetic peptides, lymphoproliferative assays were performed.

PBMCs were isolated from 7 cat-allergic patients by Ficoll (Amersham Pharmacia Biotech, UK) density gradient centrifugation. PBMC ($2\times10^5$) were cultured in triplicates in 96-well plates (Nunclone, Nalgene Nunc International, Denmark) in 200 µl serum-free Ultra Culture medium (Cambrex, Belgium) supplemented with 2 mM L-glutamine (Sigma, USA), 50 µM β-mercaptoethanol (Sigma) and 0.1 mg gentamicin per ml (Sigma) at 37° C. using 5% $CO_2$ in a humidified atmosphere. Cells were stimulated with different concentrations (5, 2.5, 1.25 and 0.6 µg/well) of rFel d 1 and Fe d 1-derived synthetic peptides as single components or as equimolar mixture and, for control purposes, with 4 U interleukin-2 or with medium alone. After 6 days of culture, 0.5 µCi per well $^3$H-thymidine (Amersham Pharmacia Biotech) was added and 16 h thereafter, incorporated radioactivity was measured by liquid scintillation counting using a microbeta scintillation counter (Wallac ADL, Germany), and mean cpm were calculated from the triplicates. The stimulation index (SI) was calculated as the quotient of the cpm obtained by antigen or interleukin-2 stimulation and the unstimulated medium control.

IL-2 stimulated proliferation of PBMC from all 7 tested cat-allergic patients, resulting in stimulation indices of 9.8 for RR, 5.2 for EB, 3.2 for KC, 6.7 for MG, 6.3 for SM, 15.7 for RA and of 13.9 for AR.

Fel d 1-derived synthetic peptides induced lower stimulation indices (Table 9).

TABLE 9

Fel d 1-derived synthetic peptides which on an equimolar basis induce weaker lymphoproliferative responses than Fel d 1 can be identified. PBMCs from 7 cat-allergic patients were stimulated with serial dilutions of rFel d 1 or Fel d 1-derived synthetic peptides as single components. Specific lymphoproliferative responses are shown as stimulation indices.

| | | 5 µg/w | 2.5 µg/w | 1.25 µg/w | 0.6 µg/w |
|---|---|---|---|---|---|
| Patient RR | rFel d 1 | 2.6 | 1.8 | 1.5 | 1.9 |
| | Peptide 1 | 1.9 | 0.6 | 1.3 | 1.5 |
| | Peptide 2 | 2.1 | 1.3 | 2.0 | 1.6 |
| | Peptide 3 | 3.5 | 2.8 | 2.0 | 3.0 |
| | Peptide 4 | 2.5 | 2.4 | 1.5 | 0.8 |
| | Peptide 5 | 1.7 | 0.9 | 2.3 | 0.7 |
| Patient EB | rFel d 1 | 8.2 | 2.9 | 1.6 | 1.5 |
| | Peptide 1 | 1.3 | 0.9 | 1.0 | 1.2 |
| | Peptide 2 | 2.4 | 1.7 | 1.8 | 1.6 |
| | Peptide 3 | 1.1 | 1.2 | 1.4 | 1.7 |
| | Peptide 4 | 3.6 | 3.6 | 3.2 | 2.3 |
| | Peptide 5 | 2.2 | 2.1 | 1.4 | 2.1 |
| Patient KC | rFel d 1 | 0.8 | 1.2 | 1.3 | 5.2 |
| | Peptide 1 | 0.7 | 1.0 | 1.1 | 1.1 |
| | Peptide 2 | 1.2 | 1.5 | 1.0 | 1.1 |
| | Peptide 3 | 0.6 | 0.5 | 0.5 | 0.6 |
| | Peptide 4 | 1.6 | 1.4 | 1.3 | 1.1 |
| | Peptide 5 | 1.3 | 1.4 | 0.9 | 1.4 |
| Patient MG | rFel d 1 | 2.9 | 2.3 | 2.3 | 2.2 |
| | Peptide 1 | 1.8 | 1.4 | 1.4 | 1.1 |
| | Peptide 2 | 1.2 | 1.3 | 1.4 | 0.9 |
| | Peptide 3 | 1.1 | 0.5 | 0.6 | 0.7 |
| | Peptide 4 | 1.1 | 1.5 | 1.8 | 1.0 |
| | Peptide 5 | 1.5 | 1.2 | 1.6 | 0.8 |
| Patient SM | rFel d 1 | 2.3 | 1.6 | 1.8 | 1.1 |
| | Peptide 1 | 1.1 | 1.0 | 0.8 | 1.0 |
| | Peptide 2 | 1.8 | 1.1 | 1.3 | 1.2 |
| | Peptide 3 | 2.6 | 2.1 | 2.1 | 1.5 |
| | Peptide 4 | 1.9 | 1.6 | 1.7 | 1.1 |
| | Peptide 5 | 2.3 | 1.3 | 1.4 | 1.0 |
| Patient RA | rFel d 1 | 3.2 | 1.2 | 2.4 | 1.2 |
| | Peptide 1 | 0.8 | 0.7 | 1.3 | 1.1 |
| | Peptide 2 | 1.2 | 0.5 | 1.7 | 1.6 |
| | Peptide 3 | 2.0 | 2.3 | 1.6 | 0.9 |
| | Peptide 4 | 3.0 | 1.3 | 1.1 | 0.6 |
| | Peptide 5 | 0.4 | 0.6 | 0.9 | 0.9 |
| Patient AR | rFel d 1 | 1.4 | 0.6 | 0.9 | 1.0 |
| | Peptide 1 | 1.0 | 0.5 | 1.7 | 0.7 |
| | Peptide 2 | 0.7 | 0.6 | 0.9 | 0.6 |
| | Peptide 3 | 1.6 | 1.6 | 2.1 | 1.0 |
| | Peptide 4 | 1.0 | 0.7 | 0.7 | 0.6 |
| | Peptide 5 | 0.8 | 0.5 | 0.3 | 0.5 |

Example 23

IgG Antibodies Induced by Immunization with Fel d 1-Derived Synthetic Peptides Inhibit Binding of Cat-Allergic Patients IgE to the Whole Fel d 1 Allergen The ability of peptide-induced rabbit Ig to inhibit the binding of allergic patients' IgE antibodies to complete rFel d 1 was examined in ELISA competition assays. ELISA plates (Nunc Maxisorb, Denmark) were coated with rFel d 1 (0.05 µg/well), washed and blocked. Plate-bound rFel d 1 was then preincubated with 1:100 diluted rabbit anti-peptide antisera (single anti-peptide antisera as well as a mixture of anti-peptide antisera were used), rabbit anti-rFel d 1 antiserum, and for control purposes also with the respective rabbit preimmune sera. After the plates had been washed, they were incubated with 1:5 diluted human sera from cat-allergic patients. Bound IgE antibodies were detected with a 1:2500 diluted horse-raddish-peroxidase labeled anti-human IgE antibody (KPL, USA). The percentage inhibition of IgE-binding achieved by preincubation with the anti-peptide antisera was calculated as follows: % inhibition of IgE-binding=$100-O.D._I/O.D._P\times100$, with $O.D._I$ being the measured optical density after preincubation with rabbit immune sera and $O.D._P$ with rabbit preimmune sera.

Preincubation of ELISA-plate bound Fel d 1 with the 5 anti-peptide rabbit antisera resulted in inhibition patterns that varied between the 14 different tested sera from cat-allergic patients. Anti-Peptide 1 rabbit antiserum blocked patients' IgE-binding to Fel d 1 for 13/14 tested patients' sera, anti-Peptide 2 rabbit antiserum for 8/14, anti-Peptide 3 rabbit antiserum for 13/14, anti-Peptide 4 rabbit antiserum for 9/14 and anti-Peptide 5 rabbit antiserum for 5/14.

Also the range of inhibition showed variations between the different antisera. Among the single tested anti-peptide rabbit antisera, anti-Peptide 1 rabbit antiserum showed best inhibition rates with inhibitions from 0-55% (average 29%). With anti-Peptide 2 rabbit antiserum inhibition rates of 0-18% (average 5%) could be achieved, with anti-Peptide 3 rabbit antiserum of 0-29% (average 11%), with anti-Peptide 4 rabbit antiserum of 0-24% (average 8%) and with anti-Peptide 5 rabbit antiserum of 0-18% (average 4%).

A mix of all 5 anti-peptide rabbit antisera inhibited patients' IgE-binding to Fel d 1 most efficiently with inhibitions achieved for all patients' sera and inhibition rates of 25-84% (average 59%). These inhibitions were even more pronounced than that achieved by preincubation with the anti-Fel d 1 rabbit antiserum (Table 10).

TABLE 10

Rabbit antisera raised against Fel d 1-derived synthetic peptides inhibit binding of human IgE to Fel d 1. The percentage inhibition of IgE-binding to Fel d 1 achieved by pre-incubation of Fel d 1 with rabbit antisera are shown for 14 patients and as means. Preincubations were performed with 5 rabbit antisera raised against the 5 Fel d 1-derived synthetic peptides (anti-Peptide 1-5), a mix of the 5 anti-peptide antisera (Mix) and an antiserum raised against Fel d 1 (anti-rFel d 1).

| Patient | anti-Peptide 1 | anti-Peptide 2 | anti-Peptide 3 | anti-Peptide 4 | anti-Peptide 5 | Mix of the 5 anti-peptide antisera | anti-rFel d 1 |
|---|---|---|---|---|---|---|---|
| 1 | 48 | 18 | 29 | 20 | 18 | 78 | 64 |
| 2 | 24 | 0 | 8 | 0 | 0 | 67 | 43 |
| 3 | 55 | 11 | 5 | 17 | 8 | 84 | 74 |
| 4 | 38 | 7 | 11 | 24 | 8 | 66 | 49 |
| 5 | 10 | 5 | 5 | 12 | 0 | 54 | 48 |
| 6 | 33 | 0 | 12 | 5 | 0 | 68 | 46 |
| 7 | 6 | 1 | 10 | 5 | 0 | 58 | 45 |
| 8 | 44 | 3 | 17 | 10 | 0 | 60 | 53 |
| 9 | 26 | 17 | 12 | 15 | 16 | 53 | 43 |
| 10 | 0 | 0 | 10 | 0 | 0 | 31 | 26 |
| 11 | 38 | 0 | 0 | 0 | 0 | 52 | 56 |
| 12 | 47 | 0 | 22 | 0 | 7 | 75 | 51 |
| 13 | 27 | 2 | 8 | 0 | 0 | 56 | 41 |
| 14 | 16 | 0 | 6 | 5 | 0 | 25 | 25 |
| mean | 29 | 5 | 11 | 8 | 4 | 59 | 47 |

When the anti-Peptide 1 rabbit antiserum was combined with each of the other anti-peptide antisera, the inhibition of allergic patients IgE binding was substantially increased reaching almost values (e.g. anti-peptide 1+4:41%, anti-peptide 1+5:42%) obtained with anti-rFel d 1 antibodies (67%) (Table 11).

TABLE 11

| Patient | anti-Peptide 1 + anti Peptide 2 | anti-Peptide 1 + anti Peptide 3 | anti-Peptide 1 + anti Peptide 4 | anti-Peptide 1 + anti Peptide 5 | anti-rFel d 1 |
|---|---|---|---|---|---|
| 1 | 61 | 49 | 61 | 63 | 75 |
| 2 | 24 | 17 | 28 | 28 | 74 |
| 3 | 60 | 52 | 62 | 57 | 86 |
| 4 | 43 | 33 | 43 | 40 | 68 |
| 5 | 17 | 9 | 27 | 30 | 67 |
| 6 | 37 | 24 | 42 | 46 | 73 |
| 7 | 26 | 21 | 36 | 34 | 74 |
| 8 | 51 | 46 | 53 | 55 | 72 |
| 9 | 40 | 28 | 46 | 43 | 61 |
| 10 | 16 | 11 | 30 | 34 | 40 |
| 11 | 45 | 35 | 47 | 45 | 78 |
| 12 | 52 | 40 | 56 | 59 | 76 |
| 13 | 29 | 17 | 29 | 32 | 62 |
| 14 | 7 | 10 | 14 | 16 | 28 |
| mean | 36 | 28 | 41 | 42 | 67 |

Example 24

Bet v 1-Derived Peptides Induce Bet v 1-Specific IgG Responses Receiving T-Cell Help from Carrier-Derived T-Cell Epitopes and Reduce Bet v 1-Specific T-Cell Proliferation Bet v 1-derived, surface-exposed B cell peptides have already been shown to induce a protective Bet v 1-specific IgG response in a mouse model of therapeutic and prophylactic vaccination (Focke M et al. Clin Exp Allergy (2004) 34:1525-1533). In Focke M et al. (2004), 6 Bet v 1-derived peptides were coupled to the carrier molecule KLH before immunization of mice. In the present example it is shown that the Bet v 1-specific IgG response induced with these peptides (Table 1) is driven by the help of T-cell epitopes derived from the carrier but not from the Bet v 1 allergen. It was surprisingly found that none of the Bet v 1-derived peptides having the sequences LFPKVAPQAISSVENIEGNGGPGTIKKISF (SEQ ID No. 20), GPGTIKKISFPEGFPFKYVKDRVDEVDHTN (SEQ ID No. 21) and VDHTNFKYNYSVIEGGPIGDTLEKISNEIK (SEQ ID No. 22) induced relevant T-cell responses, and it could be demonstrated that the majority of T-cell responses was directed against the carrier molecule, KLH (FIGS. 18 and 19). This finding is of great importance for the reduction of side effects during therapeutic vaccination and for reducing the risk of a potential sensitization during prophylactic vaccination. It has been demonstrated in the past that allergen-derived peptides lacking any IgE reactivity but containing allergen-derived T-cell epitopes induced side effects due to T-cell activation. Allergen-derived peptides lacking IgE and T-cell reactivity as exemplified for the Bet v 1 peptides, induce neither IgE nor T-cell mediated side-effects during therapeutic vaccination. When used for prophylactic vaccination, the peptides will induce a Bet v 1-specific protective IgG response without priming of Bet v 1-specific T-cells. This should minimize the risk of pre-priming an allergic immune response through the vaccine which might pave the road for a subsequent allergic sensitization.

In this example the allergen- and carrier-specific T-cell responses in a mouse model of therapeutic and prophylactic allergen vaccination were dissected. Bet v 1-derived peptides 2, 3, and 6 (Focke M et al. (2004)) were chosen and tested on whether they contain any of the known Bet v 1-specific T-cell epitopes in BALB/c mice. The mice were immunized as follows (Table 10 shows the sensitization and treatment protocol): Groups of BALB/c mice (n=5) were immunized with 10 µg recombinant Bet v 1 (Biomay, Austria) and/or a mixture of the synthetic Bet v 1-derived peptides 2, 3, and 6 (10 µg of each). Peptides were coupled to KLH as previously described (Focke M et al. (2004)). For immunization, Bet v 1 and the peptide mix were adsorbed to aluminium hydroxide (Alu-Gel-S, Serva, Germany) in a total volume of 150 µl/mouse.

TABLE 12

Sensitization and treatment protocol.

| groups (n = 5) | Sensitization (rBet v 1) | Therapy (peptides KLH) |
|---|---|---|
| no Sensitization/no Therapy (S−/T−) | — | — |
| Sensitization/no Therapy (S+/T−) | day 0, 20, 40 | — |
| no Sensitization/Therapy (S−/T+) | — | day 60, 80, 100 |
| Sensitization/Therapy (S+/T+) | day 0, 20, 40 | day 60, 80, 100 |
| | Prophylaxis (peptides KLH) | Sensitization (rBet v 1) |
| no Prophylaxis/Sensitization (P−/S+) | — | day 60, 80, 100 |
| Prophylaxis/no Sensitization (P+/S−) | day 0, 20, 40 | — |
| Prophylaxis/Sensitization (P+/S+) | day 0, 20, 40 | day 60, 80, 100 |

Allergen-, peptide-, and carrier-specific lymphoproliferation was analyzed in a T-cell proliferation assay. Spleens were removed under sterile conditions and homogenized. After lysis of erythrocytes, cells were washed and resuspended in complete medium (RPMI, 10% fetal calf serum, 0.1 mg/ml gentamycin, 2 mM glutamine). Single cell suspensions were plated into 96-well round-bottom plates at a concentration of $2 \times 10^5$ cells/well and stimulated with concavalin A (0.5 µg/well) as a positive control, rBet v 1 (2 µg/well), KLH (2 µg/well), the peptide mix (0.34 µg of each peptide/well) or the medium alone for 4 days. The cultures were pulsed with 0.5 µCi/well tritiated thymidine for 16 h and harvested. The proliferation responses were measured by scintillation counting. The ratio of the mean proliferation after antigen stimulation and medium control values, i.e. the stimulation index (SI), was calculated.

Interestingly, it could be shown that therapeutic vaccination with Bet v 1-derived peptides could reduce Bet v 1-specific proliferation in Bet v 1 sensitized mice (group S+/T+) compared to the sensitized but untreated group S+/T−. In the sensitized and treated group no peptide-specific proliferation could be measured, but according to the carrier effect, a KLH-specific proliferation was observed. The peptide vaccine alone (group S−/T+) induced mainly KLH-specific T-cells, but almost no Bet v 1-specific T-cell response (FIG. 18).

Prophylactic vaccination with the peptides induced almost no Bet v 1-specific proliferation (group P+/S−) compared to the Bet v 1-sensitized group P−/S+ but KLH-specific proliferation. In prophylactically vaccinated and subsequently sensitized mice (group P+/S+) Bet v 1 specific proliferation was remarkably reduced, furthermore, no peptide-specific response could be observed in any mouse group (FIG. 19).

Thus, it could be shown in an allergy mouse model that prophylactic vaccination with carrier-bound allergen-derived B cell peptides did not prime peptide-specific T-cells, almost no allergen-specific but carrier-specific T-cells. Prophylactic vaccination preceding allergic sensitization but also therapeutic vaccination of sensitized mice reduces allergen-specific T-cell proliferation.

Prophylactic treatment with Bet v 1-derived peptides induced Bet v 1-specific IgG responses without help by Bet v 1-specific T-cells. Furthermore, prophylactic treatment increased Bet v 1-specific IgG responses induced by the Bet v 1 allergen already 20 and 40 days after first sensitization (FIG. 20).

These results demonstrate that the peptide vaccine induces a Bet v 1-specific IgG response which can be boosted by allergen exposure.

Example 25

Der p 2-Derived Peptides Showing Reduced IgE Binding Capacity

The IgE binding capacity of Der p 2-derived peptides was determined as described in examples 15.1 and 20.1 employing the peptides according to table 13 and using sera of individuals suffering from house dust mite allergy.

TABLE 13

Der p 2-derived peptides

| Peptide | Position | Sequence | SEQ ID No. |
|---|---|---|---|
| Der p 2 Pep 1 | 1-33 | DQVDVKDCANHEIKKVLVPG CHGSEPCIIHRGK | 96 |
| Der p 2 Pep 2 | 21-51 | CHGSEPCIIHRGKPFQLEAV FEANQNSKTAK | 97 |
| Der p 2 Pep 3 | 42-73 | EANQNSKTAKIEIKASIEGL EVDVPGIDPNAC | 98 |
| Der p 2 Pep 4 | 62-103 | EVDVPGIDPNACHYMKCPLV KGQQYDIKYTWIVPKIAPKSEN | 99 |
| Der p 2 Pep 5 | 98-129 | APKSENVVVTVKVMGDNGVL ACAIATHAKIRD | 100 |

The results clearly show that the Der p 2 derived peptides of the present invention exhibit significantly reduced IgE binding capacity.

TABLE 14

Results

| | rDer p 2 | peptide 1 | peptide 2 | peptide 3 | peptide 4 | peptide 5 |
|---|---|---|---|---|---|---|
| means (n = 50) | 1.080 | 0.010 | 0.015 | 0.004 | 0.031 | 0.006 |

Example 26

Variations in the Length of Peptides have No Effect on Peptides' IgE-Binding Capacity, T-Cell Reactivity and Immunogenicity 26.1. Design of Peptides To study the effect of variation in peptides length on IgE-binding capacity, T-cell reactivity and immunogenicity variants of Phl p 5 derived peptides were designed by increasing the length of peptide 1 (P1) and decreasing the length of peptide 2 (P2) by a few amino-acids (Table 15).

Table 15: Position, sequence, length in number of aminoacids and molecular weight of synthetic Phl p 5 derived peptides (1, 2) and variants thereof (1a, 2b)

TABLE 15

Variants of PHL p 5-derived synthetic peptides

|  | Position aa | Sequence | Number of aa | Molecular Weight (MW) |
|---|---|---|---|---|
| Peptide 1 | 98-128 | CGAASNKAFAEGLSG EPKGAAESSSKAAL TSK | 32 | 3026 |
| 1a | 93-128 | CFVATFGAASNKAFAE GLSGEPKGAAESSSKA ALTSK | 37 | 3592 |
| Peptide 2 | 26-58 | ADLGYGPATPAAPAAG YTPATPAAPAEAAPAG KC | 34 | 3068 |
| 2b | 26-53 | ADLGYGPATPAAPAAG YTPATPAAPAEAC | 29 | 2644 |

26.2. Lack of IgE-Reactivity

To analyse the IgE-reactivity of Phl p 5 derived peptides 1, 2 and their variants 1a, 2b dot-blot assays were performed applying 0.2 μg peptide/dot and using sera from 7 grass-pollen allergic patients (p1-p7) and the serum from a non-atopic individual (NHS). Bound IgE was detected with 125 I-labelled anti-human IgE (Phadia, Uppsala, Sweden). rPhl p 5 was used as positive control and HSA as negative control. Patients react with rPhl p 5 but not with the peptides and peptide variants (FIG. 21).

26.3. Lymphoproliferative Responses

PBMCs from 2 grass pollen allergic patients were stimulated with different concentrations of Phl p 5 derived peptides 1, 2, their variants 1a, 2b and for control purposes with rPhl p 5. Stimulation indices obtained with the peptides were significantly lower than those obtained with rPhl p 5 (FIG. 22).

26.4. Immunogenicity of Peptide Variants

Rabbits were immunized with KLH-coupled Phl p 5 derived peptides and variants. ELISA experiments were used to measure IgG reactivity of the obtained rabbit antisera to peptides and their variants (Table 16). Immunization with peptides and their variants induced cross-reactive IgG antibodies recognizing the peptide and the corresponding variant.

Table 16: Cross-reactivity of anti-Phl p 5 peptide antisera raised in rabbits by immunization with KLH-conjugated peptides. IgG reactivities of peptide antisera to peptides (1, 2) and variants (1a, 2b) are displayed. No reactivity was observed with preimmune-sera (pre P1, pre P1a, pre P2, pre P2b)

a. Anti peptide 1 antiserum (anti P1) cross-reacts with peptide 1 variant (1a) and anti peptide 1a antiserum (anti P1a) cross-reacts with peptide 1.
b. Anti peptide 2 antiserum (anti P2) cross-reacts with peptide 2 variant (2b) and anti peptide 2b antiserum (anti P2b) cross-reacts with peptide 2.

TABLE 16

| Cross-reactivity of rabbit-antisera | | | | |
|---|---|---|---|---|
| a) | | | | |
|  | pre P1 | anti P1 | pre P1a | anti P1a |
| P1 | 0.041 | 0.880 | 0.052 | 0.947 |
| P1a | 0.038 | 0.705 | 0.048 | 0.859 |

TABLE 16-continued

| Cross-reactivity of rabbit-antisera | | | | |
|---|---|---|---|---|
| b) | | | | |
|  | pre P2 | anti P2 | pre P2b | anti P2b |
| P2 | 0.089 | 1.168 | 0.042 | 1.175 |
| P2b | 0.075 | 0.954 | 0.053 | 1.122 |

26.5. Peptide Induced Rabbit Antisera Inhibit Grass Pollen Allergic Patients' IgE Binding to rPhl p 5

The ability of rabbit anti-peptide 2 and 2b IgGs to inhibit human IgE binding to rPhl p 5 was studied in competition ELISAs. ELISA plate bound rPhl p 5 was preincubated with anti P2, anti P2b and, for control purposes, with anti Phl p 5 antisera. Plates were then exposed to sera from 12 grass pollen allergic patients. The percentage of inhibition of IgE-binding to rPhl p 5 is displayed in Table 17. Anti peptide 2 and anti peptide 2b antisera inhibit patients' IgE binding to rPhl p 5 to the same extent.

Competition ELISAs were also performed with rabbit anti peptide 1 and 1a antisera. In example 17 (Immunization with Phl p 5 derived peptides induces IgG antibodies which inhibit the binding of grass pollen allergic patients IgE to Phl p 5) the anti peptide 1 (P1) antibodies inhibited patients IgE binding to Phl p 5 with a mean inhibition rate of 28.5%. Similar results were obtained with anti peptide 1a antiserum which gave an inhibition rate of 23.7%.

Table 17: Inhibition of patients' IgE binding to rPhl p 5 by anti peptide antisera. Anti peptide 2 and anti peptide 2b antisera inhibit patients' IgE binding to rPhl p 5 to the same extent. ELISA plate bound rPhl p 5 was preincubated with anti P2, anti P2b and, for control purposes, with anti Phl p 5 antisera. Plates were then exposed to sera from 12 grass pollen allergic patients. The percentage of inhibition of IgE-binding to rPhl p 5 is displayed.

TABLE 17

| | % Inhibition of IgE-binding | | |
|---|---|---|---|
| patient | anti P2 | anti P2b | anti Phl p 5 |
| 1 | 33.38 | 24.40 | 84.77 |
| 2 | 52.20 | 57.40 | 87.00 |
| 3 | 52.70 | 54.85 | 90.81 |
| 4 | 51.44 | 59.76 | 78.26 |
| 5 | 43.19 | 49.15 | 77.93 |
| 6 | 47.04 | 52.02 | 83.68 |
| 7 | 62.67 | 58.00 | 76.62 |
| 8 | 52.36 | 50.27 | 74.44 |
| 9 | 57.63 | 50.91 | 88.13 |
| 10 | 35.10 | 37.99 | 75.03 |
| 11 | 44.44 | 41.24 | 68.39 |
| 12 | 47.56 | 45.41 | 77.34 |

Example 27

Cross-Protection of Anti-VP1 Antibodies

Human rhinoviruses comprise over hundred different strains. In this neutralization test it is shown that the rhinovirus infection of one strain can also be inhibited by VP1 specific antibodies of another strain. HeLa cells were seeded out in the wells at equal density. $100TCD_{50}$ HRV14 was preincubated with dilutions of anti-14VP1- and anti-89VP1 antibodies (undiluted; 1:2-1:32 wells 1-6) and added to the wells in lane A and D, respectively. In lanes B and C 100TCD$_{50}$ HRV 89 preincubated with dilutions of anti-14VP1- and anti-89VP1 antibodies, respectively, were added to the cells. After 3 days live cells were stained violet. Anti-89VP1 antibodies and anti-14VP1 antibodies block the infection of HRV14 in a comparable manner. The antibodies raised against 14VP1 and 89VP1 also inhibit the infection of HRV89 up to the same concentration.

The invention claimed is:

1. A recombinant hypoallergenic protein comprising a peptide fused or conjugated to a viral protein or a viral protein fragment, wherein the peptide is selected from the group consisting of amino acids 1 to 33 of SEQ ID NO:10; amino acids 2 to 31 of SEQ ID NO:12, and amino acids 2 to 38 of SEQ ID NO:14.

2. The recombinant hypoallergenic protein according to claim 1, wherein the peptide is fused to the N-terminus, the C-terminus or both of the viral protein or the viral protein fragment.

3. The hypoallergenic protein according to claim 1, wherein the viral protein is a capsid protein.

4. The hypoallergenic protein according to claim 1, wherein the viral protein is a human pathogenic virus protein.

5. The hypoallergenic protein according to claim 4, wherein the human pathogenic virus is a human rhinovirus 89 or human rhinovirus 14.

6. A nucleic acid molecule encoding the recombinant hypoallergenic protein according to claim 1.

7. A vector comprising the nucleic acid molecule according to claim 6.

8. The vector according to claim 7, wherein said vector is an expression vector.

9. The vector according to claim 7, wherein said vector is a bacterial vector.

10. An isolated cell, comprising the nucleic acid molecule according to claim 7.

11. A composition, comprising
the recombinant hypoallergenic protein according to claim 1;
and an adjuvant, a pharmaceutically acceptable carrier, a preservative or a combination thereof.

12. The composition according to claim 11, which comprises 10 ng to 1 g of said recombinant hypoallergenic protein.

13. The hypoallergenic protein according to claim 4, wherein the human pathogenic virus is a picornavirus.

14. The composition according to claim 12, wherein the viral protein is a capsid protein.

15. The composition according to claim 12, wherein the virus protein is a human rhinovirus 89 protein or a human rhinovirus 14 protein.

16. The composition according to claim 11, wherein the virus protein is a human pathogenic virus protein.

17. The recombinant hypoallergenic protein according to claim 1, wherein the peptide is amino acids 1 to 33 of SEQ ID NO:10.

18. The recombinant hypoallergenic protein according to claim 1, wherein the peptide is amino acids 2 to 31 of SEQ ID NO:12.

19. The recombinant hypoallergenic protein according to claim 1, wherein the peptide is amino acids 2 to 38 of SEQ ID NO:14.

20. A method for treating a grass pollen allergy in a subject in in need thereof, the method comprising administering the recombinant hypoallergenic protein according to claim 1.

21. A method for treating a grass pollen allergy in a subject in in need thereof, the method comprising administering the composition according to claim 11.

* * * * *

SEQUENCE LISTING

```
<160> NUMBER OF SEQ ID NOS: 142

<210> SEQ ID NO 1
<211> LENGTH: 50
<212> TYPE: DNA
<213> ORGANISM: Artificial
<220> FEATURE:
<223> OTHER INFORMATION: Primer

<400> SEQUENCE: 1
cggaattcat taatatgaac ccagttgaaa attatataga tagtgtatta            50

<210> SEQ ID NO 2
<211> LENGTH: 46
<212> TYPE: DNA
<213> ORGANISM: Artificial
<220> FEATURE:
<223> OTHER INFORMATION: Primer

<400> SEQUENCE: 2
cgattaattc agtggtggtg gtggtggtgg acgtttgtaa cggtaa                46

<210> SEQ ID NO 3
<211> LENGTH: 37
<212> TYPE: DNA
<213> ORGANISM: Artificial
<220> FEATURE:
<223> OTHER INFORMATION: Primer

<400> SEQUENCE: 3
ctttaagaag gagatatact taagatgaac ccagttg                          37

<210> SEQ ID NO 4
<211> LENGTH: 37
<212> TYPE: DNA
<213> ORGANISM: Artificial
<220> FEATURE:
<223> OTHER INFORMATION: Primer

<400> SEQUENCE: 4
caactgggtt catcttaagt atatctcctt cttaaag                          37

<210> SEQ ID NO 5
<211> LENGTH: 33
<212> TYPE: DNA
<213> ORGANISM: Artificial
<220> FEATURE:
<223> OTHER INFORMATION: Primer

<400> SEQUENCE: 5
cctgatgttt ttaccggtac aaacgtccac cac                              33

<210> SEQ ID NO 6
<211> LENGTH: 33
<212> TYPE: DNA
<213> ORGANISM: Artificial
<220> FEATURE:
<223> OTHER INFORMATION: Primer

<400> SEQUENCE: 6
gtggtggacg tttgtaccgg taaaaacatc agg                              33
```

<210> SEQ ID NO 7
<211> LENGTH: 34
<212> TYPE: DNA
<213> ORGANISM: Artificial
<220> FEATURE:
<223> OTHER INFORMATION: Primer

<400> SEQUENCE: 7
cgcgcttaag atggtccgct acaccaccga gggc 34

<210> SEQ ID NO 8
<211> LENGTH: 34
<212> TYPE: DNA
<213> ORGANISM: Artificial
<220> FEATURE:
<223> OTHER INFORMATION: Primer

<400> SEQUENCE: 8
cgcgcttaag cttggactcg taggcggtgt cggc 34

<210> SEQ ID NO 9
<211> LENGTH: 32
<212> TYPE: PRT
<213> ORGANISM: Artificial
<220> FEATURE:
<223> OTHER INFORMATION: Phl p 5 derived hyperallergenic molecule

<400> SEQUENCE: 9

```
Cys Gly Ala Ala Ser Asn Lys Ala Phe Ala Glu Gly Leu Ser Gly Glu
1               5                   10                  15

Pro Lys Gly Ala Ala Glu Ser Ser Ser Lys Ala Ala Leu Thr Ser Lys
            20                  25                  30
```

<210> SEQ ID NO 10
<211> LENGTH: 34
<212> TYPE: PRT
<213> ORGANISM: Artificial
<220> FEATURE:
<223> OTHER INFORMATION: Phl p 5 derived hyperallergenic molecule

<400> SEQUENCE: 10

```
Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Glu Ala Ala Pro Ala Gly
            20                  25                  30

Lys Cys
```

<210> SEQ ID NO 11
<211> LENGTH: 32
<212> TYPE: PRT
<213> ORGANISM: Artificial
<220> FEATURE:
<223> OTHER INFORMATION: Phl p 5 derived hyperallergenic molecule

<400> SEQUENCE: 11

```
Ala Tyr Lys Leu Ala Tyr Lys Thr Ala Glu Gly Ala Thr Pro Glu Ala
1               5                   10                  15

Lys Tyr Asp Ala Tyr Val Ala Thr Leu Ser Glu Ala Leu Arg Ile Cys
            20                  25                  30
```

<210> SEQ ID NO 12
<211> LENGTH: 31
<212> TYPE: PRT

<213> ORGANISM: Artificial
<220> FEATURE:
<223> OTHER INFORMATION: Phl p 5 derived hyperallergenic molecule

<400> SEQUENCE: 12

```
Cys Glu Ala Ala Phe Asn Asp Ala Ile Lys Ala Ser Thr Gly Gly Ala
1               5                   10                  15

Tyr Glu Ser Tyr Lys Phe Ile Pro Ala Leu Glu Ala Ala Val Lys
            20                  25                  30
```

<210> SEQ ID NO 13
<211> LENGTH: 33
<212> TYPE: PRT
<213> ORGANISM: Artificial
<220> FEATURE:
<223> OTHER INFORMATION: Phl p 5 derived hyperallergenic molecule

<400> SEQUENCE: 13

```
Thr Val Ala Thr Ala Pro Glu Val Lys Tyr Thr Val Phe Glu Thr Ala
1               5                   10                  15

Leu Lys Lys Ala Ile Thr Ala Met Ser Glu Ala Gln Lys Ala Ala Lys
            20                  25                  30

Cys
```

<210> SEQ ID NO 14
<211> LENGTH: 38
<212> TYPE: PRT
<213> ORGANISM: Artificial
<220> FEATURE:
<223> OTHER INFORMATION: Phl p 5 derived hyperallergenic molecule

<400> SEQUENCE: 14

```
Cys Ala Glu Glu Val Lys Val Ile Pro Ala Gly Glu Leu Gln Val Ile
1               5                   10                  15

Glu Lys Val Asp Ala Ala Phe Lys Val Ala Ala Thr Ala Ala Asn Ala
            20                  25                  30

Ala Pro Ala Asn Asp Lys
        35
```

<210> SEQ ID NO 15
<211> LENGTH: 35
<212> TYPE: PRT
<213> ORGANISM: Artificial
<220> FEATURE:
<223> OTHER INFORMATION: Fel d 1 derived hyperallergenic molecule

<400> SEQUENCE: 15

```
Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Cys
        35
```

<210> SEQ ID NO 16
<211> LENGTH: 36
<212> TYPE: PRT
<213> ORGANISM: Artificial
<220> FEATURE:
<223> OTHER INFORMATION: Fel d 1 derived hyperallergenic molecule

<400> SEQUENCE: 16

```
Leu Glu Asn Ala Arg Ile Leu Lys Asn Cys Val Asp Ala Lys Met Thr
```

```
1               5                   10                  15
Glu Glu Asp Lys Glu Asn Ala Leu Ser Leu Leu Asp Lys Ile Tyr Thr
                20                  25                  30
Ser Pro Leu Cys
            35

<210> SEQ ID NO 17
<211> LENGTH: 35
<212> TYPE: PRT
<213> ORGANISM: Artificial
<220> FEATURE:
<223> OTHER INFORMATION: Fel d 1 derived hyperallergenic molecule

<400> SEQUENCE: 17

Val Lys Met Ala Ile Thr Cys Pro Ile Phe Tyr Asp Val Phe Phe Ala
1               5                   10                  15

Val Ala Asn Gly Asn Glu Leu Leu Leu Asp Leu Ser Leu Thr Lys Val
                20                  25                  30

Asn Ala Cys
            35

<210> SEQ ID NO 18
<211> LENGTH: 30
<212> TYPE: PRT
<213> ORGANISM: Artificial
<220> FEATURE:
<223> OTHER INFORMATION: Fel d 1 derived hyperallergenic molecule

<400> SEQUENCE: 18

Thr Glu Pro Glu Arg Thr Ala Met Lys Lys Ile Gln Asp Cys Tyr Val
1               5                   10                  15

Glu Asn Gly Leu Ile Ser Arg Val Leu Asp Gly Leu Val Cys
                20                  25                  30

<210> SEQ ID NO 19
<211> LENGTH: 30
<212> TYPE: PRT
<213> ORGANISM: Artificial
<220> FEATURE:
<223> OTHER INFORMATION: Fel d 1 derived hyperallergenic molecule

<400> SEQUENCE: 19

Cys Met Thr Thr Ile Ser Ser Ser Lys Asp Cys Met Gly Glu Ala Val
1               5                   10                  15

Gln Asn Thr Val Glu Asp Leu Lys Leu Asn Thr Leu Gly Arg
                20                  25                  30

<210> SEQ ID NO 20
<211> LENGTH: 30
<212> TYPE: PRT
<213> ORGANISM: Artificial
<220> FEATURE:
<223> OTHER INFORMATION: Bet v 1 derived hyperallergenic molecule

<400> SEQUENCE: 20

Leu Phe Pro Lys Val Ala Pro Gln Ala Ile Ser Ser Val Glu Asn Ile
1               5                   10                  15

Glu Gly Asn Gly Gly Pro Gly Thr Ile Lys Lys Ile Ser Phe
                20                  25                  30

<210> SEQ ID NO 21
<211> LENGTH: 30
<212> TYPE: PRT
```

<213> ORGANISM: Artificial
<220> FEATURE:
<223> OTHER INFORMATION: Bet v 1 derived hyperallergenic molecule

<400> SEQUENCE: 21

Gly Pro Gly Thr Ile Lys Lys Ile Ser Phe Pro Glu Gly Phe Pro Phe
1               5                   10                  15

Lys Tyr Val Lys Asp Arg Val Asp Glu Val Asp His Thr Asn
            20                  25                  30

<210> SEQ ID NO 22
<211> LENGTH: 30
<212> TYPE: PRT
<213> ORGANISM: Artificial
<220> FEATURE:
<223> OTHER INFORMATION: Bet v 1 derived hyperallergenic molecule

<400> SEQUENCE: 22

Val Asp His Thr Asn Phe Lys Tyr Asn Tyr Ser Val Ile Glu Gly Gly
1               5                   10                  15

Pro Ile Gly Asp Thr Leu Glu Lys Ile Ser Asn Glu Ile Lys
            20                  25                  30

<210> SEQ ID NO 23
<211> LENGTH: 40
<212> TYPE: PRT
<213> ORGANISM: Artificial
<220> FEATURE:
<223> OTHER INFORMATION: Alt a 1 derived hyperallergenic molecule

<400> SEQUENCE: 23

Ala Pro Leu Glu Ser Arg Gln Asp Thr Ala Ser Cys Pro Val Thr Thr
1               5                   10                  15

Glu Gly Asp Tyr Val Trp Lys Ile Ser Glu Phe Tyr Gly Arg Lys Pro
            20                  25                  30

Glu Gly Thr Tyr Tyr Asn Ser Leu
        35                  40

<210> SEQ ID NO 24
<211> LENGTH: 37
<212> TYPE: PRT
<213> ORGANISM: Artificial
<220> FEATURE:
<223> OTHER INFORMATION: Alt a 1 derived hyperallergenic molecule

<400> SEQUENCE: 24

Gly Phe Asn Ile Lys Ala Thr Asn Gly Gly Thr Leu Asp Phe Thr Cys
1               5                   10                  15

Ser Ala Gln Ala Asp Lys Leu Glu Asp His Lys Trp Tyr Ser Cys Gly
            20                  25                  30

Glu Asn Ser Phe Met
        35

<210> SEQ ID NO 25
<211> LENGTH: 30
<212> TYPE: PRT
<213> ORGANISM: Artificial
<220> FEATURE:
<223> OTHER INFORMATION: Alt a 1 derived hyperallergenic molecule

<400> SEQUENCE: 25

Glu Asn Ser Phe Met Asp Phe Ser Phe Asp Ser Asp Arg Ser Gly Leu
1               5                   10                  15

```
Leu Leu Lys Gln Lys Val Ser Asp Asp Ile Thr Tyr Val Ala
            20                  25                  30
```

<210> SEQ ID NO 26
<211> LENGTH: 37
<212> TYPE: PRT
<213> ORGANISM: Artificial
<220> FEATURE:
<223> OTHER INFORMATION: Alt a 1 derived hyperallergenic molecule

<400> SEQUENCE: 26

```
Thr Ala Thr Leu Pro Asn Tyr Cys Arg Ala Gly Gly Asn Gly Pro Lys
1               5                   10                  15

Asp Phe Val Cys Gln Gly Val Ala Asp Ala Tyr Ile Thr Leu Val Thr
            20                  25                  30

Leu Pro Lys Ser Ser
            35
```

<210> SEQ ID NO 27
<211> LENGTH: 40
<212> TYPE: PRT
<213> ORGANISM: Artificial
<220> FEATURE:
<223> OTHER INFORMATION: Alt a 2 derived hyperallergenic molecule

<400> SEQUENCE: 27

```
Met His Ser Ser Asn Asn Phe Phe Lys Asp Asn Ile Phe Arg Ser Leu
1               5                   10                  15

Ser Lys Glu Asp Pro Asp Tyr Ser Arg Asn Ile Glu Gly Gln Val Ile
            20                  25                  30

Arg Leu His Trp Asp Trp Ala Gln
            35                  40
```

<210> SEQ ID NO 28
<211> LENGTH: 40
<212> TYPE: PRT
<213> ORGANISM: Artificial
<220> FEATURE:
<223> OTHER INFORMATION: Alt a 2 derived hyperallergenic molecule

<400> SEQUENCE: 28

```
Leu Leu Met Leu Ser Ala Lys Arg Met Lys Val Ala Phe Lys Leu Asp
1               5                   10                  15

Ile Glu Lys Asp Gln Arg Val Trp Asp Arg Cys Thr Ala Asp Asp Leu
            20                  25                  30

Lys Gly Arg Asn Gly Phe Lys Arg
            35                  40
```

<210> SEQ ID NO 29
<211> LENGTH: 40
<212> TYPE: PRT
<213> ORGANISM: Artificial
<220> FEATURE:
<223> OTHER INFORMATION: Alt a 2 derived hyperallergenic molecule

<400> SEQUENCE: 29

```
Cys Leu Gln Phe Thr Leu Tyr Arg Pro Arg Asp Leu Leu Ser Leu Leu
1               5                   10                  15

Asn Glu Ala Phe Phe Ser Ala Phe Arg Glu Asn Arg Glu Thr Ile Ile
            20                  25                  30

Asn Thr Asp Leu Glu Tyr Ala Ala
            35                  40
```

<210> SEQ ID NO 30
<211> LENGTH: 40
<212> TYPE: PRT
<213> ORGANISM: Artificial
<220> FEATURE:
<223> OTHER INFORMATION: Alt a 2 derived hyperallergenic molecule

<400> SEQUENCE: 30

```
Lys Ser Ile Ser Met Ala Arg Leu Glu Asp Leu Trp Lys Glu Tyr Gln
1               5                   10                  15

Lys Ile Phe Pro Ser Ile Gln Val Ile Thr Ser Ala Phe Arg Ser Ile
            20                  25                  30

Glu Pro Glu Leu Thr Val Tyr Thr
        35                  40
```

<210> SEQ ID NO 31
<211> LENGTH: 30
<212> TYPE: PRT
<213> ORGANISM: Artificial
<220> FEATURE:
<223> OTHER INFORMATION: Alt a 2 derived hyperallergenic molecule

<400> SEQUENCE: 31

```
Cys Leu Lys Lys Ile Glu Ala Ser Phe Glu Leu Ile Glu Glu Asn Gly
1               5                   10                  15

Asp Pro Lys Ile Thr Ser Glu Ile Gln Leu Leu Lys Ala Ser
            20                  25                  30
```

<210> SEQ ID NO 32
<211> LENGTH: 34
<212> TYPE: PRT
<213> ORGANISM: Artificial
<220> FEATURE:
<223> OTHER INFORMATION: Alt a 6 derived hyperallergenic molecule

<400> SEQUENCE: 32

```
Met Thr Ile Thr Lys Ile His Ala Arg Ser Val Tyr Asp Ser Arg Gly
1               5                   10                  15

Asn Pro Thr Val Glu Val Asp Ile Val Thr Glu Thr Gly Leu His Arg
            20                  25                  30

Ala Ile
```

<210> SEQ ID NO 33
<211> LENGTH: 40
<212> TYPE: PRT
<213> ORGANISM: Artificial
<220> FEATURE:
<223> OTHER INFORMATION: Alt a 6 derived hyperallergenic molecule

<400> SEQUENCE: 33

```
Val Thr Glu Thr Gly Leu His Arg Ala Ile Val Pro Ser Gly Ala Ser
1               5                   10                  15

Thr Gly Ser His Glu Ala Cys Glu Leu Arg Asp Gly Asp Lys Ser Lys
            20                  25                  30

Trp Gly Gly Lys Gly Val Thr Lys
        35                  40
```

<210> SEQ ID NO 34
<211> LENGTH: 42
<212> TYPE: PRT
<213> ORGANISM: Artificial
<220> FEATURE:
<223> OTHER INFORMATION: Alt a 6 derived hyperallergenic molecule -continued

```
<400> SEQUENCE: 34

Ala Pro Ala Leu Ile Lys Glu Lys Leu Asp Val Lys Asp Gln Ser Ala
1               5                   10                  15

Val Asp Ala Phe Leu Asn Lys Leu Asp Gly Thr Thr Asn Lys Thr Asn
            20                  25                  30

Leu Gly Ala Asn Ala Ile Leu Gly Val Ser
        35                  40

<210> SEQ ID NO 35
<211> LENGTH: 41
<212> TYPE: PRT
<213> ORGANISM: Artificial
<220> FEATURE:
<223> OTHER INFORMATION: Alt a 6 derived hyperallergenic molecule

<400> SEQUENCE: 35

Glu Lys Gly Val Pro Leu Tyr Ala His Ile Ser Asp Leu Ala Gly Thr
1               5                   10                  15

Lys Lys Pro Tyr Val Leu Pro Val Pro Phe Gln Asn Val Leu Asn Gly
            20                  25                  30

Gly Ser His Ala Gly Gly Arg Leu Ala
        35                  40

<210> SEQ ID NO 36
<211> LENGTH: 40
<212> TYPE: PRT
<213> ORGANISM: Artificial
<220> FEATURE:
<223> OTHER INFORMATION: Alt a 6 derived hyperallergenic molecule

<400> SEQUENCE: 36

Cys Glu Ala Pro Thr Phe Ser Glu Ala Met Arg Gln Gly Ala Glu Val
1               5                   10                  15

Tyr Gln Lys Leu Lys Ala Leu Ala Lys Lys Thr Tyr Gly Gln Ser Ala
            20                  25                  30

Gly Asn Val Gly Asp Glu Gly Gly
        35                  40

<210> SEQ ID NO 37
<211> LENGTH: 40
<212> TYPE: PRT
<213> ORGANISM: Artificial
<220> FEATURE:
<223> OTHER INFORMATION: Alt a 6 derived hyperallergenic molecule

<400> SEQUENCE: 37

Ile Lys Ile Ala Met Asp Val Ala Ser Ser Glu Phe Tyr Lys Ala Asp
1               5                   10                  15

Glu Lys Lys Tyr Asp Leu Asp Phe Lys Asn Pro Asp Ser Asp Lys Ser
            20                  25                  30

Lys Trp Leu Thr Tyr Glu Gln Leu
        35                  40

<210> SEQ ID NO 38
<211> LENGTH: 40
<212> TYPE: PRT
<213> ORGANISM: Artificial
<220> FEATURE:
<223> OTHER INFORMATION: Alt a 6 derived hyperallergenic molecule

<400> SEQUENCE: 38
```

```
Val Ser Ile Glu Asp Pro Phe Ala Glu Asp Trp Glu Ala Trp Ser
1               5                   10                  15

Tyr Phe Phe Lys Thr Tyr Asp Gly Gln Ile Val Gly Asp Leu Thr
                20                  25                  30

Val Thr Asn Pro Glu Phe Ile Lys
                35              40
```

<210> SEQ ID NO 39
<211> LENGTH: 40
<212> TYPE: PRT
<213> ORGANISM: Artificial
<220> FEATURE:
<223> OTHER INFORMATION: Alt a 6 derived hyperallergenic molecule

<400> SEQUENCE: 39

```
Ala Lys Asp Ala Phe Gly Ala Gly Trp Gly Val Met Val Ser His Arg
1               5                   10                  15

Ser Gly Glu Thr Glu Asp Val Thr Ile Ala Asp Ile Val Val Gly Leu
                20                  25                  30

Arg Ser Gly Gln Ile Lys Thr Gly
                35              40
```

<210> SEQ ID NO 40
<211> LENGTH: 38
<212> TYPE: PRT
<213> ORGANISM: Artificial
<220> FEATURE:
<223> OTHER INFORMATION: Alt a 6 derived hyperallergenic molecule

<400> SEQUENCE: 40

```
Ala Pro Ala Arg Ser Glu Arg Leu Ala Lys Leu Asn Gln Ile Leu Arg
1               5                   10                  15

Ile Glu Glu Glu Leu Gly Asp Asn Ala Val Tyr Ala Gly Asn Asn Phe
                20                  25                  30

Arg Thr Ala Val Asn Leu
        35
```

<210> SEQ ID NO 41
<211> LENGTH: 40
<212> TYPE: PRT
<213> ORGANISM: Artificial
<220> FEATURE:
<223> OTHER INFORMATION: Amb a 1 derived hyperallergenic molecule

<400> SEQUENCE: 41

```
Glu Ile Leu Pro Val Asn Glu Thr Arg Arg Leu Thr Thr Ser Gly Ala
1               5                   10                  15

Tyr Asn Ile Ile Asp Gly Cys Trp Arg Gly Lys Ala Asp Trp Ala Glu
                20                  25                  30

Asn Arg Lys Ala Leu Ala Asp Cys
                35              40
```

<210> SEQ ID NO 42
<211> LENGTH: 41
<212> TYPE: PRT
<213> ORGANISM: Artificial
<220> FEATURE:
<223> OTHER INFORMATION: Amb a 1 derived hyperallergenic molecule

<400> SEQUENCE: 42

```
Gly Gly Lys Asp Gly Asp Ile Tyr Thr Val Thr Ser Glu Leu Asp Asp
1               5                   10                  15
```

Asp Val Ala Asn Pro Lys Glu Gly Thr Leu Arg Phe Gly Ala Ala Gln
            20                  25                  30

Asn Arg Pro Leu Trp Ile Ile Phe Glu
            35                  40

<210> SEQ ID NO 43
<211> LENGTH: 31
<212> TYPE: PRT
<213> ORGANISM: Artificial
<220> FEATURE:
<223> OTHER INFORMATION: Amb a 1 derived hyperallergenic molecule

<400> SEQUENCE: 43

Ile Arg Leu Asp Lys Glu Met Val Val Asn Ser Asp Lys Thr Ile Asp
1               5                   10                  15

Gly Arg Gly Ala Lys Val Glu Ile Ile Asn Ala Gly Phe Thr Leu
            20                  25                  30

<210> SEQ ID NO 44
<211> LENGTH: 41
<212> TYPE: PRT
<213> ORGANISM: Artificial
<220> FEATURE:
<223> OTHER INFORMATION: Amb a 1 derived hyperallergenic molecule

<400> SEQUENCE: 44

Asn Val Ile Ile His Asn Ile Asn Met His Asp Val Lys Val Asn Pro
1               5                   10                  15

Gly Gly Leu Ile Lys Ser Asn Asp Gly Pro Ala Ala Pro Arg Ala Gly
            20                  25                  30

Ser Asp Gly Asp Ala Ile Ser Ile Ser
            35                  40

<210> SEQ ID NO 45
<211> LENGTH: 39
<212> TYPE: PRT
<213> ORGANISM: Artificial
<220> FEATURE:
<223> OTHER INFORMATION: Amb a 1 derived hyperallergenic molecule

<400> SEQUENCE: 45

Gly Thr Thr Arg Leu Thr Val Ser Asn Ser Leu Phe Thr Gln His Gln
1               5                   10                  15

Phe Val Leu Leu Phe Gly Ala Gly Asp Glu Asn Ile Glu Asp Arg Gly
            20                  25                  30

Met Leu Ala Thr Val Ala Phe
            35

<210> SEQ ID NO 46
<211> LENGTH: 37
<212> TYPE: PRT
<213> ORGANISM: Artificial
<220> FEATURE:
<223> OTHER INFORMATION: Amb a 1 derived hyperallergenic molecule

<400> SEQUENCE: 46

Asn Thr Phe Thr Asp Asn Val Asp Gln Arg Met Pro Arg Cys Arg His
1               5                   10                  15

Gly Phe Phe Gln Val Val Asn Asn Tyr Asp Lys Trp Gly Ser Tyr
            20                  25                  30

Ala Ile Gly Gly Ser
            35

<210> SEQ ID NO 47
<211> LENGTH: 46
<212> TYPE: PRT
<213> ORGANISM: Artificial
<220> FEATURE:
<223> OTHER INFORMATION: Amb a 1 derived hyperallergenic molecule

<400> SEQUENCE: 47

```
Ile Leu Ser Gln Gly Asn Arg Phe Cys Ala Pro Asp Glu Arg Ser Lys
1               5                   10                  15

Lys Asn Val Leu Gly Arg His Gly Glu Ala Ala Ala Glu Ser Met Lys
            20                  25                  30

Trp Asn Trp Arg Thr Asn Lys Asp Val Leu Glu Asn Gly Ala
        35                  40                  45
```

<210> SEQ ID NO 48
<211> LENGTH: 41
<212> TYPE: PRT
<213> ORGANISM: Artificial
<220> FEATURE:
<223> OTHER INFORMATION: Amb a 1 derived hyperallergenic molecule

<400> SEQUENCE: 48

```
Gly Val Asp Pro Val Leu Thr Pro Glu Gln Ser Ala Gly Met Ile Pro
1               5                   10                  15

Ala Glu Pro Gly Glu Ser Ala Leu Ser Leu Thr Ser Ser Ala Gly Val
            20                  25                  30

Leu Ser Cys Gln Pro Gly Ala Pro Cys
        35                  40
```

<210> SEQ ID NO 49
<211> LENGTH: 44
<212> TYPE: PRT
<213> ORGANISM: Artificial
<220> FEATURE:
<223> OTHER INFORMATION: Art v 1 derived hyperallergenic molecule

<400> SEQUENCE: 49

```
Ser Lys Leu Cys Glu Lys Thr Ser Lys Thr Tyr Ser Gly Lys Cys Asp
1               5                   10                  15

Asn Lys Lys Cys Asp Lys Lys Cys Ile Glu Trp Glu Lys Ala Gln His
            20                  25                  30

Gly Ala Cys His Lys Arg Glu Ala Gly Lys Glu Ser
        35                  40
```

<210> SEQ ID NO 50
<211> LENGTH: 31
<212> TYPE: PRT
<213> ORGANISM: Artificial
<220> FEATURE:
<223> OTHER INFORMATION: Art v 1 derived hyperallergenic molecule

<400> SEQUENCE: 50

```
Ser Cys Phe Cys Tyr Phe Asp Cys Ser Lys Ser Pro Pro Gly Ala Thr
1               5                   10                  15

Pro Ala Pro Pro Gly Ala Ala Pro Pro Pro Ala Ala Gly Gly Ser
            20                  25                  30
```

<210> SEQ ID NO 51
<211> LENGTH: 41
<212> TYPE: PRT
<213> ORGANISM: Artificial
<220> FEATURE:

```
<223> OTHER INFORMATION: Art v 1 derived hyperallergenic molecule

<400> SEQUENCE: 51

Ala Pro Pro Pro Ala Ala Gly Gly Ser Pro Ser Pro Pro Ala Asp Gly
1               5                   10                  15

Gly Ser Pro Pro Pro Ala Asp Gly Gly Ser Pro Val Asp Gly
            20                  25                  30

Gly Ser Pro Pro Pro Ser Thr His
        35                  40

<210> SEQ ID NO 52
<211> LENGTH: 38
<212> TYPE: PRT
<213> ORGANISM: Artificial
<220> FEATURE:
<223> OTHER INFORMATION: Can f 1 derived hyperallergenic molecule

<400> SEQUENCE: 52

Gln Asp Thr Pro Ala Leu Gly Lys Asp Thr Val Ala Val Ser Gly Lys
1               5                   10                  15

Trp Tyr Leu Lys Ala Met Thr Ala Asp Gln Glu Val Pro Glu Lys Pro
            20                  25                  30

Asp Ser Val Thr Pro Met
        35

<210> SEQ ID NO 53
<211> LENGTH: 40
<212> TYPE: PRT
<213> ORGANISM: Artificial
<220> FEATURE:
<223> OTHER INFORMATION: Can f 1 derived hyperallergenic molecule

<400> SEQUENCE: 53

Asp Ser Val Thr Pro Met Ile Leu Lys Ala Gln Lys Gly Gly Asn Leu
1               5                   10                  15

Glu Ala Lys Ile Thr Met Leu Thr Asn Gly Gln Cys Gln Asn Ile Thr
            20                  25                  30

Val Val Leu His Lys Thr Ser Glu
        35                  40

<210> SEQ ID NO 54
<211> LENGTH: 41
<212> TYPE: PRT
<213> ORGANISM: Artificial
<220> FEATURE:
<223> OTHER INFORMATION: Can f 1 derived hyperallergenic molecule

<400> SEQUENCE: 54

Cys Gln Asn Ile Thr Val Val Leu His Lys Thr Ser Glu Pro Gly Lys
1               5                   10                  15

Tyr Thr Ala Tyr Glu Gly Gln Arg Val Val Phe Ile Gln Pro Ser Pro
            20                  25                  30

Val Arg Asp His Tyr Ile Leu Tyr Cys
        35                  40

<210> SEQ ID NO 55
<211> LENGTH: 40
<212> TYPE: PRT
<213> ORGANISM: Artificial
<220> FEATURE:
<223> OTHER INFORMATION: Can f 1 derived hyperallergenic molecule

<400> SEQUENCE: 55
```

```
Gln Pro Ser Pro Val Arg Asp His Tyr Ile Leu Tyr Cys Glu Gly Glu
1               5                   10                  15

Leu His Gly Arg Gln Ile Arg Met Ala Lys Leu Leu Gly Arg Asp Pro
            20                  25                  30

Glu Gln Ser Gln Glu Ala Leu Glu
        35                  40

<210> SEQ ID NO 56
<211> LENGTH: 40
<212> TYPE: PRT
<213> ORGANISM: Artificial
<220> FEATURE:
<223> OTHER INFORMATION: Can f 1 derived hyperallergenic molecule

<400> SEQUENCE: 56

Arg Asp Pro Glu Gln Ser Gln Glu Ala Leu Glu Asp Phe Arg Glu Phe
1               5                   10                  15

Ser Arg Ala Lys Gly Leu Asn Gln Glu Ile Leu Glu Leu Ala Gln Ser
            20                  25                  30

Glu Thr Cys Ser Pro Gly Gly Gln
        35                  40

<210> SEQ ID NO 57
<211> LENGTH: 40
<212> TYPE: PRT
<213> ORGANISM: Artificial
<220> FEATURE:
<223> OTHER INFORMATION: Can f 2 derived hyperallergenic molecule

<400> SEQUENCE: 57

Gln Glu Gly Asn His Glu Glu Pro Gln Gly Gly Leu Glu Glu Leu Ser
1               5                   10                  15

Gly Arg Trp His Ser Val Ala Leu Ala Ser Asn Lys Ser Asp Leu Ile
            20                  25                  30

Lys Pro Trp Gly His Phe Arg Val
        35                  40

<210> SEQ ID NO 58
<211> LENGTH: 40
<212> TYPE: PRT
<213> ORGANISM: Artificial
<220> FEATURE:
<223> OTHER INFORMATION: Can f 2 derived hyperallergenic molecule

<400> SEQUENCE: 58

Pro Trp Gly His Phe Arg Val Phe Ile His Ser Met Ser Ala Lys Asp
1               5                   10                  15

Gly Asn Leu His Gly Asp Ile Leu Ile Pro Gln Asp Gly Gln Cys Glu
            20                  25                  30

Lys Val Ser Leu Thr Ala Phe Lys
        35                  40

<210> SEQ ID NO 59
<211> LENGTH: 38
<212> TYPE: PRT
<213> ORGANISM: Artificial
<220> FEATURE:
<223> OTHER INFORMATION: Can f 2 derived hyperallergenic molecule

<400> SEQUENCE: 59

Cys Glu Lys Val Ser Leu Thr Ala Phe Lys Thr Ala Thr Ser Asn Lys
1               5                   10                  15
```

```
Phe Asp Leu Glu Tyr Trp Gly His Asn Asp Leu Tyr Leu Ala Glu Val
            20                  25                  30

Asp Pro Lys Ser Tyr Leu
        35

<210> SEQ ID NO 60
<211> LENGTH: 39
<212> TYPE: PRT
<213> ORGANISM: Artificial
<220> FEATURE:
<223> OTHER INFORMATION: Can f 2 derived hyperallergenic molecule

<400> SEQUENCE: 60

Asn Asp Leu Tyr Leu Ala Glu Val Asp Pro Lys Ser Tyr Leu Ile Leu
1               5                   10                  15

Tyr Met Ile Asn Gln Tyr Asn Asp Asp Thr Ser Leu Val Ala His Leu
            20                  25                  30

Met Val Arg Asp Leu Ser Arg
        35

<210> SEQ ID NO 61
<211> LENGTH: 42
<212> TYPE: PRT
<213> ORGANISM: Artificial
<220> FEATURE:
<223> OTHER INFORMATION: Can f 2 derived hyperallergenic molecule

<400> SEQUENCE: 61

Val Arg Asp Leu Ser Arg Gln Gln Asp Phe Leu Pro Ala Phe Glu Ser
1               5                   10                  15

Val Cys Glu Asp Ile Gly Leu His Lys Asp Gln Ile Val Val Leu Ser
            20                  25                  30

Asp Asp Asp Arg Cys Gln Gly Ser Arg Asp
        35                  40

<210> SEQ ID NO 62
<211> LENGTH: 34
<212> TYPE: PRT
<213> ORGANISM: Artificial
<220> FEATURE:
<223> OTHER INFORMATION: Fel d 2 derived hyperallergenic molecule

<400> SEQUENCE: 62

Glu Ala His Gln Ser Glu Ile Ala His Arg Phe Asn Asp Leu Gly Glu
1               5                   10                  15

Glu His Phe Arg Gly Leu Val Leu Val Ala Phe Ser Gln Tyr Leu Gln
            20                  25                  30

Gln Cys

<210> SEQ ID NO 63
<211> LENGTH: 35
<212> TYPE: PRT
<213> ORGANISM: Artificial
<220> FEATURE:
<223> OTHER INFORMATION: Fel d 2 derived hyperallergenic molecule

<400> SEQUENCE: 63

Cys Thr Val Ala Ser Leu Arg Asp Lys Tyr Gly Glu Met Ala Asp Cys
1               5                   10                  15

Cys Glu Lys Lys Glu Pro Glu Arg Asn Glu Cys Phe Leu Gln His Lys
            20                  25                  30
```

-continued

```
Asp Asp Asn
        35

<210> SEQ ID NO 64
<211> LENGTH: 30
<212> TYPE: PRT
<213> ORGANISM: Artificial
<220> FEATURE:
<223> OTHER INFORMATION: Fel d 2 derived hyperallergenic molecule

<400> SEQUENCE: 64

Asn Glu Gln Arg Phe Leu Gly Lys Tyr Leu Tyr Glu Ile Ala Arg Arg
1               5                   10                  15

His Pro Tyr Phe Tyr Ala Pro Glu Leu Leu Tyr Tyr Ala Glu
            20                  25                  30

<210> SEQ ID NO 65
<211> LENGTH: 31
<212> TYPE: PRT
<213> ORGANISM: Artificial
<220> FEATURE:
<223> OTHER INFORMATION: Fel d 2 derived hyperallergenic molecule

<400> SEQUENCE: 65

Cys Ala Asp Asp Arg Ala Asp Leu Ala Lys Tyr Ile Cys Glu Asn Gln
1               5                   10                  15

Asp Ser Ile Ser Thr Lys Leu Lys Glu Cys Cys Gly Lys Pro Val
            20                  25                  30

<210> SEQ ID NO 66
<211> LENGTH: 30
<212> TYPE: PRT
<213> ORGANISM: Artificial
<220> FEATURE:
<223> OTHER INFORMATION: Fel d 2 derived hyperallergenic molecule

<400> SEQUENCE: 66

Val Glu Asp Lys Glu Val Cys Lys Asn Tyr Gln Glu Ala Lys Asp Val
1               5                   10                  15

Phe Leu Gly Thr Phe Leu Tyr Glu Tyr Ser Arg Arg His Pro
            20                  25                  30

<210> SEQ ID NO 67
<211> LENGTH: 30
<212> TYPE: PRT
<213> ORGANISM: Artificial
<220> FEATURE:
<223> OTHER INFORMATION: Fel d 2 derived hyperallergenic molecule

<400> SEQUENCE: 67

Leu Ala Lys Glu Tyr Glu Ala Thr Leu Glu Lys Cys Cys Ala Thr Asp
1               5                   10                  15

Asp Pro Pro Ala Cys Tyr Ala His Val Phe Asp Glu Phe Lys
            20                  25                  30

<210> SEQ ID NO 68
<211> LENGTH: 30
<212> TYPE: PRT
<213> ORGANISM: Artificial
<220> FEATURE:
<223> OTHER INFORMATION: Fel d 2 derived hyperallergenic molecule

<400> SEQUENCE: 68

Glu Lys Gln Ile Lys Lys Gln Ser Ala Leu Val Glu Leu Leu Lys His
1               5                   10                  15
```

Lys Pro Lys Ala Thr Glu Glu Gln Leu Lys Thr Val Met Gly
20 25 30

<210> SEQ ID NO 69
<211> LENGTH: 30
<212> TYPE: PRT
<213> ORGANISM: Artificial
<220> FEATURE:
<223> OTHER INFORMATION: Fel d 2 derived hyperallergenic molecule

<400> SEQUENCE: 69

Val Asp Lys Cys Cys Ala Ala Glu Asp Lys Glu Ala Cys Phe Ala Glu
1 5 10 15

Glu Gly Pro Lys Leu Val Ala Ala Ala Gln Ala Ala Leu Ala
20 25 30

<210> SEQ ID NO 70
<211> LENGTH: 42
<212> TYPE: PRT
<213> ORGANISM: Artificial
<220> FEATURE:
<223> OTHER INFORMATION: Fel d 2 derived hyperallergenic molecule

<400> SEQUENCE: 70

Cys Pro Phe Glu Asp His Val Lys Leu Val Asn Glu Val Thr Glu Phe
1 5 10 15

Ala Lys Gly Cys Val Ala Asp Gln Ser Ala Ala Asn Cys Glu Lys Ser
20 25 30

Leu His Glu Leu Leu Gly Asp Lys Leu Cys
35 40

<210> SEQ ID NO 71
<211> LENGTH: 41
<212> TYPE: PRT
<213> ORGANISM: Artificial
<220> FEATURE:
<223> OTHER INFORMATION: Fel d 2 derived hyperallergenic molecule

<400> SEQUENCE: 71

Cys Phe Leu Gln His Lys Asp Asp Asn Pro Gly Phe Gly Gln Leu Val
1 5 10 15

Thr Pro Glu Ala Asp Ala Met Cys Thr Ala Phe His Glu Asn Glu Gln
20 25 30

Arg Phe Leu Gly Lys Tyr Leu Tyr Glu
35 40

<210> SEQ ID NO 72
<211> LENGTH: 42
<212> TYPE: PRT
<213> ORGANISM: Artificial
<220> FEATURE:
<223> OTHER INFORMATION: Fel d 2 derived hyperallergenic molecule

<400> SEQUENCE: 72

Glu Glu Tyr Lys Gly Val Phe Thr Glu Cys Cys Glu Ala Ala Asp Lys
1 5 10 15

Ala Ala Cys Leu Thr Pro Lys Val Asp Ala Leu Arg Glu Lys Val Leu
20 25 30

Ala Ser Ser Ala Lys Glu Arg Leu Lys Cys
35 40

<210> SEQ ID NO 73

```
<211> LENGTH: 38
<212> TYPE: PRT
<213> ORGANISM: Artificial
<220> FEATURE:
<223> OTHER INFORMATION: Fel d 2 derived hyperallergenic molecule

<400> SEQUENCE: 73

Cys Ala Ser Leu Gln Lys Phe Gly Glu Arg Ala Phe Lys Ala Trp Ser
1               5                   10                  15

Val Ala Arg Leu Ser Gln Lys Phe Pro Lys Ala Glu Phe Ala Glu Ile
            20                  25                  30

Ser Lys Leu Val Thr Asp
        35

<210> SEQ ID NO 74
<211> LENGTH: 38
<212> TYPE: PRT
<213> ORGANISM: Artificial
<220> FEATURE:
<223> OTHER INFORMATION: Fel d 2 derived hyperallergenic molecule

<400> SEQUENCE: 74

Phe Ala Glu Ile Ser Lys Leu Val Thr Asp Leu Ala Lys Ile His Lys
1               5                   10                  15

Glu Cys Cys His Gly Asp Leu Leu Glu Cys Ala Asp Asp Arg Ala Asp
            20                  25                  30

Leu Ala Lys Tyr Ile Cys
        35

<210> SEQ ID NO 75
<211> LENGTH: 38
<212> TYPE: PRT
<213> ORGANISM: Artificial
<220> FEATURE:
<223> OTHER INFORMATION: Fel d 2 derived hyperallergenic molecule

<400> SEQUENCE: 75

Cys Gly Lys Pro Val Leu Glu Lys Ser His Cys Ile Ser Glu Val Glu
1               5                   10                  15

Arg Asp Glu Leu Pro Ala Asp Leu Pro Pro Leu Ala Val Asp Phe Val
            20                  25                  30

Glu Asp Lys Glu Val Cys
        35

<210> SEQ ID NO 76
<211> LENGTH: 42
<212> TYPE: PRT
<213> ORGANISM: Artificial
<220> FEATURE:
<223> OTHER INFORMATION: Fel d 2 derived hyperallergenic molecule

<400> SEQUENCE: 76

Cys Glu Leu Phe Glu Lys Leu Gly Glu Tyr Gly Phe Gln Asn Ala Leu
1               5                   10                  15

Leu Val Arg Tyr Thr Lys Lys Val Pro Gln Val Ser Thr Pro Thr Leu
            20                  25                  30

Val Glu Val Ser Arg Ser Leu Gly Lys Val
        35                  40

<210> SEQ ID NO 77
<211> LENGTH: 39
<212> TYPE: PRT
<213> ORGANISM: Artificial
```

```
<220> FEATURE:
<223> OTHER INFORMATION: Fel d 2 derived hyperallergenic molecule

<400> SEQUENCE: 77

Cys Thr His Pro Glu Ala Glu Arg Leu Ser Cys Ala Glu Asp Tyr Leu
1               5                   10                  15

Ser Val Val Leu Asn Arg Leu Cys Val Leu His Glu Lys Thr Pro Val
            20                  25                  30

Ser Glu Arg Val Thr Lys Cys
        35

<210> SEQ ID NO 78
<211> LENGTH: 42
<212> TYPE: PRT
<213> ORGANISM: Artificial
<220> FEATURE:
<223> OTHER INFORMATION: Fel d 2 derived hyperallergenic molecule

<400> SEQUENCE: 78

Cys Thr Glu Ser Leu Val Asn Arg Arg Pro Cys Phe Ser Ala Leu Gln
1               5                   10                  15

Val Asp Glu Thr Tyr Val Pro Lys Glu Phe Ser Ala Glu Thr Phe Thr
            20                  25                  30

Phe His Ala Asp Leu Cys Thr Leu Pro Glu
        35                  40

<210> SEQ ID NO 79
<211> LENGTH: 40
<212> TYPE: PRT
<213> ORGANISM: Artificial
<220> FEATURE:
<223> OTHER INFORMATION: Ole e 1 derived hyperallergenic molecule

<400> SEQUENCE: 79

Glu Asp Ile Pro Gln Pro Pro Val Ser Gln Phe His Ile Gln Gly Gln
1               5                   10                  15

Val Tyr Cys Asp Thr Cys Arg Ala Gly Phe Ile Thr Glu Leu Ser Glu
            20                  25                  30

Phe Ile Pro Gly Ala Ser Leu Arg
        35                  40

<210> SEQ ID NO 80
<211> LENGTH: 31
<212> TYPE: PRT
<213> ORGANISM: Artificial
<220> FEATURE:
<223> OTHER INFORMATION: Ole e 1 derived hyperallergenic molecule

<400> SEQUENCE: 80

Gly Ala Ser Leu Arg Leu Gln Cys Lys Asp Lys Glu Asn Gly Asp Val
1               5                   10                  15

Thr Phe Thr Glu Val Gly Tyr Thr Arg Ala Glu Gly Leu Tyr Ser
            20                  25                  30

<210> SEQ ID NO 81
<211> LENGTH: 37
<212> TYPE: PRT
<213> ORGANISM: Artificial
<220> FEATURE:
<223> OTHER INFORMATION: Ole e 1 derived hyperallergenic molecule

<400> SEQUENCE: 81

Gly Leu Tyr Ser Met Leu Val Glu Arg Asp His Lys Asn Glu Phe Cys
```

-continued

```
1               5                   10                  15
Glu Ile Thr Leu Ile Ser Ser Gly Arg Lys Asp Cys Asn Glu Ile Pro
            20                  25                  30

Thr Glu Gly Trp Ala
        35

<210> SEQ ID NO 82
<211> LENGTH: 35
<212> TYPE: PRT
<213> ORGANISM: Artificial
<220> FEATURE:
<223> OTHER INFORMATION: Ole e 1 derived hyperallergenic molecule

<400> SEQUENCE: 82

Gly Arg Lys Asp Cys Asn Glu Ile Pro Thr Glu Gly Trp Ala Lys Pro
1               5                   10                  15

Ser Leu Lys Phe Lys Leu Asn Thr Val Asn Gly Thr Thr Arg Thr Val
            20                  25                  30

Asn Pro Leu
        35

<210> SEQ ID NO 83
<211> LENGTH: 39
<212> TYPE: PRT
<213> ORGANISM: Artificial
<220> FEATURE:
<223> OTHER INFORMATION: Ole e 1 derived hyperallergenic molecule

<400> SEQUENCE: 83

Leu Asn Thr Val Asn Gly Thr Thr Arg Thr Val Asn Pro Leu Gly Phe
1               5                   10                  15

Phe Lys Lys Glu Ala Leu Pro Lys Cys Ala Gln Val Tyr Asn Lys Leu
            20                  25                  30

Gly Met Tyr Pro Pro Asn Met
        35

<210> SEQ ID NO 84
<211> LENGTH: 30
<212> TYPE: PRT
<213> ORGANISM: Artificial
<220> FEATURE:
<223> OTHER INFORMATION: Par j 2 derived hyperallergenic molecule

<400> SEQUENCE: 84

Gly Glu Glu Ala Cys Gly Lys Val Val Gln Asp Ile Met Pro Cys Leu
1               5                   10                  15

His Phe Val Lys Gly Glu Glu Lys Glu Pro Ser Lys Glu Cys
            20                  25                  30

<210> SEQ ID NO 85
<211> LENGTH: 36
<212> TYPE: PRT
<213> ORGANISM: Artificial
<220> FEATURE:
<223> OTHER INFORMATION: Par j 2 derived hyperallergenic molecule

<400> SEQUENCE: 85

Cys Leu His Phe Val Lys Gly Glu Glu Lys Glu Pro Ser Lys Glu Cys
1               5                   10                  15

Cys Ser Gly Thr Lys Lys Leu Ser Glu Glu Val Lys Thr Thr Glu Gln
            20                  25                  30

Lys Arg Glu Ala
```

<210> SEQ ID NO 86
<211> LENGTH: 37
<212> TYPE: PRT
<213> ORGANISM: Artificial
<220> FEATURE:
<223> OTHER INFORMATION: Par j 2 derived hyperallergenic molecule

<400> SEQUENCE: 86

Cys Cys Ser Gly Thr Lys Lys Leu Ser Glu Glu Val Lys Thr Thr Glu
1               5                   10                  15

Gln Lys Arg Glu Ala Cys Lys Cys Ile Val Arg Ala Thr Lys Gly Ile
            20                  25                  30

Ser Gly Ile Lys Asn
        35

<210> SEQ ID NO 87
<211> LENGTH: 37
<212> TYPE: PRT
<213> ORGANISM: Artificial
<220> FEATURE:
<223> OTHER INFORMATION: Par j 2 derived hyperallergenic molecule

<400> SEQUENCE: 87

Gl

```
<220> FEATURE:
<223> OTHER INFORMATION: Der p 1 derived hyperallergenic molecule

<400> SEQUENCE: 90

His Asn Gly Val Val Gln Glu Ser Tyr Tyr Arg Tyr Val Ala Arg Glu
1               5                   10                  15

Gln Ser Cys Arg Arg Pro Asn Ala Gln Arg Phe Gly Ile Ser Asn
            20                  25                  30

<210> SEQ ID NO 91
<211> LENGTH: 37
<212> TYPE: PRT
<213> ORGANISM: Artificial
<220> FEATURE:
<223> OTHER INFORMATION: Der p 1 derived hyperallergenic molecule

<400> SEQUENCE: 91

Arg Glu Gln Ser Cys Arg Arg Pro Asn Ala Gln Arg Phe Gly Ile Ser
1               5                   10                  15

Asn Tyr Cys Gln Ile Tyr Pro Pro Asn Val Asn Lys Ile Arg Glu Ala
            20                  25                  30

Leu Ala Gln Thr His
        35

<210> SEQ ID NO 92
<211> LENGTH: 31
<212> TYPE: PRT
<213> ORGANISM: Artificial
<220> FEATURE:
<223> OTHER INFORMATION: Der p 1 derived hyperallergenic molecule

<400> SEQUENCE: 92

Lys Asp Leu Asp Ala Phe Arg His Tyr Asp Gly Arg Thr Ile Ile Gln
1               5                   10                  15

Arg Asp Asn Gly Tyr Gln Pro Asn Tyr His Ala Val Asn Ile Val
            20                  25                  30

<210> SEQ ID NO 93
<211> LENGTH: 33
<212> TYPE: PRT
<213> ORGANISM: Artificial
<220> FEATURE:
<223> OTHER INFORMATION: Der p 1 derived hyperallergenic molecule

<400> SEQUENCE: 93

Gly Arg Thr Ile Ile Gln Arg Asp Asn Gly Tyr Gln Pro Asn Tyr His
1               5                   10                  15

Ala Val Asn Ile Val Gly Tyr Ser Asn Ala Gln Gly Val Asp Tyr Trp
            20                  25                  30

Ile

<210> SEQ ID NO 94
<211> LENGTH: 34
<212> TYPE: PRT
<213> ORGANISM: Artificial
<220> FEATURE:
<223> OTHER INFORMATION: Der p 1 derived hyperallergenic molecule

<400> SEQUENCE: 94

Val Gly Tyr Ser Asn Ala Gln Gly Val Asp Tyr Trp Ile Val Arg Asn
1               5                   10                  15

Ser Trp Asp Thr Asn Trp Gly Asp Asn Gly Tyr Gly Tyr Phe Ala Ala
            20                  25                  30
```

Asn Ile

<210> SEQ ID NO 95
<211> LENGTH: 35
<212> TYPE: PRT
<213> ORGANISM: Artificial
<220> FEATURE:
<223> OTHER INFORMATION: Der p 1 derived hyperallergenic molecule

<400> SEQUENCE: 95

Val Arg Asn Ser Trp Asp Thr Asn Trp Gly Asp Asn Gly Tyr Gly Tyr
1               5                   10                  15

Phe Ala Ala Asn Ile Asp Leu Met Met Ile Glu Glu Tyr Pro Tyr Val
            20                  25                  30

Val Ile Leu
        35

<210> SEQ ID NO 96
<211> LENGTH: 33
<212> TYPE: PRT
<213> ORGANISM: Artificial
<220> FEATURE:
<223> OTHER INFORMATION: Der p 2 derived hyperallergenic molecule

<400> SEQUENCE: 96

Asp Gln Val Asp Val Lys Asp Cys Ala Asn His Glu Ile Lys Lys Val
1               5                   10                  15

Leu Val Pro Gly Cys His Gly Ser Glu Pro Cys Ile Ile His Arg Gly
            20                  25                  30

Lys

<210> SEQ ID NO 97
<211> LENGTH: 31
<212> TYPE: PRT
<213> ORGANISM: Artificial
<220> FEATURE:
<223> OTHER INFORMATION: Der p 2 derived hyperallergenic molecule

<400> SEQUENCE: 97

Cys His Gly Ser Glu Pro Cys Ile Ile His Arg Gly Lys Pro Phe Gln
1               5                   10                  15

Leu Glu Ala Val Phe Glu Ala Asn Gln Asn Ser Lys Thr Ala Lys
            20                  25                  30

<210> SEQ ID NO 98
<211> LENGTH: 32
<212> TYPE: PRT
<213> ORGANISM: Artificial
<220> FEATURE:
<223> OTHER INFORMATION: Der p 2 derived hyperallergenic molecule

<400> SEQUENCE: 98

Glu Ala Asn Gln Asn Ser Lys Thr Ala Lys Ile Glu Ile Lys Ala Ser
1               5                   10                  15

Ile Glu Gly Leu Glu Val Asp Val Pro Gly Ile Asp Pro Asn Ala Cys
            20                  25                  30

<210> SEQ ID NO 99
<211> LENGTH: 42
<212> TYPE: PRT
<213> ORGANISM: Artificial
<220> FEATURE:
<223> OTHER INFORMATION: Der p 2 derived hyperallergenic molecule

<400> SEQUENCE: 99

Glu Val Asp Val Pro Gly Ile Asp Pro Asn Ala Cys His Tyr Met Lys
1               5                   10                  15

Cys Pro Leu Val Lys Gly Gln Gln Tyr Asp Ile Lys Tyr Thr Trp Ile
            20                  25                  30

Val Pro Lys Ile Ala Pro Lys Ser Glu Asn
        35                  40

<210> SEQ ID NO 100
<211> LENGTH: 32
<212> TYPE: PRT
<213> ORGANISM: Artificial
<220> FEATURE:
<223> OTHER INFORMATION: Der p 2 derived hyperallergenic molecule

<400> SEQUENCE: 100

Ala Pro Lys Ser Glu Asn Val Val Thr Val Lys Val Met Gly Asp
1               5                   10                  15

Asn Gly Val Leu Ala Cys Ala Ile Ala Thr His Ala Lys Ile Arg Asp
            20                  25                  30

<210> SEQ ID NO 101
<211> LENGTH: 35
<212> TYPE: PRT
<213> ORGANISM: Artificial
<220> FEATURE:
<223> OTHER INFORMATION: Der p 5 derived hyperallergenic molecule

<400> SEQUENCE: 101

Met Glu Asp Lys Lys His Asp Tyr Gln Asn Glu Phe Asp Phe Leu Leu
1               5                   10                  15

Met Glu Arg Ile His Glu Gln Ile Lys Lys Gly Glu Leu Ala Leu Phe
            20                  25                  30

Tyr Leu Gln
        35

<210> SEQ ID NO 102
<211> LENGTH: 36
<212> TYPE: PRT
<213> ORGANISM: Artificial
<220> FEATURE:
<223> OTHER INFORMATION: Der p 5 derived hyperallergenic molecule

<400> SEQUENCE: 102

Lys Lys Gly Glu Leu Ala Leu Phe Tyr Leu Gln Glu Gln Ile Asn His
1               5                   10                  15

Phe Glu Glu Lys Pro Thr Lys Glu Met Lys Asp Lys Ile Val Ala Glu
            20                  25                  30

Met Asp Thr Ile
        35

<210> SEQ ID NO 103
<211> LENGTH: 31
<212> TYPE: PRT
<213> ORGANISM: Artificial
<220> FEATURE:
<223> OTHER INFORMATION: Der p 5 derived hyperallergenic molecule

<400> SEQUENCE: 103

Asp Gly Val Arg Gly Val Leu Asp Arg Leu Met Gln Arg Lys Asp Leu
1               5                   10                  15

```
Asp Ile Phe Glu Gln Tyr Asn Leu Glu Met Ala Lys Lys Ser Gly
            20                  25                  30
```

<210> SEQ ID NO 104
<211> LENGTH: 36
<212> TYPE: PRT
<213> ORGANISM: Artificial
<220> FEATURE:
<223> OTHER INFORMATION: Der p 5 derived hyperallergenic molecule

<400> SEQUENCE: 104

```
Asp Leu Asp Ile Phe Glu Gln Tyr Asn Leu Glu Met Ala Lys Lys Ser
1               5                   10                  15

Gly Asp Ile Leu Glu Arg Asp Leu Lys Lys Glu Ala Arg Val Lys
            20                  25                  30

Lys Ile Glu Val
        35
```

<210> SEQ ID NO 105
<211> LENGTH: 30
<212> TYPE: PRT
<213> ORGANISM: Artificial
<220> FEATURE:
<223> OTHER INFORMATION: Der p 7 derived hyperallergenic molecule

<400> SEQUENCE: 105

```
Asp Pro Ile His Tyr Asp Lys Ile Thr Glu Glu Ile Asn Lys Ala Val
1               5                   10                  15

Asp Glu Ala Val Ala Ala Ile Glu Lys Ser Glu Thr Phe Asp
            20                  25                  30
```

<210> SEQ ID NO 106
<211> LENGTH: 31
<212> TYPE: PRT
<213> ORGANISM: Artificial
<220> FEATURE:
<223> OTHER INFORMATION: Der p 7 derived hyperallergenic molecule

<400> SEQUENCE: 106

```
Val Ala Ala Ile Glu Lys Ser Glu Thr Phe Asp Pro Met Lys Val Pro
1               5                   10                  15

Asp His Ser Asp Lys Phe Glu Arg His Ile Gly Ile Ile Asp Leu
            20                  25                  30
```

<210> SEQ ID NO 107
<211> LENGTH: 31
<212> TYPE: PRT
<213> ORGANISM: Artificial
<220> FEATURE:
<223> OTHER INFORMATION: Der p 7 derived hyperallergenic molecule

<400> SEQUENCE: 107

```
Leu Lys Gly Glu Leu Asp Met Arg Asn Ile Gln Val Arg Gly Leu Lys
1               5                   10                  15

Gln Met Lys Arg Val Gly Asp Ala Asn Val Lys Ser Glu Asp Gly
            20                  25                  30
```

<210> SEQ ID NO 108
<211> LENGTH: 36
<212> TYPE: PRT
<213> ORGANISM: Artificial
<220> FEATURE:
<223> OTHER INFORMATION: Der p 7 derived hyperallergenic molecule

<400> SEQUENCE: 108

Val His Asp Asp Val Val Ser Met Glu Tyr Asp Leu Ala Tyr Lys Leu
1               5                   10                  15

Gly Asp Leu His Pro Asn Thr His Val Ile Ser Asp Ile Gln Asp Phe
                20                  25                  30

Val Val Glu Leu
            35

<210> SEQ ID NO 109
<211> LENGTH: 31
<212> TYPE: PRT
<213> ORGANISM: Artificial
<220> FEATURE:
<223> OTHER INFORMATION: Der p 7 derived hyperallergenic molecule

<400> SEQUENCE: 109

Leu Ser Leu Glu Val Ser Glu Glu Gly Asn Met Thr Leu Thr Ser Phe
1               5                   10                  15

Glu Val Arg Gln Phe Ala Asn Val Val Asn His Ile Gly Gly Leu
                20                  25                  30

<210> SEQ ID NO 110
<211> LENGTH: 34
<212> TYPE: PRT
<213> ORGANISM: Artificial
<220> FEATURE:
<223> OTHER INFORMATION: Der p 7 derived hyperallergenic molecule

<400> SEQUENCE: 110

Leu Ser Asp Val Leu Thr Ala Ile Phe Gln Thr Val Arg Ala Glu
1               5                   10                  15

Met Thr Lys Val Leu Ala Pro Ala Phe Lys Lys Glu Leu Glu Arg Asn
                20                  25                  30

Asn Gln

<210> SEQ ID NO 111
<211> LENGTH: 35
<212> TYPE: PRT
<213> ORGANISM: Artificial
<220> FEATURE:
<223> OTHER INFORMATION: Der p 10 derived hyperallergenic molecule

<400> SEQUENCE: 111

Met Glu Ala Ile Lys Lys Lys Met Gln Ala Met Lys Leu Glu Lys Asp
1               5                   10                  15

Asn Ala Ile Asp Arg Ala Glu Ile Ala Glu Gln Lys Ala Arg Asp Ala
                20                  25                  30

Asn Leu Arg
        35

<210> SEQ ID NO 112
<211> LENGTH: 35
<212> TYPE: PRT
<213> ORGANISM: Artificial
<220> FEATURE:
<223> OTHER INFORMATION: Der p 10 derived hyperallergenic molecule

<400> SEQUENCE: 112

Ala Glu Lys Ser Glu Glu Glu Val Arg Ala Leu Gln Lys Lys Ile Gln
1               5                   10                  15

Gln Ile Glu Asn Glu Leu Asp Gln Val Gln Glu Gln Leu Ser Ala Ala
                20                  25                  30

Asn Thr Lys
        35

<210> SEQ ID NO 113
<211> LENGTH: 40
<212> TYPE: PRT
<213> ORGANISM: Artificial
<220> FEATURE:
<223> OTHER INFORMATION: Der p 10 derived hyperallergenic molecule

<400> SEQUENCE: 113

Leu Glu Glu Lys Glu Lys Ala Leu Gln Thr Ala Glu Gly Asp Val Ala
1               5                   10                  15

Ala Leu Asn Arg Arg Ile Gln Leu Ile Glu Glu Asp Leu Glu Arg Ser
            20                  25                  30

Glu Glu Arg Leu Lys Ile Ala Thr
        35                  40

<210> SEQ ID NO 114
<211> LENGTH: 35
<212> TYPE: PRT
<213> ORGANISM: Artificial
<220> FEATURE:
<223> OTHER INFORMATION: Der p 10 derived hyperallergenic molecule

<400> SEQUENCE: 114

Ala Lys Leu Glu Glu Ala Ser Gln Ser Ala Asp Glu Ser Glu Arg Met
1               5                   10                  15

Arg Lys Met Leu Glu His Arg Ser Ile Thr Asp Glu Glu Arg Met Glu
            20                  25                  30

Gly Leu Glu
        35

<210> SEQ ID NO 115
<211> LENGTH: 31
<212> TYPE: PRT
<213> ORGANISM: Artificial
<220> FEATURE:
<223> OTHER INFORMATION: Der p 10 derived hyperallergenic molecule

<400> SEQUENCE: 115

Arg Met Glu Gly Leu Glu Asn Gln Leu Lys Glu Ala Arg Met Met Ala
1               5                   10                  15

Glu Asp Ala Asp Arg Lys Tyr Asp Glu Val Ala Arg Lys Leu Ala
            20                  25                  30

<210> SEQ ID NO 116
<211> LENGTH: 31
<212> TYPE: PRT
<213> ORGANISM: Artificial
<220> FEATURE:
<223> OTHER INFORMATION: Der p 10 derived hyperallergenic molecule

<400> SEQUENCE: 116

Asp Leu Glu Arg Ala Glu Glu Arg Ala Glu Thr Gly Glu Ser Lys Ile
1               5                   10                  15

Val Glu Leu Glu Glu Glu Leu Arg Val Val Gly Asn Asn Leu Lys
            20                  25                  30

<210> SEQ ID NO 117
<211> LENGTH: 41
<212> TYPE: PRT
<213> ORGANISM: Artificial
<220> FEATURE:

<223> OTHER INFORMATION: Der p 10 derived hyperallergenic molecule

<400> SEQUENCE: 117

Ser Glu Glu Lys Ala Gln Gln Arg Glu Ala His Glu Gln Gln Ile
1               5                   10                  15

Arg Ile Met Thr Thr Lys Leu Lys Glu Ala Glu Ala Arg Ala Glu Phe
            20                  25                  30

Ala Glu Arg Ser Val Gln Lys Leu Gln
        35                  40

<210> SEQ ID NO 118
<211> LENGTH: 35
<212> TYPE: PRT
<213> ORGANISM: Artificial
<220> FEATURE:
<223> OTHER INFORMATION: Der p 10 derived hyperallergenic molecule

<400> SEQUENCE: 118

Gln Lys Glu Val Asp Arg Leu Glu Asp Glu Leu Val His Glu Lys Glu
1               5                   10                  15

Lys Tyr Lys Ser Ile Ser Asp Glu Leu Asp Gln Thr Phe Ala Glu Leu
            20                  25                  30

Thr Gly Tyr
        35

<210> SEQ ID NO 119
<211> LENGTH: 35
<212> TYPE: PRT
<213> ORGANISM: Artificial
<220> FEATURE:
<223> OTHER INFORMATION: Der p 21 derived hyperallergenic molecule

<400> SEQUENCE: 119

Met Phe Ile Val Gly Asp Lys Lys Glu Asp Glu Trp Arg Met Ala Phe
1               5                   10                  15

Asp Arg Leu Met Met Glu Glu Leu Glu Thr Lys Ile Asp Gln Val Glu
            20                  25                  30

Lys Gly Leu
35

<210> SEQ ID NO 120
<211> LENGTH: 37
<212> TYPE: PRT
<213> ORGANISM: Artificial
<220> FEATURE:
<223> OTHER INFORMATION: Der p 21 derived hyperallergenic molecule

<400> SEQUENCE: 120

Leu His Leu Ser Glu Gln Tyr Lys Glu Leu Glu Lys Thr Lys Ser Lys
1 5 10 15

Glu Leu Lys Glu Gln Ile Leu Arg Glu Leu Thr Ile Gly Glu Asn Phe
20 25 30

Met Lys Gly Ala Leu
35

<210> SEQ ID NO 121
<211> LENGTH: 31
<212> TYPE: PRT
<213> ORGANISM: Artificial
<220> FEATURE:
<223> OTHER INFORMATION: Der p 21 derived hyperallergenic molecule

<400> SEQUENCE: 121

```
Gly Ala Leu Lys Phe Phe Glu Met Glu Ala Lys Arg Thr Asp Leu Asn
1               5                   10                  15

Met Phe Glu Arg Tyr Asn Tyr Glu Phe Ala Leu Glu Ser Ile Lys
            20                  25                  30
```

<210> SEQ ID NO 122
<211> LENGTH: 33
<212> TYPE: PRT
<213> ORGANISM: Artificial
<220> FEATURE:
<223> OTHER INFORMATION: Der p 21 derived hyperallergenic molecule

<400> SEQUENCE: 122

```
Tyr Asn Tyr Glu Phe Ala Leu Glu Ser Ile Lys Leu Leu Ile Lys Lys
1               5                   10                  15

Leu Asp Glu Leu Ala Lys Lys Val Lys Ala Val Asn Pro Asp Glu Tyr
            20                  25                  30

Tyr
```

<210> SEQ ID NO 123
<211> LENGTH: 32
<212> TYPE: PRT
<213> ORGANISM: Artificial
<220> FEATURE:
<223> OTHER INFORMATION: Clone 30 derived hyperallergenic molecule

<400> SEQUENCE: 123

```
Met Ala Asn Asp Asn Asp Asp Pro Thr Thr Thr Val His Pro Thr
1               5                   10                  15

Thr Thr Glu Gln Pro Asp Asp Lys Phe Glu Cys Pro Ser Arg Phe Gly
            20                  25                  30
```

<210> SEQ ID NO 124
<211> LENGTH: 34
<212> TYPE: PRT
<213> ORGANISM: Artificial
<220> FEATURE:
<223> OTHER INFORMATION: Clone 30 derived hyperallergenic molecule

<400> SEQUENCE: 124

```
Pro Thr Thr Thr Glu Gln Pro Asp Asp Lys Phe Glu Cys Pro Ser Arg
1               5                   10                  15

Phe Gly Tyr Phe Ala Asp Pro Lys Asp Pro His Lys Phe Tyr Ile Cys
            20                  25                  30

Ser Asn
```

<210> SEQ ID NO 125
<211> LENGTH: 39
<212> TYPE: PRT
<213> ORGANISM: Artificial
<220> FEATURE:
<223> OTHER INFORMATION: Clone 30 derived hyperallergenic molecule

<400> SEQUENCE: 125

```
Gly Tyr Phe Ala Asp Pro Lys Asp Pro His Lys Phe Tyr Ile Cys Ser
1               5                   10                  15

Asn Trp Glu Ala Val His Lys Asp Cys Pro Gly Asn Thr Arg Trp Asn
            20                  25                  30

Glu Asp Glu Glu Thr Cys Thr
            35
```

```
<210> SEQ ID NO 126
<211> LENGTH: 30
<212> TYPE: PRT
<213> ORGANISM: Artificial
<220> FEATURE:
<223> OTHER INFORMATION: Bet v 1 derived hyperallergenic molecule

<400> SEQUENCE: 126

Leu Phe Pro Lys Val Ala Pro Gln Ala Ile Ser Ser Val Glu Asn Ile
1               5                   10                  15

Glu Gly Asn Gly Gly Pro Gly Thr Ile Lys Lys Ile Ser Phe
            20                  25                  30

<210> SEQ ID NO 127
<211> LENGTH: 30
<212> TYPE: PRT
<213> ORGANISM: Artificial
<220> FEATURE:
<223> OTHER INFORMATION: Bet v 1 derived hyperallergenic molecule

<400> SEQUENCE: 127

Gly Pro Gly Thr Ile Lys Lys Ile Ser Phe Pro Glu Gly Phe Pro Phe
1               5                   10                  15

Lys Tyr Val Lys Asp Arg Val Asp Glu Val Asp His Thr Asn
            20                  25                  30

<210> SEQ ID NO 128
<211> LENGTH: 30
<212> TYPE: PRT
<213> ORGANISM: Artificial
<220> FEATURE:
<223> OTHER INFORMATION: Bet v 1 derived hyperallergenic molecule

<400> SEQUENCE: 128

Val Asp His Thr Asn Phe Lys Tyr Asn Tyr Ser Val Ile Glu Gly Gly
1               5                   10                  15

Pro Ile Gly Asp Thr Leu Glu Lys Ile Ser Asn Glu Ile Lys
            20                  25                  30

<210> SEQ ID NO 129
<211> LENGTH: 35
<212> TYPE: PRT
<213> ORGANISM: Artificial
<220> FEATURE:
<223> OTHER INFORMATION: Fel d 1 chain 1 derived hyperallergenic
      molecule

<400> SEQUENCE: 129

Glu Ile Cys Pro Ala Val Lys Arg Asp Val Asp Leu Phe Leu Thr Gly
1               5                   10                  15

Thr Pro Asp Glu Tyr Val Glu Gln Val Ala Gln Tyr Lys Ala Leu Pro
            20                  25                  30

Val Val Cys
        35

<210> SEQ ID NO 130
<211> LENGTH: 36
<212> TYPE: PRT
<213> ORGANISM: Artificial
<220> FEATURE:
<223> OTHER INFORMATION: Fel d 1 chain 1 derived hyperallergenic
      molecule
```

```
<400> SEQUENCE: 130

Leu Glu Asn Ala Arg Ile Leu Lys Asn Cys Val Asp Ala Lys Met Thr
1 5 10 15

Glu Glu Asp Lys Glu Asn Ala Leu Ser Leu Leu Asp Lys Ile Tyr Thr
20 25 30

Ser Pro Leu Cys
35

<210> SEQ ID NO 131
<211> LENGTH: 35
<212> TYPE: PRT
<213> ORGANISM: Artificial
<220> FEATURE:
<223> OTHER INFORMATION: Fel d 1 chain 2 derived hyperallergenic molecule

<400> SEQUENCE: 131

Val Lys Met Ala Ile Thr Cys Pro Ile Phe Tyr Asp Val Phe Phe Ala
1 5 10 15

Val Ala Asn Gly Asn Glu Leu Leu Leu Asp Leu Ser Leu Thr Lys Val
20 25 30

Asn Ala Cys
35

<210> SEQ ID NO 132
<211> LENGTH: 30
<212> TYPE: PRT
<213> ORGANISM: Artificial
<220> FEATURE:
<223> OTHER INFORMATION: Fel d 1 chain 2 derived hyperallergenic molecule

<400> SEQUENCE: 132

Thr Glu Pro Glu Arg Thr Ala Met Lys Lys Ile Gln Asp Cys Tyr Val
1 5 10 15

Glu Asn Gly Leu Ile Ser Arg Val Leu Asp Gly Leu Val Cys
20 25 30

<210> SEQ ID NO 133
<211> LENGTH: 30
<212> TYPE: PRT
<213> ORGANISM: Artificial
<220> FEATURE:
<223> OTHER INFORMATION: Fel d 1 chain 2 derived hyperallergenic molecule

<400> SEQUENCE: 133

Cys Met Thr Thr Ile Ser Ser Ser Lys Asp Cys Met Gly Glu Ala Val
1 5 10 15

Gln Asn Thr Val Glu Asp Leu Lys Leu Asn Thr Leu Gly Arg
20 25 30

<210> SEQ ID NO 134
<211> LENGTH: 32
<212> TYPE: PRT
<213> ORGANISM: Artificial
<220> FEATURE:
<223> OTHER INFORMATION: Phl p 5 derived hyperallergenic molecule

<400> SEQUENCE: 134

Cys Gly Ala Ala Ser Asn Lys Ala Phe Ala Glu Gly Leu Ser Gly Glu
1 5 10 15
```

```
Pro Lys Gly Ala Ala Glu Ser Ser Ser Lys Ala Ala Leu Thr Ser Lys
            20                  25                  30

<210> SEQ ID NO 135
<211> LENGTH: 34
<212> TYPE: PRT
<213> ORGANISM: Artificial
<220> FEATURE:
<223> OTHER INFORMATION: Phl p 5 derived hyperallergenic molecule

<400> SEQUENCE: 135

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Glu Ala Ala Pro Ala Gly
            20                  25                  30

Lys Cys

<210> SEQ ID NO 136
<211> LENGTH: 32
<212> TYPE: PRT
<213> ORGANISM: Artificial
<220> FEATURE:
<223> OTHER INFORMATION: Phl p 5 derived hyperallergenic molecule

<400> SEQUENCE: 136

Ala Tyr Lys Leu Ala Tyr Lys Thr Ala Glu Gly Ala Thr Pro Glu Ala
1               5                   10                  15

Lys Tyr Asp Ala Tyr Val Ala Thr Leu Ser Glu Ala Leu Arg Ile Cys
            20                  25                  30

<210> SEQ ID NO 137
<211> LENGTH: 31
<212> TYPE: PRT
<213> ORGANISM: Artificial
<220> FEATURE:
<223> OTHER INFORMATION: Phl p 5 derived hyperallergenic molecule

<400> SEQUENCE: 137

Cys Glu Ala Ala Phe Asn Asp Ala Ile Lys Ala Ser Thr Gly Gly Ala
1               5                   10                  15

Tyr Glu Ser Tyr Lys Phe Ile Pro Ala Leu Glu Ala Ala Val Lys
            20                  25                  30

<210> SEQ ID NO 138
<211> LENGTH: 33
<212> TYPE: PRT
<213> ORGANISM: Artificial
<220> FEATURE:
<223> OTHER INFORMATION: Phl p 5 derived hyperallergenic molecule

<400> SEQUENCE: 138

Thr Val Ala Thr Ala Pro Glu Val Lys Tyr Thr Val Phe Glu Thr Ala
1               5                   10                  15

Leu Lys Lys Ala Ile Thr Ala Met Ser Glu Ala Gln Lys Ala Ala Lys
            20                  25                  30

Cys

<210> SEQ ID NO 139
<211> LENGTH: 38
<212> TYPE: PRT
<213> ORGANISM: Artificial
<220> FEATURE:
<223> OTHER INFORMATION: Phl p 5 derived hyperallergenic molecule
```

-continued

<400> SEQUENCE: 139

Cys Ala Glu Glu Val Lys Val Ile Pro Ala Gly Glu Leu Gln Val Ile
1               5                   10                  15

Glu Lys Val Asp Ala Ala Phe Lys Val Ala Ala Thr Ala Ala Asn Ala
            20                  25                  30

Ala Pro Ala Asn Asp Lys
        35

<210> SEQ ID NO 140
<211> LENGTH: 70
<212> TYPE: PRT
<213> ORGANISM: Artificial
<220> FEATURE:
<223> OTHER INFORMATION: Clone 30 Dermatophagoides pteronyssinus
      allergen

<400> SEQUENCE: 140

Met Ala Asn Asp Asn Asp Asp Pro Thr Thr Thr Val His Pro Thr
1               5                   10                  15

Thr Thr Glu Gln Pro Asp Lys Phe Glu Cys Pro Ser Arg Phe Gly
            20                  25                  30

Tyr Phe Ala Asp Pro Lys Asp Pro His Lys Phe Tyr Ile Cys Ser Asn
        35                  40                  45

Trp Glu Ala Val His Lys Asp Cys Pro Gly Asn Thr Arg Trp Asn Glu
    50                  55                  60

Asp Glu Glu Thr Cys Thr
65                  70

<210> SEQ ID NO 141
<211> LENGTH: 37
<212> TYPE: PRT
<213> ORGANISM: Artificial
<220> FEATURE:
<223> OTHER INFORMATION: Phl p 5 derived peptide

<400> SEQUENCE: 141

Cys Phe Val Ala Thr Phe Gly Ala Ala Ser Asn Lys Ala Phe Ala Glu
1               5                   10                  15

Gly Leu Ser Gly Glu Pro Lys Gly Ala Ala Glu Ser Ser Ser Lys Ala
            20                  25                  30

Ala Leu Thr Ser Lys
        35

<210> SEQ ID NO 142
<211> LENGTH: 29
<212> TYPE: PRT
<213> ORGANISM: Artificial
<220> FEATURE:
<223> OTHER INFORMATION: Phl p 5 derived peptide

<400> SEQUENCE: 142

Ala Asp Leu Gly Tyr Gly Pro Ala Thr Pro Ala Ala Pro Ala Ala Gly
1               5                   10                  15

Tyr Thr Pro Ala Thr Pro Ala Ala Pro Ala Glu Ala Cys
            20                  25